United States Patent [19]
Furuya et al.

[11] Patent Number: 5,817,819
[45] Date of Patent: Oct. 6, 1998

[54] CONDENSED-RING THIOPHENE DERIVATIVES, THEIR PRODUCTION AND USE

[75] Inventors: Shuichi Furuya; Nobuo Choh; Koichi Kato; Shuji Hinuma, all of Ibaraki, Japan

[73] Assignee: Takeda Chemical Industries, Ltd., Osaka, Japan

[21] Appl. No.: 454,304

[22] PCT Filed: Apr. 14, 1995

[86] PCT No.: PCT/JP95/00728

§ 371 Date: Jun. 16, 1995

§ 102(e) Date: Jun. 16, 1995

[87] PCT Pub. No.: WO95/28405

PCT Pub. Date: Oct. 26, 1995

[30] Foreign Application Priority Data

| Apr. 19, 1994 | [JP] | Japan | 6-80732 |
| Aug. 19, 1994 | [JP] | Japan | 6-195541 |
| Nov. 4, 1994 | [JP] | Japan | 6-271010 |
| Feb. 8, 1995 | [JP] | Japan | 7-20717 |
| Feb. 28, 1995 | [JP] | Japan | 7-40151 |

[51] Int. Cl.$^6$ .............................................. C07D 495/04
[52] U.S. Cl. ............................................................ 546/114
[58] Field of Search ............................. 546/114; 514/301

[56] References Cited

U.S. PATENT DOCUMENTS

| 5,654,296 | 8/1997 | Kato et al. | 540/476 |
| 5,677,184 | 10/1997 | Onda et al. | 435/360 |
| 5,691,353 | 11/1997 | Bryant et al. | 514/319 |

FOREIGN PATENT DOCUMENTS

| 0 443 568 | 8/1991 | European Pat. Off. . |
| 0 520 423 | 12/1992 | European Pat. Off. . |
| 2 006 505 | 8/1971 | Germany . |
| 293 824 | 9/1991 | Germany . |
| 1-213284 | 8/1989 | Japan . |
| 2-225485 | 9/1990 | Japan . |
| 89/02432 | 3/1989 | WIPO . |
| 94/20460 | 9/1994 | WIPO . |

OTHER PUBLICATIONS

Malamas et al., "Quinazolineacetic Acids and Related Analogues as Aldose Reductase Inhibitors", Journal of Mecinal Chemistry, vol. 34, pp. 1492–1503, 1991.

Gillis et al., "Synthesis and antibacterial evaluation of 4,7–dihydro–oxothieno [2,3–b]pyridine–5–carboxylic acids", European Journal of Medicinal Chemistry, vol. 13, No. 3, pp. 265–269, 1978.

Bohm et al., Pharmazie, 41, 661, (1986) and Chemical Abstracts vol. 106, 1978, 213890j.

Jameson, Anterior Pituitary, Cecil Textbook of Medicine, 20th Edition, vol. 2, p. 1205–1210, 1996.

*Primary Examiner*—Mukund J. Shah
*Assistant Examiner*—Deepak R. Rao
*Attorney, Agent, or Firm*—Foley & Lardner

[57] ABSTRACT

A gonadotropin-releasing hormone antagonistic composition, which comprises an optionally substituted condensed-bicyclic compound consisting of a homo or hetero 5 to 7 membered ring and a homo or hetero 5 to 7 membered ring is effective as a propylactic or therapeutic agent for the prevention or treatment of several hormone dependent diseases, for example, a sex hormone dependent cancer (e.g. prostatic cancer, cancer of uterine cervix, breast cancer, pituitary adenoma), benign prostatic hypertrophy, myoma of the uterus, endometriosis, precocious puberty, amenorrhea, premenstrual syndrome, polycystic ovary syndrome and acne vulgaris; is effective as a fertility controlling agent in both sexes (e.g. a pregnancy controlling agent and a menstrual cycle controlling agent); can be used as a contraceptive of male or female, as an ovulation-inducing agent of female; can be used as an infertility treating agent by using a rebound effect owing to a stoppage of administration thereof; is useful as modulating estrous cycles in animals in the field of animal husbandry, as an agent fro improving the quality of edible meat or promoting the growth of animals; is useful as an agent of spawning promotion in fish.

11 Claims, No Drawings

CONDENSED-RING THIOPHENE DERIVATIVES, THEIR PRODUCTION AND USE

TECHNICAL FIELD

The present invention relates to a pharmaceutical composition for antagonizing a gonadotropin-releasing hormone (GnRH) containing a condensed-bycyclic compound consisting of a homo or hetero 5 to 7-membered ring group and a homo or hetero 5 to 7-membered ring group. The present invention also relates to novel condensed-ring hiophene derivatives and salts thereof. The present invention further relates to methods for manufacturing the novel condensed-ring thiophene derivatives and the salts thereof.

BACKGROUND ART

Secretion of anterior pituitary hormone undergoes the control by peripheral hormone secreted from target organs for the respective hormones and by secretion-accelerating or -inhibiting hormone from hypothalamus, which is the upper central organ of anterior lobe of pituitary (in this specification, these hormones are collectively called "hypothalamic hormone"). At the present stage, as hypothalamic hormones, nine kinds of hormones including, for example, thyrotropin releasing hormone (TRH) or gonadotropin releasing hormone {GnRH: sometimes called as LH-RH (luteinizing hormone releasing hormone)} are confirmed their existence (cf. Seirigaku 2, compiled by M. Iriku and K Toyama, published by Bunkohdo, p610–618, 1986). These hypothalamic hormones are assumed to show their actions via the receptor which is considered to exist in the anterior lobe of pituitary (cf. ibid), and observatinal studies of receptor genes specific to these hormones, including cases of human, have been developed (Receptor Kiso To Rinshô, compiled by H. Imura, et al., published by Asakura Shoten, p297–304, 1993). Accordingly, antagonists or agonists specifically and selectively acting on these receptors control the action of hypothalamic hormone and controlling the secretion of anterior pituitary hormone. As the results, they are expected to be useful for prophylactic and therapeutic agents of anterior pituitary hormone dependent diseases.

Leuprorelin acetate [Fujino et al., Biological and Biophysical Research Communications, Vol.60, 00.406–413, 1974); Oliver, R. T. D. et al., British Journal of Cancers, Vol.59, p.823, 1989; and Toguchi et al., Journal of International Medical Research, Vol.18, pp.35–41], which is a highly potent derivative of gonadotropic hormone-releasing hormone, one of the hypothalamic hormones, (hereinafter sometimes abbreviated as GnRH) [Schally A. V. et at., Journal of Biological Chemistry, Vol. 246, pp.7230–7236, 1971; and Burgus, R. et al., Proceeding of Natural Academic Science, USA, Vol.69, pp278–282, 1972], by administration of multiple doses, lowers release,production of gonadotropic hormone in pituitary, causing lowering of reactivity on gonadotropic hormone is spermary and ovary to suppress secretion of testosterone and estrogen. Leuprorelin acetate has, therefore, been known to show antitumor activity on such hormone-dependent cancers as exemplified by prostate cancer, and has been widely used in the clinical field. Leuprorelin acetate has been widely used clinically also as a therapeutic agent of e.g. endometriosis and precocious puberty. The high antitumor activity of leuprorelin acetate is assumed to be due to its high resistance, as compared with natural GnRH, against protease,and to high affinity to GnRH receptor causing desensitization of GnRH due to decrease in number of receptors. However, as leuprorelin acetate is an ultra-agonist on GnRH receptor, it has been known that, immediately after the first administration, a transient aggravation accompanied with the rise of serum testosterone concentration due to pituitary-gonadotropic action (acute action) is observed. Circumstances being such as above, GnRH antagonistic drugs which are expected to have substantially the same therapeutic effects as described above but not to cause the above-mentioned transient pituitary-gonadotropic action (acute action) have been desired. As compounds having such GnRH antagonistic activity, a number of compounds including, for example, derivatives of GnRH such as straight-chain peptides, (U.S. Pat. No. 5140009, 5171835), cyclic hexapeptide derivatives [JPA S61(1986)-191698] or bicyclic peptide derivatives [Journal of medicinal chemistry, Vol.36, pp.3265–3273, 1993]. These compounds are, however, all peptides, which leave many problems including, for example, dosage forms, stability of drugs, durability of actions and stability on metabolism. For solving these problems, orally administrable GnRH antagonistic drugs, especially non-peptide ones, are strongly desired. At the present stage, however, no report on non-peptide GnRH antagonistic drugs has been made.

The object of the invention lies in providing novel compounds having excellent gonadotropic hormone releasing hormone antagonistic activity as well as excellent gonadotropic hormone releasing hormone antagonistic agents.

DISCLOSURE OF INVENTION

Thus, the present invention provides a pharmaceutical composition for antagonizing a gonadotropin-releasing hormone (GnRH) containing a condensed-bicyclic compound consisting of a homo or hetero 5 to 7 membered ring and a homo or hetero 5 to 7 membered ring. The present invention also provides novel condensed-ring thiophene derivatives and salts thereof. The present invention further provides methods for manufacturing the novel condensed-ring thiophene derivatives and the salts thereof.

More specifically, the present invention provides:

(1) A compound of the formula (I):

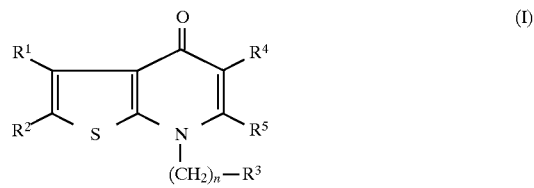

wherein $R^1$ and $R^2$ are each independently hydrogen or a group bonded through a carbon atom, an oxygen atom, a nitrogen atom or a sulfur atom;

$R^3$ is an optionally substituted homo- or hetero-cyclic group;

$R^4$ is hydrogen, formyl, cyano a lower alkyl group substituted by a group bonded through a sulfur atom or an optionally substituted hydroxyl group, a carbonyl group which may be substituted with an optionally substituted hydrocarbon residue, an esterified or amidated carboxyl group;

$R^5$ is hydrogen or a group bonded through a carbon atom;

n is 0 to 3;

with the proviso that the homo- or hetero-cyclic group shown by $R^3$ is not substituted by a group, which is described in EP-A-443568 and EP-A-520423, of the formula:

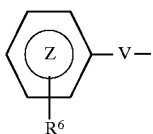

in which R⁶ is an optionally substituted 5 to 7 membered heterocyclic group having as a group capable of constituting the ring, carbonyl, thiocarbonyl, an optionally oxidized sulfur atom or a group convertible them, a group capable of forming an anion or a group convertible into an anion;

Z is an optionally substituted aromatic hydrocarbon residue optionally containing a hetero atom or an optionally substituted heterocyclic group;

V is a chemical bond or a spacer group, or a salt thereof,
(2) a compound according to (1), wherein R³ is a group of the formula:

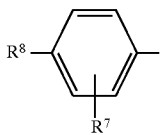

in which R⁷ is hydrogen, halogen or a group bonded through a carbon atom, a nitrogen atom, an oxygen atom or a sulfur atom;

R⁸ is hydrogen, halogen, nitro, cyano or a hydrocarbon residue which may be substituted by a group bonded through an oxygen atom, a nitrogen atom or a sulfur atom, (3) a compound according to (1), wherein either one of R¹ or R² is a group of the formula:

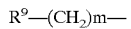

in which R⁹ is a group bonded through a nitrogen atom;
m is 0 to 3, and the other one is a group of the formula:

in which R¹⁰ is an optionally substituted phenyl; A is a chemical bond or a spacer group,
(4) a compound of the formula (II):

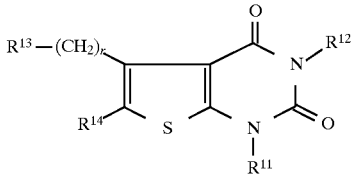

wherein R¹¹ is hydrogen, lower alkyl, a group of the formula:

in which Q is aryl which may be substituted by a) halogen, b) nitro, c) cyano, d) amino, e) an optionally substituted f) carboxyl, lower alkylenedioxy or g) a group of the formula: —A—R¹⁵ in which A is a chemical bond or a spacer group, R¹⁵ is alkyl, an optionally substituted cycloalkyl or an optionally substituted heterocyclic group;

R¹² is hydrogen, alkyl, an optionally substituted aryl, an optionally substituted aralkyl, an optionally substituted cycloalkyl; R¹³ is an optionally substituted amino,;

R¹⁴ is an optionally substituted aryl;
r is 0 to 3,
or a salt thereof,
(5) a compound according to (4), wherein R¹¹ is a group of the formula:

in which Q is aryl which may be substituted by a) halogen, b) nitro, c) cyano, d) amino, e) an optionally substituted f) carboxyl, lower alkylenedioxy or g) a group of the formula: —A—R¹⁵ in which A is a chemical bond or a spacer group, R¹⁵ is alkyl, (6) a compound according to (4), wherein Q is aryl which may be substituted by halogen, (7) a compound according to (4), wherein R¹³ is optionally substituted mono-aralkylamino, (8) a compound according to (4), wherein R¹³ is optionally substituted benzylamino, (9) a compound according to (4), wherein R¹⁴ is optionally substituted phenyl,

(10) a compound which is 3-(N-benzyl-N-methylaminomethyl)-4,7-dihydro-7-(2-methoxybenzyl)-2-(4-methoxyphenyl)-4-oxothieno[2,3-b]pyridine-5-carboxylic acid ethyl ester of its salt,

(11) a compound which is 3-(N-benzyl-N-methylaminomethyl)-4,7-dihydro-7-(2-fluorobenzyl)-2-(4-methoxyphenyl)-4-oxothieno[2,3-b]pyridine-5-carboxylic acid ethyl ester or its salt,

(12) a compound which is 2-(4-acetylaminophenyl)-3-(N-benzyl-N-methylaminomethyl)-4,7-dihydro-7-(2-fluorobenzyl)-4-oxothieno[2,3-b]pyridine-5-carboxylic acid ethyl ester or its salt,

(13) a compound which is 5-benzylaminomethyl-1-(2-chloro-6-fluorobenzyl)-2,4(1H,3H)-dioxo-6-(4-methoxyphenyl)-3-phenylthiion[2,3-d]pyrimidine or its salt,

(14) a compound which is 5-benzoyl-3-(N-benzyl-N-methylaminomethyl)-7-(2,6-difluorobenzyl)-4,7-dihydro-4-oxo-2-(4-propionylaminophenyl)thieno[2,3-b]pyridine or its salt,

(15) a compound which is 5-benzoyl-3-(N-benzyl-N-methylaminomethyl)-7-(2,6-difluorobenzyl)-4,7-dihydro-2-(4-N'-methylureidophenyl)-4-oxothieno[2,3-b]pyridine or its salt,

(16) a compound which is 3-(N-benzyl-N-methylaminomethyl)-7-(2,6-difluorobenzyl)-4,7-dihydro-5-isobutyryl-4-oxo-2-(4-propionylaminophenyl)-thieno[2,3-b]pyridine or its salt,

(17) a compound which is 3-(N-benzyl-N-methylaminomethyl)-7-(2,6-difluorobenzyl)-4,7-dihydro-5-isobutyryl-2-(4-N'-methylureidophenyl)-4-oxothieno[2,3-b] pyridine or its salt, (18) a compound which is 3-(N-benzyl-N-methylaminomethyl)-7-(2,6-difluorobenzyl)-4,7-dihydro-2-(4-N'-methylureidophenyl)-4-oxothieno[2,3-b]pyridine-5-(N-isopropyl)carboxamide or its salt,

(19) a compound which is 3-(N-benzyl-N-methylaminomethyl)-7-(2,6-difluorobenzyl)-4,7-dihydro-2-(4-N'-methylureidophenyl)-4-oxothieno[2,3-b]pyridine-5-(N-isopropyl-N-methyl)carboxamide or its salt,

(20) a compound which is 3-(N-benzyl-N-methylaminomethyl)-7-(2,6-difluorobenzyl)-4,7-dihydro-2-(4-N'-methylureidophenyl)-4-oxothieno[2,3-b]pyridine-5-(N-benzyl-N-methyl)carboxamide or its salt,

(21) a method for producing a compound of (3), which comprises reacting a compound of the formula (III):

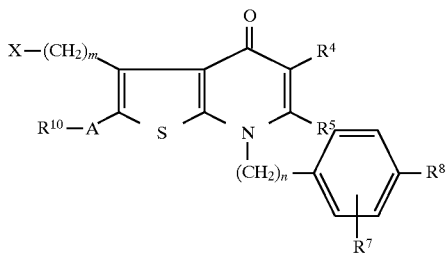

wherein $R^4$, $R^5$ and n are the same meaning as defined in (1);

$R^7$ and $R^8$ are the same meaning as defined in (2);

$R^{10}$ and m are the same meaning as defined in (3);

X is a leaving group; or a salt thereof, with a compound of the formula:

$R^9H$ wherein $R^9$ is the same meaning as defined in (3), or a salt thereof,

(22) a method for producing a compound of (5), which comprises reacting a compound of the formula (IV):

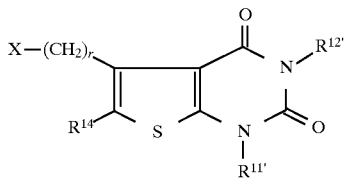

wherein $R^{11}$ is a group of the formula:

$Q-(CH_2)p-$ in which Q is aryl which may be substituted by a) halogen, b) nitro, c) cyamo, d) amino, e) an optionally substituted f) carboxyl, lower alkylenedioxy or g) a group of the formula: $-A-R^{15}$ in which A is a chemical bond or a spacer group, $R^{15}$ is alkyl;

$R^{12'}$, is alkyl, optionally substituted aryl, optionally substituted ararkyl or optionally substituted cycloalkyl;

$R^{14}$ and r are the same meaning as defined in claim 4;

X is a leaving group; or a salt thereof, with a compound of the formula:

$R^{13}H$ wherein $R^{13}$ is the same meaning as defined in (4), or a salt thereof,

(23) a gonadotropin-releasing hormone antagonistic composition, which comprises an optionally substituted condensed-bycyclic compound consisting of a homo or hetero 5 to 7 membered and a homo or hetero 5 to 7 membered ring; carrier; excipient or diluent,

(24) a composition according to (23), wherein the optionally-substituted condensed-bicyclic compound is a compound of the formula (IV):

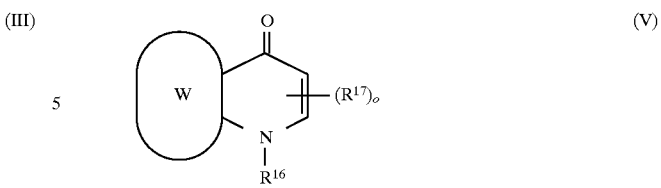

in which a ring W is an optionally substituted homo or hetero 5 to 7 membered ring;

$R^{16}$ is an optionally substituted hydrocarbone residue;

$R^{17}$ is hydrogen, or a group bonded through a carbon atom, a nitrogen atom, oxygen atom or sulfur atom;

o is 1 or 2,

(25) a composition according to (24), wherein the ring W is a ring the formula (VI):

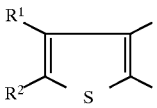

in which $R^1$ and $R^2$ are each independently hydrogen, or a group bonded through a carbon atom, a nitrogen atom, oxygen atom or a sulfur atom,

(26) a composition according to (23), wherein the optionally substituted condensed-bicyclic compound is a compound of the formula (VII):

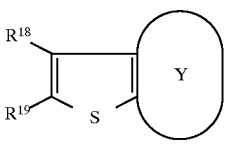

in which a ring Y is an optionally substituted hetero 5 to 7 membered ring;

$R^{18}$ and $R^{19}$ are each independently an optionally substituted hydrocarbon residue,

(27) a composition according to (26), wherein the ring Y is a ring of the formula (VIII):

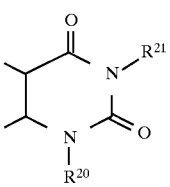

in which $R^{20}$ and $R^{21}$ are each independently hydrogen, an optionally substituted hydrocarbon residue,

(28) a composition according to (23), which is a composition for preventing or treating a sex hormone dependent disease,

(29) a composition according to (23), which is a composition for preventing or treating a sex hormone dependent cancer, benign prostatic hypertrophy or myoma of the uterus,

(30) a composition according to (29), wherein the sex hormone dependent cancer is selected from the group consisting of prostatic cancer, uterus cancer, breast cancer and pitutiary adenoma,

(31) a composition according to (28), wherein the sex hormone depending disease is selected from the group consistion of prostatauxe, endometriosis, myoma uteri and precocious puberty,

(32) a pregnancy controlling composition, which comprises a compound or a salt thereof claimed in (23), carrier, excipient or diluent,

(33) a menstrual cycle controlling composition, which comprises a compound or a salt thereof claimed in (23), carrier, excipient or diluent, and

(34) a composition according to (32), which is a composition for contraception,

(35) a method for antagonizing gonadotropin-releasing hormone in a mammal in need thereof comprising administering an effective amount of a composition according to (23) to a mammal suffering from a gonadotropin-releasing hormone derived disorder,

(36) a method according to (35), wherein the gonadotropin-releasing hormone derived disorder is a sex hormone dependent disease,

(37) a method according to (35), wherein the gonadotropin-releasing hormone derived disorder is a sex hormone dependent cancer, benign prostatic hypertropy or myoma of the uterus,

(38) a method according to (37), wherein the sex hormone dependent cancer is selected from the group consisting of prostatic cancer, uterus cancer, breast cancer and pituitary adenoma,

(39) a method according to (36), wherein the sex hormone depending disease is selected from the group consisting of prostatauxe, endometriosis, myoma uteri and precocious puberty,

(40) a method for controlling pregnancy in a mammal in need thereof comprising administering an effective amount of a composition according to (23),

(41) a method for controlling menstrual cycle in a mammal in need thereof comprising administering an effective amount of a composition according to (23),

(42) a method for contraception in a mammal in need thereof comprising administering an effective amount of a composition according to (23),

(43) a use of an optionally substituted condensed-bicyclic compound consisting of a homo or hetero 5 to 7 membered ring and a homo or hetero 5 to 7 membered ring for producing a gonadotropin-releasing hormone antagonistic composition for antagonizing gonadotropin releasing hormone in a mammal suffering from a gonadotropin-releasing hormone derived disorder,

(44) a use according to (43), wherein the gonadotropin-releasing hormone derived disorder is a sex hormone dependent disease,

(45) a use according to (43), wherein the gonadotropin-releasing hormone derived disorder is a sex hormone dependent cancer, benign prostatic hypertropy or myoma of the uterus,

(46) a use according to (45), wherein the sex hormone dependent cancer is selected from the group consisting of prostatic cancer, uterus cancer, breast cancer and pututiary adenoma,

(47) a use according to (45), wherein the sex hormone depending disease is selected from the group consisting of prostatauxe, endometriosis, myoma uteri and precocious puberty,

(48) a use of an optionally substituted condensed-bicyclic compound consisting of a homo or hetero 5 to 7 membered ring and a homo or hetero 5 to 7 membered ring for producing a gonadotropin-releasing hormone antagonistic composition for controlling pregnancy in a mammal in need thereof,

(49) a use of an optionally substituted condensed-bicyclic compound consisting of a homo or hetero 5 to 7 membered ring and a homo or hetero 5 to 7 membered ring for producing a gonadotropin-releasing hormone antagonistic composition for controlling menstrual cycle in a mammal in need thereof, and

(50) a use of an optionally substituted condensed-bicyclic compound consisting of a homo or hetero 5 to 7 membered ring and a homo or hetero 5 to 7 membered ring for producing a gonadotropin-releasing hormone antagonistic composition for contraception in a mammal in need thereof.

Examples of the groups bonded through the carbon atom shown by $R^1$, $R^2$, $R^5$ and $R^7$, include, each optionally substituted, alkyl (e.g. $C_{1-6}$ alkyl such as methyl, ethyl, propyl, isopropyl, butyl, t-butyl, pentyl and hexyl), cycloalkyl (e.g. $C_{3-6}$ cycloalkyl such as cyclopropyl, cyclopentyl and cyclohexyl), alkoxyalkyl (e.g. $C_{1-3}$ alkoxy-$C_{1-6}$ alkyl such as methoxymethyl, ethoxymethyl, ethoxybutyl and propoxyhexyl), hydroxyalkyl (e.g. $C_{1-6}$ alkyl such as hydroxymethyl, hydroxyethyl, hydroxybutyl and hydroxypropyl), alkenyl (e.g. $C_{2-6}$ alkenyl such as vinyl, butadienyl and hexatrienyl), formyl, carboxyl, alkoxycarbonyl (e.g. $C_{1-6}$ alkoxycarbonyl such as methoxycarbonyl, ethoxycarbonyl and t-butoxycarbonyl), cyano, amido, mono-, di-alkylcarbamoyl (e.g. mono-, di-$C_{1-6}$ alkylcarbamoyl such as methyl carbamoyl, ethylcarbamoyl, hexylcarbamoyl, dimethylcarbamoyl and methylethylcarbamoyl), amidino, aryl (e.g. $C_{6-14}$ aryl such as phenyl, naphthyl and anthracenyl), aralkyl (e.g. $C_{7-20}$ aralkyl such as benzyl, benzhydryl and trityl) and heterocyclic groups having a bond at the carbon atom (e.g. 5-membered cyclic groups containing, besides the carbon atom, 1 to 4 hetero-atoms selected from oxygen atom, sulfur atom and nitrogen atom, such as 2- or 3-thienyl, 2- or 3-furyl, 2- or 3-pyrrolyl, 2-, 3- or 4-pyridyl, 2-, 4- or 5-oxazolyl, 2-, 4- or 5-thiazolyl, 3-, 4- or 5-pyrazolyl, 2-, 4- or 5-imidazolyl, 3-, 4-or 5-isoxazolyl, 3, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl and 1H- or 2H-tetrazolyl; 6-membered cyclic groups containing, besides the carbon atom, 1 to 4 hetero-atoms selected from oxygen atom, sulfur atom and nitrogen atom, such as N-oxido-2-, 3- or 4-pyridyl, 2-, 4-or 5-pyrimidinyl, N-oxido-2-, 4- or 5-pyrimidinyl, 2- or 3-thiomorpholinyl, 2- or 3-morpholinyl, oxoimidazinyl, dioxotriazinyl, pyrrolidinyl, piperidinyl, pyranyl, thiopyranyl, 1,4-oxadinyl, 1,4-thiazinyl, 1,3-thiazinyl, 2- or 3-piperazinyl, triazinyl, oxotriazinyl, 3- or 4-pyridazinyl, pyrazinyl and N-oxido-3- or 4-pyridazinyl; and 5- to 8-membered cyclic groups or condensed ring thereof containing, besides the carbon atom, 1 to 4 hetero-atoms e.g. oxygen atom, sulfur atom or nitrogen atom, for example, bicyclic or tricyclic condensed cyclic groups containing, besides the carbon atom, 1 to 4 hetero-atoms selected from oxygen atom, sulfur atom and nitrogen atom, such as benzofuryl, benzothiazolyl, benzoxazolyl, tetrazolo[1,5-b]pyridazinyl, triazolo[4,5-b]pyridazinyl, benzoimidazolyl, quinolyl, isoquinolinyl, cinnolinyl, phthalazinyl, quinazolinyl, quinoxalinyl, indolizinyl, quinolizinyl, 1,8-naphthylizinyl, purinyl, pteridinyl, dibenzofuranyl, carbazolyl, acrydinyl, phenanthridinyl, chromanyl, benzoxazinyl, phenazinyl, phenothiazinyl and phenoxazinyl).

Examples of the substituents, which the above-mentioned groups bonded through the carbon atom may have, include $C_{6-14}$ aryl (e.g. phenyl and naphthyl) optionally substituted with 1 to 4 substituents selected from, for example, (a) hydroxyl, (b) amino, (c) mono- or di- $C_{1-6}$ alkyl amino (e.g. methylamino, ethylamino, propylamino, propylamino, dimethylamino and diethylamino) and (d) $C_{1-6}$ alkoxy (e.g. methoxy, ethoxy, propoxy and hexyloxy) and (e) halogen (fluorine, chlorine, bromine, iodine); mono- or di- $C_{1-6}$ alkylamino (e.g. methylamino, ethylamino, propylamino, dimethylamino and diethylamino); $C_{1-4}$ acylamino (e.g. formylamino and acetylamino); hydroxyl; carboxyl; nitro; $C_{1-6}$ alkoxy (e.g. methoxy, ethoxy, propoxy, isopropoxy and butoxy); $C_{1-6}$ alkyl-carbonyloxy (e.g. acetoxy and ethyl carbonyloxy)), halogen (e.g. fluorine, chlorine, bromine and iodine), and such optionally substituted groups bonded through nitrogen atom as described below. Number of the substituents ranges from 1 to 6, preferably 1 to 3.

Examples of the groups bonded through nitrogen atom shown by $R^1$, $R^2$, $R^7$, $R^9$ and $R^{17}$, include, each optionally substituted, groups shown by $$-NR^{22}R^{23}$$

wherein $R^{22}$ is hydrogen, alkyl, cycloalkyl, aryl, heterocyclic groups and —SOp—(p is 1 to 2) and $R^{14}$ is hydrogen or alkyl, and heterocyclic groups bonded through a nitrogen atom (e.g. 1H-1-pyrrolyl, 1-imidazolyl, pyrazolyl, indolyl, 1H-1-indazolyl, 7-purinyl, 1-pyrrolidinyl, 1-pyrrolinyl, 1-imidazolidinyl, pyrazolidinyl, piperazinyl, pyrazolidinyl, 4-morpholinyl and 4-thiomorpholinyl). Said alkyl, cycloalkyl, aryl and a heterocyclic group are the same meaning as described in the above.

Examples of the substituents, which the group bonded through nitrogen atom may have, include $C_{1-6}$ alkyl (e.g. methyl, ethyl, propyl, isopropyl, butyl, isobutyl, sec-butyl and tert-butyl), $C_{2-6}$ alkenyl (e.g. vinyl, 1-methylvinyl, 1-propenyl and allyl), $C_{2-6}$ alkynyl (e.g. ethynyl, 1-propynyl and propargyl), $C_{3-6}$ cycloalkyl (e.g. cyclopropyl, cyclobutyl, cyclopentyl and cyclohexyl), $C_{5-7}$ cycloalkenyl (e.g. cyclopentenyl and cyclohexenyl), $C_{7-11}$ aralkyl (e.g. benzyl, α-methylbenzyl and phenethyl), $C_{6-14}$ aryl (e.g. phenyl and naphthyl), $C_{1-6}$ alkoxy (e.g. methoxy, ethoxy, propoxy, isopropoxy, n-butoxy, isobutoxy, sec-butoxy and tert-butoxy), $C_{6-14}$ aryloxy (e.g. phenoxy), $C_{1-6}$ alkanoyl (e.g. formyl, acetyl, propionyl, n-butyryl and isobutyryl), $C_{6-14}$ aryl-carbonyl (e.g. benzoyl), $C_{1-6}$ alaknoyloxy (e.g. formyloxy, acetyloxy, propionyloxy and iso-butyryloxy), $C_{6-14}$ aryl-carbonyloxy (e.g. benzoyloxy), carboxyl, $C_{1-6}$ alkoxy-carbonyl (e.g. methoxycarbonyl, ethoxycarbonyl, n-propoxycarbonyl, iso-propoxycarbonyl, n-butoxycarbonyl, isobutoxycarbonyl and tert-butoxycarbonyl), carbamoyl group, N-mono- $C_{1-4}$ alkylcarbamoyl (e.g. N-methylcarbamoyl, N-ethylcarbamoyl, N-propylcarbamoyl, N-isopropylcarbamoyl and N-butylcarbamoyl), N,N-di- $C_{1-4}$ alkylcarbamoyl (e.g. N,N-di methylcarbamoyl, N,N-diethylcarbamoyl, N,N-dipropylcarbamoyl and N,N-dibutylcarbamoyl), cyclic aminocarbonyl (e.g. 1-aziridinylcarbonyl, 1-azetidinylcarbonyl, 1-pyrrolidinylcarbonyl, 1-piperidinylcarbonyl, N-methylpiperazinylcarbonyl and morpholinocarbonyl), halogen (fluorine, chlorine, bromine and iodine), mono-or tri-halogeno- $C_{1-4}$ alkyl (e.g. chloromethyl, dichloromethyl, trifluoromethyl and trifluoroethyl), oxo group, amidino, imino group, amino, mono- or di $C_{1-4}$ alkylamino (e.g. methylamino, ethylamino, propylamino, isopropylamino, butylamino, dimethylamino, diethylamino, dipropylamino, diisoopropylamino and dibutylamino), 3- to 6-membered cyclic amino group containing, besides the carbon atom and one nitrogen atom, 1 to 3 hetero-atoms selected from oxygen atom, sulfur atom and nitrogen atom (e.g. aziridinyl, azetidinyl, pyrrolidinyl, pyrrolinyl, pyrrolyl, imidazolyl, pyrazolyl, imidazolidinyl, piperidino, morpholino, dihydropyridyl, N-methylpiperazinyl and N-ethylpiperazinyl), $C_{1-6}$ alkanoylamino (e.g. formamide, acetamide, trifluoroacetamide, propionylamindo, butyrylamido and isobutyrylamido), benzamido, carbamoylamino, N- $C_{1-4}$ alkylcarbamoylamino (e.g. N-methylcarbamoylamino), N-ethylcarbamoylamino, N-propylcarbamoylamino, N-isopropylcarbamoylamino and N-butylcarbamoylamino), N,N-di- $C_{1-4}$ alkylcarbamoylamino (e.g. N,N-dimethylcarbamoylamino, N,N-diethylcarbamoylamino, N,N-dipropylcarbamoylamino and N,N-dibutylcarbamoylamino), $C_{1-3}$ alkylenedioxy (e.g. methylenedioxy and ethylenedioxy), —B(OH)$_2$, hydroxyl, epoxy (—O—), nitro, cyano, mercapto, sulfo, sulfino, phosphono, dihydroxyboryl, sulfamoyl, $C_{1-6}$ alkylsulfamoyl, (e.g. N-methylsulfamoyl, N-ethylsulfamoyl, N-propylsulfamoyl, N-isopropylsulfamoyl and N-butyl sulfamoyl), di- $C_{1-6}$ alkylsulfamoyl (e.g. N,N-dimethylsulfamoyl, N,N-diethylsulfamoyl, N,N-dipropylsulfamoyl and N,N-dibutylsulfamoyl), $C_{1-6}$ alkylthio (e.g. methylthio, ethylthio, propylthio, isopropylthio, n-butylthio, sec-butylthio and tert-butylthio), phenylthio, $C_{1-6}$ alkylsulfinyl (e.g. methylsulfinyl, ethylsulfinyl, propylsulfinyl and butylsulfinyl), phenylsulfinyl, $C_{1-6}$ alkylsulfonyl (e.g. methylsulfonyl, ethylsulfonyl, propylsulfonyl and butylsulfonyl), and phenylsulfonyl. The number of the substituents ranges from 1 to 6, preferably 1 to 3.

Examples of the groups bonded through oxygen atom shown by $R^1$, $R^2$ and $R^7$, include hydroxyl, each optionally substituted, alkoxyl, cycloalkoxy, aryloxy, aralkyloxy and heterocyclic hydroxyl groups. The alkyl, cyloalkyl, aryl, aralkyl and heterocyclic groups, in the said alkoxy, cycloalkoxy, aryloxy, aralkyloxy and heterocyclic hydroxyl groups, are of the same meaning as above.

The substituents, which the said oxygen atom may have, are of the same meaning as that of the above-mentioned groups bonded through nitrogen atom.

Examples of the groups bonded through sulfur atom, shown by $R^1$, $R^2$, $R^7$ and $R^{12}$, include mercapto, alkylthio, cycloalkylthio, arylthio, aralkylthio and heterocyclic thio groups. The alkyl, cycloalkyl, aryl, aralkyl and heterocyclic groups, in the said alkylthio, cycloalkylthio, arylthio, aralkylthio and heterocyclic thio groups, are of the same meaning as defined above.

The substituents, which the said sulfur atom may have, are of the same meaning as that of the substituents which the above-mentioned optionally substituted groups bonded through nitrogen atom may have.

Examples homocyclic groups in the optionally substituted homocyclic groups shown by $R^3$ include 3- to 7-membered cyclic hydrocarbon groups consisting of only carbon atoms, for example, $C_{3-7}$ cycloalkane (e.g. cyclopropane, cyclobutane, cyclopentane, cyclohexane and cycloheptane) and $C_{-7}$ cycloalkene (e.g. cyclopropene, cyclobutene, cyclopentene, cyclohexene and cycloheptene).

Examples of the substituents which the said homocyclic groups may have, include $C_{1-15}$ alkyl (e.g. methyl, ethyl, propyl, isopropyl, butyl, isobutyl, s-butyl, t-butyl, pentyl, hexyl, heptyl, octyl, nonyl, decyl, undecyl, dodecyl, tridecyl, tetradecyl and pentadecyl), $C_{3-10}$ cycloalkyl (e.g. cyclopropyl, cyclobutyl, cyclopentyl and cyclohexyl), $C_{2-10}$ alkenyl (e.g. vinyl, allyl, 2-methylallyl, 2-butenyl, 3-butenyl and 3-octenyl), $C_{2-10}$ alkynyl (e.g. ethynyl, 2-propynyl and 3-hexynyl), $C_{3-10}$ cycloalkyl (e.g. cyclopropenyl, cyclopentenyl and cyclohexenyl), $C_{6-10}$ aryl (e.g. phenyl and naphthyl), $C_{1-19}$ aralkyl, (e.g. benzyl, phenylethyl and trityl), nitro, hydroxyl, mercapto, oxo, thioxo, cyano, carbamoyl, carboxyl, $C_{1-5}$ alkoxy-carbonyl (e.g. methoxycarbonyl and ethoxycarbonyl), sulfo, halogen (e.g. fluorine, chlorine, bromine and iodine), $C_{1-6}$ alkoxy (e.g. methoxy, ethoxy, propoxy, isopropoxy, butoxy, isobutoxy, s-butoxy and t-butoxy), $C_{6-10}$ aryloxy (e.g. phenoxy), $C_{1-6}$ alkylthio (e.g. methylthio, ethylthio, n-propylthio, isopropylthio, n-butylthio and t-butylthio), $C_{6-10}$ arylthio (e.g. phenylthio), $C_{1-6}$ alkylsulfinyl (e.g. methylsulfinyl and ethylsulfinyl), $C_{6-10}$ arylsulfinyl (e.g.phenylsulfinyl), $C_{1-6}$ alkylsulfonyl (e.g. methylsulfonyl and ethylsulfonyl), $C_{6-10}$ arylsulfonyl (e.g. phenylsulfonyl), amino, $C_{1-6}$ acylamino (e.g. acetylamino and propylamino), mono- or di- $C_{1-4}$ alkylamino (e.g. methylamino, ethylamino, n-propylamino, isopropylamino, n-butylamino, dimethylamino and diethylamino), $C_{3-8}$ cycloalkylamino (e.g. cyclopropylamino, cyclobutylamino, cyclopentylamino and cyclohexylamino), $C_{6-10}$ arylamino (e.g. anilino), $C_{1-6}$ aralkyl (e.g. formyl, acetyl and hexanoyl), $C_{6-10}$ arylcarbonyl (e.g. benzoyl), and 5- to 6-membered heterocyclic group containing, besides carbon atom, 1 to 4 hetero-atoms selected from oxygen, sulfur and nitrogen (e.g. 2- or 3-thienyl, 2- or 3-furyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H or 2H-tetrazolyl, 2-, 3- or 4-pyridyl, 2-, 4- or 5-pyrimidyl, 3- or 4-pyridazinyl, quinolyl, isoquinolyl and indolyl). Number the substituents ranges from 1 to 6, preferably from 1 to 3.

Examples of the above-mentioned optionally substituted heterocyclic groups shown by $R^3$ include 5-to 8-membered cyclic groups or condensed ring thereof containing, besides carbon atom, 1 to 4 hetero-atoms such as oxygen atom, sulfur atom and nitrogen atom, for example, 5-membered cyclic groups containing, besides carbon atom, 1 to 4 hetero-atoms selected from oxygen atom, sulfur atom and nitrogen atom, as exemplified by 2- or 3-thienyl, 2- or 3-furyl, 2- or 3-pyrrolyl, 2-, 3- or 4-pyridyl, 2-, 4- or 5-oxazolyl, 2-, 4- or 5-thiazolyl, 3-, 4- or 5-pyrazolyl, 2-, 4- or 5-imidazolyl, 3, 4- or 5-isoxazolyl, 3-, 4- or 5-isothiazolyl, 3- or 5-(1,2,4-oxadiazolyl), 1,3,4-oxazolyl, 3- or 5-(1,2,4-thiadiazolyl), 1,3,4-thiadiazolyl, 4- or 5-(1,2,3-thiadiazolyl), 1,2,5-thiadiazolyl, 1,2,5-thiadiazolyl, 1,2,3-triazolyl, 1,2,4-triazolyl, and 1H- or 2H-tetrazolyl; 6-membered cyclic groups containing, besides, carbon atom, 1 to 4 hetero-atoms selected from oxygen atom, sulfur atom and nitrogen atom, as exemplified by N-oxido-2-, 3- or 4-pyridyl, 2-, 4- or 5-pyrimidinyl, N-oxido-2-, 4-or 5-pyrimidinyl, thiomorpholinyl, morpholinyl, oxoimidazinyl, dioxotriazinyl, pyrrolidinyl, piperazinyl, pyranyl, thiopyranyl, 1,4-oxadinyl, 1,4-thiazinyl, 1,3-thiazinyl, piperazinyl, triazinyl, oxotriazinyl, 3- or 4-pyridazinyl, pyrazinyl and N-oxido-3- or 4-pyridazinyl; bicyclic or tricyclic condensed ring groups containing, besides carbon atom, 1 to 4 hetero-atoms selected from oxygen atom, sulfur atom and nitrogen atom, as exemplified by benzofuryl, benzothiazolyl, benzoxazolyl, tetrazolo[1,4-b]pyridazinyl, triazolo[4,5-b]pyridazinyl, benzoimidazolyl, quinolyl, isoquinolyl, cinnolinyl, phthaladinyl, quinazolinyl, quinoxalinyl, indolidinyl, quinolidinyl, 1,8-napthylidinyl, purinyl, pteridinyl, dibenzofuranyl, carbazolyl, acridinyl, phenathridinyl, chromanyl, benzoxadinyl, phenazinyl, phenothiazinyl and phenoxazinyl.

Examples of substituents, which said heterocyclic groups may have, $C_{1-6}$ alkyl (e.g. methyl,ethyl, propyl, isopropyl, butyl, isobutyl, sec-butyl and tert-butyl), $C_{2-6}$ alkenyl (e.g. vinyl, 1-methylvinyl, 1-propenyl and allyl), $C_{2-6}$ alkynyl (e.g. ethynyl, 1-propinyl and propargyl), $C_{3-6}$ cycloalkyl (e.g. cyclopropyl, cyclobutyl, cyclopentyl) and cyclohexyl), $C_{5-7}$ cycloalkenyl (e.g. cyclopentenyl and cyclohexenyl), $C_{7-11}$ aralkyl (e.g. benzyl, α-methylbenzyl and phenethyl), $C_{6-14}$ aryl (e.g. phenyl and naphthyl), $C_{1-6}$ alkoxy (e.g. methoxy, ethoxy, propoxy, iso-propoxy, n-butoxy, iso-butoxy, sec-butoxy and tert-butoxy), $C_{6-14}$ aryloxy (e.g. phenoxy), $C_{1-6}$ alkanoyl (e.g. formyl, acetyl, propionyl, n-butyryl and iso-butyryl), $C_{6-14}$ aryl-carbonyl (e.g. benzoyl), $C_{1-6}$ alkanoyloxy (e.g. formyloxy, acetyloxy, propionyloxy, n-butyryloxy and isobutyryloxy), $C_{6-14}$ arylcarbonyloxy (e.g. benzoyloxy), carboxyl, $C_{1-6}$ alkoxycarbonyl (e.g. methoxycarbonyl, ethoxycarbonyl, n-propoxycarbonyl, iso-propoxycarbonyl, n-butoxycarbonyl, isobutoxycarbonyl and tert-butoxycarbonyl), carbamoyl group, N-mono- $C_{1-4}$ alkylcarbamoyl (e.g. N-methylcarbamoyl, N-ethylcarbamoyl, N-propylcarbamoyl, N-isopropylcarbamoyl and N-butylcarbamoyl), N,N-di- $C_{1-4}$ alkylcarbamoyl (e.g. N,N-dimethylcarbamoyl, N,N-diethylcarbamoyl, N,N-dipropylcarbamoyl and N,N-dibutylcarbamoyl), cyclic aminocarbonyl (e.g. 1-aziridinylcarbonyl, 1-azetidinylcarbonyl, 1-pyrrolidinylcarbonyl, 1-piperidinylcarbonyl, N-methylpiperazinylcarbonyl and morpholinocrbonyl), halogen (fluorine, chlorine, bromine, iodine), mono-,di or tri-halogeno $C_{1-4}$ alkyl (e.g. chloromethyl, dichloromethyl, trifluoromethyl and trifluoroethyl), oxo group,amidino, imino group, amino, mono- or di- $C_{1-4}$ alkylamino (e.g. methylamino, ethylamino, propylamino, isopropylamino, butylamino, dimethylamino, diethylamino, dipropylamino, diisopropylamino and dibutylamino), 3- to 6-membered cyclic amino group optionally containing, besides carbon atoms and one nitrogen atom, 1 to 3 hetero-atoms selected from oxygen atom, sulfur atom and nitrogen atom (e.g. aziridinyl, azetidinyl, pyrrolidinyl, pyrrolinyl, pyrrolyl, imidazolyl, pyrazolyl, imidazolidinyl, piperidino, morpholino, dihydropyridyl, pyridyl, N-methylpiperazinyl and N-ethylpiperazinyl), $C_{1-6}$ alkanoylamino (e.g. formamido, acetamido, trifluoroacetamido, propionylamido, butylamido and isobutyrylamido), benzamide, carbamoylamino, N- $C_{1-4}$ alkylcarbamoylamino (e.g. N-methylcarbamoylamino, N-ethylcarbamoylamino, N-propylcarbamoylamino, N-isopropylcarbamoylamino and N-butylcarbamoylamino), N,N-di- $C_{1-4}$ alkylcarbamoylamino (e.g. N,N-dimethylcarbamoylamino, N,N-diethylcarbamoylamino, N,N-dipropylcarbamoylamino and N,N-dibutylcarbamoylamino), $C_{1-3}$ alkylenedioxy (e.g. methylenedioxy and ethylenedioxy), —B(OH)2, hydroxyl, epoxy (—O—), nitro, cyano, mercapto, sulfo, sulfino, phosphono, dihydroxyboryl, sulfamoyl, $C_{1-6}$ alkylsulfamoyl (e.g. N-methylsulfamoyl, N-ethylsulfamoyl, N-propylsulfamoyl, N-isopropylsulfamoyl and N-butylsulfamoyl), di- $C_{1-6}$ alkylsulfamoyl (e.g. N,N-dimethylsulfamoyl, N,N-diethylsulfamoyl, N,N-dipropylsulfamoyl and N,N-dibutylsulfamoyl), $C_{1-6}$ alkylthio (e.g. methylthio, ethylthio, propylthio, isopropylthio, n-butylthio, sec-butylthio and tert-butylthio), phenylthio, $C_{1-6}$ alkylsulfinyl (e.g. methylsulfinyl, ethylsulfinyl, propylsulfinyl and butylsulfinyl), phenylsulfinyl, $C_{1-6}$ alkylsulfonyl (e.g. methylsulfonyl, ethylsulfonyl, propylsulfonyl and butylsulfonyl) and phenylsulfonyl. Number of the substituents ranges from 1 to 6, preferably 1 to 3.

As the ester group in the optionally esterified carboxyl group shown by $R^4$, mention is made of, for example, alkyl, cycloalkyl, aryl and heterocyclic groups, and these are of the same meaning as defined above.

Examples of the amidated carboxyl groups shown by $R^4$ include groups shown by —$CONR^{22}R^{23}$ (wherein $R^{22}$ and $R^{23}$ are of the same meaning as defined above).

As the lower alkyl in the lower alkyl substituted by a group bonded through a sulfur atom shown by $R^4$, mentioned is made of, for example, $C_{1-6}$ alkyl such as methyl, ethyl, propyl, i-propyl, butyl, i-butyl, s-butyl, pentyl, hexyl and the like. The group bonded through a sulfur atom is as the same meaning as defined above.

The lower alkyl in the lower alkyl substituted by an optionally substituted hydroxyl shown by $R^4$ is the same meaning as defined above.

As substituents on the lower alkyl group, having optionally substituted hydroxyl, shown by the above-mentioned $R^4$, use is made of, for example, $C_{1-6}$ alkyl (e.g. methyl, ethyl, n-propyl, i-propyl, n-butyl and tert-butyl) optionally having 1 to 4 substituents selected from halogen (e.g. chlorine, bromine and fluorine), $C_{6-10}$ aryl (e.g. phenyl and naphthyl), $C_{7-12}$ aralkyl (e.g. benzyl and phenylethyl) and nitro; $C_{6-10}$ aryl (e.g. phenyl and naphthyl) optionally having 1 to 4 substituents selected from halogen (e.g. chlorine, bromine and fluorine), $C_{1-6}$ alkyl (e.g. methyl, ethyl and n-propyl), $C_{1-10}$ aryl (e.g. phenyl and naphthyl); $C_{7-12}$ aralkyl (e.g. benzyl, phenylethyl and naphtylmethyl) optionally having 1 to 4 substituents selected from halogen, (e.g. chlorine, bromine and fluorine), $C_{1-6}$ alkyl (e.g. methyl, ethyl and n-propyl), $C_{6-10}$ aryl (e.g. phenyl and naphthyl), $C_{7-12}$ aralkyl (e.g. benzyl and phenethyl) and nitro; $C_{1-6}$ alkyl-carbonyl (e.g. acetyl and propionyl) optionally having 1 to 3 substituents selected from formyl, halogen (e.g. chlorine, bromine and fluorine), $C_{1-6}$ alkyl (e.g. methyl, ethyl and n-propyl), $C_{6-10}$ aryl(e.g. phenyl and naphthyl), $C_{7-12}$ aralkyl (e.g. benzyl and phenylethyl) and nitro; $C_{6-10}$ aryloxy-carbonyl (e.g. phenyloxycarbonyl and naphthyloxycarbonyl) optionally having 1 to 4 substituents selected from halogen (e.g. chlorine, bromine and fluorine), $C_{1-6}$ alkyl (e.g. methyl, ethyl and n-propyl), $C_{6-10}$ aryl(e.g. phenyl and naphthyl), $C_{7-12}$ aralkyl (e.g. benzyl and phenylethyl)and nitro; $C_{6-10}$ aryl-carbonyl (e.g. benzoyl and naphthylcarbonyl) optionally having 1 to 4 substituents selected from halogen (e.g. chlorine, bromine and fluorine), $C_{1-6}$ alkyl (e.g. methyl, ethyl and n-propyl), $C_{6-10}$ aryl (e.g. phenyl and naphthyl), $C_{7-12}$ aralkyl (e.g. benzyl and phenylethyl) and nitro; $C_{7-12}$ aralkyl-carbonyl (e.g. benzylcarbonyl and phenethylcarbonyl) optionally having 1 to 4 substituents selected from halogen (e.g. chlorine, bromine and fluorine), $C_{1-6}$ alkyl (e.g. methyl, ethyl and n-propyl), $C_{6-10}$ aryl (e.g. phenyl and naphthyl), $C_{7-12}$ aralkyl (e.g. benzyl and phenethyl) and nitro; and pyranyl or furanyl, tri ($C_{1-4}$ alkyl) silyl (e.g. trimethylsilyl and triethylsilyl) optionally having 1 to 4 substituents selected from halogen (e.g. chlorine, bromine and fluorine), $C_{1-6}$ alkyl (e.g. methyl, ethyl and n-propyl), $C_{6-10}$ aryl (e.g. phenyl and naphthyl), $C_{7-12}$ aralkyl (e.g. benzyl and phenethyl) ahd nitro.

As the hydrocarbon residue in the carbonyl group optionally substituted by the hydrocarbon residue, shown by $R^4$, mention is made of, for example, saturated or unsaturated hydrocarbon residues having up to 25 carbon atoms. Examples of them include alkyl (e.g. $C_{1-8}$ alkyl such as methyl, ethyl, propyl, isopropyl, butyl, t-butyl, pentyl and hexyl), cycloalkyl (e.g. $C_{3-6}$ cycloalkyl such as cyclopropyl, cyclobutyl and cyclohexyl), alkoxyalkyl (e.g. $C_{1-3}$ alkoxy-$C_{1-6}$ alkyl such as methoxymethyl, ethoxymethyl, ethoxybutyl and propoxyhexyl), alkenyl (e.g. $C_{2-6}$ alkenyl such as vinyl,butenyl, butadienyl and hexatrienyl), aryl (e.g. $C_{6-14}$ aryl such as phenyl, naphthyl and antracenyl) and aralkyl (e.g. $C_{7-20}$ aralkyl such as benzyl, benzhydrile and trityl).

The optionally substituted 5 to 7 membered heterocyclic group having as a group capable of constituting the ring, carbonyl, thiocarbonyl, an optionally oxidized sulfur atom or a group convertible them, shown by $R^6$, in the same meaning as defined on page 5, line 45 to page 9, line 35 of EP-A-0520423.

Examples of the anion-forming groups or groups convertible to amino, shown by the above-mentioned $R^6$, include carboxyl, $C_{1-4}$ alkoxycarbonyl, cyano, tetrazolyl, trifluoromethanesulfonic acid amido, phosphoric acid group and sulfonic acid group. As the spacer group shown by V, mention is made of, for example, —(C=O)—, —O—, —S—, —NH—,—(C=O)—NH—, —O—CH$_2$—, —S—CH$_2$— and —CH=CH—.

The optionally substituted aromatic hydrocarbon residue optionally containing a hetero atom and the optionally substituted heterocyclic group, shown by the ring Z, is the same meaning as defined on page 5, lines 38 to 44 of EP-A-0520423.

As the aryl shown by $R^{11}$ or in the optionally substituted aryl shown by $R^{12}$ and $R^{14}$, mention is made of, for example, mono cyclic- or condensed polycyclic-aromatic hydrocarbon residues. Preferable example of them includes $C_{6-14}$ aryl such as phenyl, naphthyl, anthryl, phenanthryl, acenaphthylenyl and the like. Among these, phenyl, 1-naphthyl and 2-naphthyl are more preferable.

The number of substituent is one or more, preferably one to three. Examples of the substituents include, $C_{1-3}$ alkyl (e.g. methyl, ethyl, propyl), $C_{2-4}$ alkenyl (e.g. vinyl, allyl, 2-buetnyl), $C_{3-4}$ alkynyl (e.g. propargyl, 2-butynyl), $C_{3-7}$ cycloalkyl (e.g. cyclopropyl, cyclobutyl, cyclopentyl, cyclohexyl), aryl (e.g. phenyl, naphthyl), 5- to 9-membered aromatic heterocyclic group having 1 to 4 hetero atoms selected from a nitrogen atom, an oxygen atom and a sulfur atom (e.g. furyl, thienyl, pyrrolyl, thiazolyl, imidazolyl, pyrazolyl, pyridyl), 5- to 9-membered nonaromatic heterocyclic group having 1 to 4 hetero atoms selected from a nitrogen atom, an oxygen atom and a sulfur atom (e.g. oxiranyl, azetidinyl, oxethanyl, thietanyl, pyrrolidinyl, tetrahydrofuryl, thioranyl, piperidinyl, tetrahydropyranyl, morpholinyl, thiomorpholinyl, piperazynyl), $C_{7-10}$ aralkyl (e.g. benzyl, phenethyl), amino, N-monosubstituted amino (e.g. N-$C_{1-6}$ alkyl amino such as methylamino, ethylamino, propylamino), N,N-disubstituted amino [e.g. N,N-di($C_{1-6}$ alkyl) amino such as dimethylamino, diethylamino], amidino, acyl (e.g. $C_{1-8}$ alkyl-carbonyl such as acetyl, propionyl, butyryl; $C_{6-14}$ aryl-carbonyl such as benzoyl; $C_{7-12}$ aralkyloxy-carbony such as benzyloxycarbonyl), carbamoyl, N-monosubstituted carbamoyl [e.g. N-($C_{1-6}$ ) alkyl)carbamoyl such as methylcarbamoyl, ethylcarbamoyl, ethylcarbamoyl, propylcarbamoyl], N,N-disustituted carbamoyl [e.g. N,N-di($C_{1-6}$ alkyl)carbamoyl such as dimethylcarbamoyl, diethylcarbamoyl], sulfamoyl, N-monosubstituted sulfamoyl [e.g. N-($C_{1-6}$ alkyl)sulfamoyl such as methylsulfamoyl, ethylsulfamoyl, propylsulfamoyl], N,N-disubstituted sulfamoyl [e.g. N,N-di($C_{1-6}$ alkyl) sulfamoyl such as dimethylsulfamoyl, diethylsulfamoyl], carboxyl, $C_{1-3}$ alkoxy-carbonyl (e.g. methoxycarbonyl, ethoxycarbonyl), hydroxyl, $C_{1-3}$ alkoxy (e.g. methoxy, ethoxy, propoxy) which may have a substituent (e.g. $C_{1-3}$ alkyl, halogen, $C_{1-3}$ alkylthio, hydroxyl), $C_{2-4}$ alkenyloxy (e.g. vinyloxy, allyloxy), cycloalkyloxy (e.g. $C_{3-7}$ cycloalkyloxy such as cyclopropyloxy, cyclobutyloxy), aralkyloxy (e.g. $C_{7-10}$ aralkyloxy such as benzyloxy), aryloxy (e.g. phenyloxy, naphthyloxy), mercapto, $C_{1-3}$ alkylthio (e.g. methylthio, ethylthio, propylthio), aralkylthio (e.g. $C_{7-10}$ aralkylthio such as benzylthio), arylthio (e.g. phenylthio, naphthylthio), $C_{1-3}$ alkylenedioxy (e.g. methylenedioxy, ethylenedioxy, propylenedioxy), sulfo, cyano, azide, nitro, nitroso, halogen *fulorine, chlorine, bromine iodine), and the like.

As the aralkyl in the optionally substituted aralkyl shown by $R^{12}$, mention is made of, for example, aryl-alkyl. The aryl is of the same meaning as defined above. Examples of the alkyl include $C_{1-6}$ alkyl such as methyl, ethyl, propyl, butyl, pentyl, hexyl. The substituents are of the same meaning as defined in the substituents which the above aryl, shown by $R^{12}$, may have.

As the cycloalkyl in the optionally substituted cycloalkyl shown by $R^{11}$ and $R^{12}$, mention is made of, for example, $C_{3-10}$ cycloalkyl and $C_{3-10}$ bicycloalkyl. The preferable examples of them include cyclolprolyl, cyclobutyl, cyclopentyl, cyclohexyl, cycloheptyl, cyclooctyl, bicyclo[2,2,1]heptyl, bicyclo[2,2,2]octyl, bicyclo[3,2,1]octyl, bicyclo[3,2,1]nonyl, bicyclo[4,2,1]nonyl, bicyclo[4,3,1]decyl. Among these, cyclopentyl and cyclohexyl are more preferable. The substituents are of the same meaning as definede in the substituents which aryl, shown by $R^{12}$, may have.

As the heterocyclic group in the optionally substituted heterocyclic group shown by $R^{11}$, mention is made of, for example, 5- to 13-membered aromatic heterocyclic group having one to four hetero atom(s) sedected from an oxygen atom, a sulfur atom and a nitrogen atom; or saturated or unsaturated non-aromatic heterocyclic group.

Examples of the aromatic heterocyclic group include an aromatic monocyclic heterocyclic group (e.g. furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl), an aromatic condensed-ring heterocyclic group {e.g. benzofuranyl, isobenzofuranyl, benzo[b]thienyl, indoryl, isoindoryl, 1H-indazolyl, benzoimidazolyl, benzoxazolyl, 1,2-benzoisoxazolyl, benzothiazolyl, 1,2-binzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyridazinyl, 1,2-4-tiazolo[4,3-a]pyridyl, 1,2,4-triazolo[4,3-b]pyridazinyl}.

Examples of the non-aromatic heterocyclic group include oxylanyl, azetizinyl, oxethanyl, thiethanyl, pyrrolidinyl, tetrahydrofuranyl, thiolanyl, piperidyl, tetrahydropyranyl, morpholinyl, thiomorpholinyl, piperazinyl.

The heterocyclic group may have one or more substituents, preferably one to three substituents. The substituents are of the same meaning as defined in the optionally substituted aryl shown by $R^{12}$.

As the substituents in the optionally substituted carboxyl group shown by Q, mention is made of, for example, alkyl, cycloalkyl, aryl, aralkyl, a heterocyclic group. These are of the same meaning as defined above.

As the lower alkylenedioxy shown by Q, mention is made of, for example, $C_{1-6}$ alkylenedioxy (e.g. methylenedioxy, ethylenedioxy, propylenedioxy, 2,2-dimethylmetylenedioxy).

As the lower alkyl shown by $R^{11}$, mention is made of, for example, $C_{1-6}$ alkyl (e.g. methyl, ethyl, propyl, isopropyl, butyl, t-butyl, pentyl, hexyl).

As the optionally substituted amino group shown by $R^{13}$, mention is made of, for example, a group of the formula: —$NR^{22}$, $R^{23}$, wherein $R^{22}$, is an optionally substituted aryl, an optionally substituted heterocyclic group;

$R^{23}$, is hydrogen, an optionally substituted alkyl).
The optionally substituted alkyl, optionally substituted cycloalkyl, optionally substituted aryl and optionally substituted heterocyclic group are of the same meaning as defined above.

As the spacer group shown by the symbol "A", mention is made of, for example, $C_{1-4}$ alkylene (e.g. methylene, ethylene), $C_{2-6}$ (e.g. vinylene, butadienylene); a group of the formula: —$(CH_2)cNR^{24}$—in which c is 0 to 3, $R^{24}$ is hydrogen, $C_{1-6}$ alkyl (e.g. methyl, ethyl, butyl); a group of the formula: —CO—; a group of the formula: —$CONR^{22}$— in which $R^{22}$ is of the same meaning as defined above; —O—; —S—; a group of the formula: —$NR^{22}S(O)e$— in which e is 0 to 2, $R^{22}$ is of the same meaning as defined above.

Preferable example of the homo or hetero 5- to 7-membered ring group (ring W') in the optionally substituted condensed-bicyclic compound consisting of a homo or hetero 5- to 7-membered ring group (ring W') and a homo or hetero 5- to 7-membered ring group (ring Y') includes a homo or hetero 5- or 6-membered ring group, more preferably a hetero 5- or 6-membered cyclic group. The concrete examples of the ring W'include ring groups of the formulae:

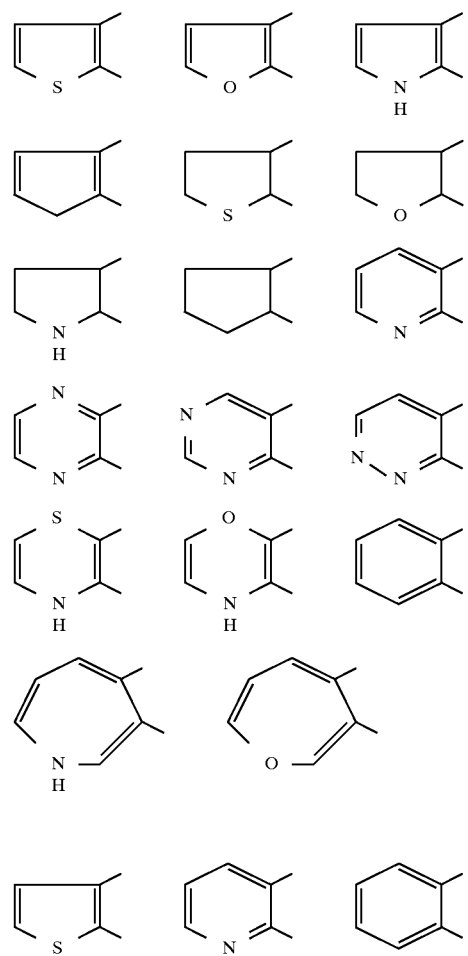

are preferable. Further, the cyclic group of the formula

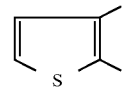

is especially preferable.

Most preferable example of the said W ring is that of the formula

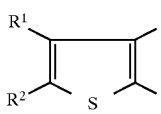

wherein $R^1$ and $R^2$ are of the same meaning as defined above.

Preferable example of the homo or hetero 5- to 7-membered ring group (ring Y') in the optionally substituted condensed-bicyclic compound consisting of a homo or hetero 5- to 7-membered ring group (ring W') and a homo or hetero 5- to 7-membered ring group (ring Y') includes a homo or hetero 6-membered ring group, more preferably a hetero 6-membered cyclic group. The concrete examples of the ring W'include ring groups of the formulae:

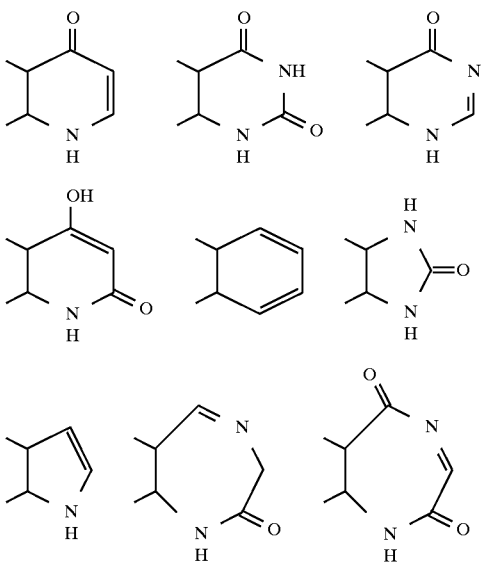

Among these cyclic groups, those of the formulae:

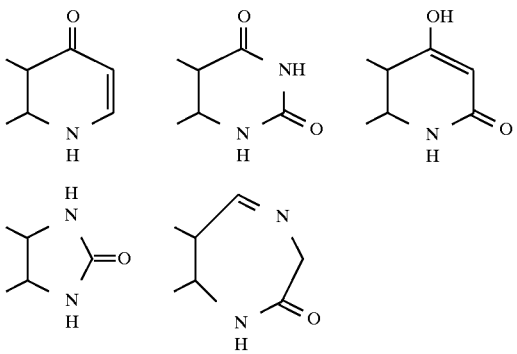

are preferable.

Further, the cyclic groups of the formulae:

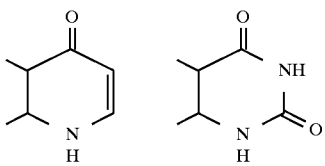

are more preferable.

More preferable examples of the said Y'ring is a ring group of the formula:

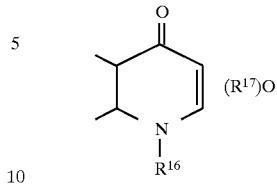

wherein $R^{16}$ is an optionally substituted hydrocarbons residue, $R^{17}$ is hydrogen, or a group bonded through a carbon atom, a nitrogen atom, oxygen atom or sulfur atom, o is 1 or 2;

or a ring group of the formula:

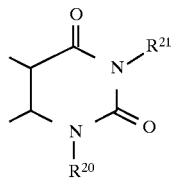

wherein $R^{20}$ and $R^{21}$ are each independently hydrogen, an optionally substituted hydrocarbon residure.

Examples of the hydrocarbon residues in the optionally substituted hydrocarbon residues shown by $R^{16}$, $R^{20}$ and $R^{21}$ include the alkyl, cycloalkyl, aryl and aralkyl described in the foregoing.

Examples of the substituents, which the said hydrocarbon residues may optionally have, include those optionally having 1 to 5 substituents selected from, for example, nitro, hydroxyl, oxo, thioxo, cyano, carbamoyl, carboxyl, $C_{1-4}$ alkoxy-carbonyl (e.g. methoxycarbonyl and ethoxycarbonyl), sulfo, halogen (fluorine, chlorine, bromine and iodine), $C_{1-6}$ alkoxy (e.g. methoxy, ethoxy, propoxy, isopropoxy, butoxy, isobutoxy, 2-butoxy and t-butoxy), $C_{6-12}$ aryloxy (e.g. phenoxy), halogeno $C_{6-16}$ aryl (e.g. o-, m- or p-chlorophenoxy, and o-, m- or p-bromophenoxy), $C_{1-6}$ alkylthio (e.g. methylthio, ethylthio, n-propiothio, isopropylthio, n-butylthio and t-butylthio), $C_{6-12}$ arylthio (e.g. phenylthio), $C_{1-6}$ alkylsulfinyl (e.g. methylsulfinyl and ethylsulfinyl), $C_{1-6}$ alkylsulfonyl (e.g. methylsulfonyl and ethylsulfonyl), amino, $C_{1-6}$ acylamino (e.g. formylamino, acetylamino and propylamino), mono- or di- $C_{1-4}$ alkylamino (e.g. methylamino, ethylamino, n-propylamino, isopropylamino, n-butylamino, dimethylamino and diethylamino), $C_{1-6}$ acyl (e.g. formyl, acetyl and hexanoyl), $C_{6-12}$ arylcarbonyl (e.g. benzoyl), 5- or 6-membered heterocyclic groups containing, besides carbon atoms, 1 to 4 hetero-atoms selected from oxygen, sulfur and nitrogen, as exemplified by 2- or 3-thienyl, 2- or 3-furyl, 3-, 4-or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H or 2H-tetrazolyl, 2-, 3- or 4-pyridyl, 2-, 4- or 5-pyrimidyl, 3- or 4-pyridazininyl, quinolyl, isoquinolyl and indolyl, and $C_{1-10}$ haloalkyl (e.g. difluoromethyl, trifluoromethyl, trifluoroethyl and trichloroethyl), and, in the case of the hydrocarbon group is cycloalkyl, cycloalkenyl, aryl or aralkyl group, $C_{1-6}$ alkyl (e.g. methyl, ethyl, propyl, isopropyl and butyl). The number of substituents ranges from 1 to 6, preferably 1 to 3.

The group bonded through a carbon atom, a nitrogen atom, an oxygen atom or a sulfur atom shown by $R^{17}$ is of the same meaning as defined above.

$R^1$ and $R^2$ are preferably such ones as either one of them being a group of the formula:

$$R^9-(CH_2)m-$$

wherein $R^9$ is a group bonded through nitrogen atom, and m is an integer of 0 to 3 and the other one being a group represented by the general formula:

$$R^{10}-A-$$

wherein $R^{10}$ is an optionally substituted phenyl group and A is spacer group.

The optionally substituted group, bonded through nitrogen atom, shown by the above-mentioned $R^9$ is of the same meaning as described above.

Examples of the substituents in optionally substituted phenyl group shown by the above-mentioned $R^{10}$ include halogen (fluorine, chlorine, bromine and iodine), $C_{1-8}$ alkyl (e.g. methyl, ethyl, propyl, isopropyl, butyl, isobutyl, sec-butyl, tert-butyl, pentyl, isopentyl and neopentyl) optionally substituted with 1 to 3 halogen atoms (fluorine, chlorine, bromine and iodine), $C_{1-8}$ alkoxy (e.g. methoxy, ethoxy, propoxy, isopropoxy, butoxy and isobutoxy) optionally substituted with 1 to 3 halogen atoms (e.g. fluorine, chlorine, bromine and iodine), $C_{1-8}$ alkylthio (e.g. methylthio, ethylthio, propylthio, isopropylthio, butylthio, sec-butylthio, tert-butylthio, pentylthio, isopentylthio and neopentylthio) optionally substituted with 1 to 3 halogen atoms (fluorine, chlorine, bromine and iodine), $C_{1-6}$ aralkyloxy (e.g. formyloxy, acetoxy and propionyloxy), hydroxyl, carboxyl, $C_{1-6}$ alkoxy-carbonyl (e.g. methoxycarbonyl, ethoxycarbonyl and t-butoxycarbonyl), cyano, nitro, amido, and mono- or di-$C_{1-6}$ alkylcarbamoyl (e.g. methylcarbamoyl, ethylcarbamoyl and dimethylcarbamoyl). The number of substituents ranges from 1 to 5, preferably 1 to 3.

The spacer groups shown by A is of the same meaning as defined above.

$R^3$ is preferably a group of the formula:

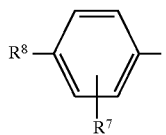

wherein $R^7$ is hydrogen or a group bonded through a carbon, nitrogen, oxygen or sulfur atom, and $R^8$, halogen, nitro, cyano or an optionally substituted aliphatic hydrocarbon residue bonded through oxygen, nitrogen or sulfur atom.

The above-mentioned optionally substituted groups bonded through carbon, nitrogen oxygen or sulfur atom, shown by $R^7$ are of the same meaning as defined above.

Examples of the optionally substituted aliphatic hydrocarbon residue, in the optionally substituted aliphatic hydrocarbon residue bonded through oxygen, nitrogen or sulfur atom shown by the above-mentioned $R^8$, include $C_{1-15}$ alkyl (e.g. methyl, ethyl, propyl, isopropyl, butyl, isobutyl, s-butyl, pentyl, hexyl, heptyl, octyl, nonyl, decyl, undecyl, dodecyl, tridecyl, tetradecyl and pentadecyl), $C_{3-8}$ cycloalkyl (e.g. cyclopropyl, cyclobutyl, cyclopentyl and cyclohexyl), $C_{2-10}$ alkenyl (e.g. vinyl, allyl, 2-methylallyl, 2-butenyl, 3-butenyl and 3-octenyl), $C_{2-10}$ alkynyl (e.g. ethynyl, 2-propynyl and 3-hexynyl)and $C_{1-6}$ alkoxy (e.g. methoxy, ethoxy, propoxy and butoxy). Examples of the substituents, which the said hydrocarbon group may have, include nitro, hydroxyl, oxo, thioxo, cyano, carbamoyl, carboxyl, $C_{1-4}$ alkoxy-carbonyl (e.g. methoxycarbonyl and ethoxycarbonyl), sulfo, halogen (fluorine, chlorine, bromine and iodine), $C_{1-4}$ alkoxy (e.g. methoxy, ethoxy, propoxy, isopropoxy, butoxy, isobutoxy, s-butoxy and t-butoxy), $C_{1-4}$ alkylthio (e.g. methylthio, ethylthio, n-propylthio, isopropylthio, n-butylthio and t-butylthio), amino, $C_{1-6}$ alkanoylamino (e.g. acetylamino and propionylamino), mono- or di- $C_{1-4}$ alkylamino (e.g. methylamino, ethylamino, n-propylamino, isopropylamino, n-butylamino, dimetylamino and diethylamino), $C_{1-4}$ alkanoyl (e.g. formyl, acetyl and propionyl), 5- or 6-membered heterocyclic groups containing, besides carbon atoms, 1 to 4 heteroatoms selected from oxygen, sulfur and nitrogen, which may optionally have 1 to 4 substituents selected from (a) halogen (e.g. fluorine, chlorine, bromine and iodine); and (b) $C_{1-4}$ alkyl (e.g. methyl, ethyl, propyl and isopropyl), as exemplified by 2- or 3-thienyl, 2- or 3-furyl, 3-, 4- or 5-pyrazolyl, 2-, 4- or 5-thiazolyl, 3-, 4- or 5-isothiazolyl, 2-, 4-or 5-oxazolyl, 3-, 4- or 5-isoxazolyl, 2-, 4- or 5-imidazolyl, 1,2,3- or 1,2,4-triazolyl, 1H or 2H-tetrazolyl, 2-, 3- or 4-pyridyl, 2-, 4- or 5-pyrimidyl, 3- or 4-pyridazinyl, quinolyl, isoquinolyl and indolyl, and $C_{1-6}$ haloalkyl (e.g. difluoromethyl, trifluoromethyl, trifluoroethyl and trichloroethyl). Number of the substituents ranges from 1 to 4, preferably 1 to 3.

$R^{11}$ is preferably a group of the formula:

$$-(CH_2)pQ'$$

wherein p is an integer of 1 to 3;

Q' is aryl which may be substituted by halogen, nitro, cyano, amino, an optionally substituted carboxyl group, lower alkylenedioxy or a group of the formula: $-A-R^{16}$ in which $R^{15}$ is a lower alkyl group, A is of the same meaning as defined above.

The aryl which may be substituted by halogen, nitro, cyano, amino, the optionally substituted carboxyl group, lower alkylenedioxy or the group of the formula: $-A-R^{16}$, shown by Q', are the of the same meaning as defined above. The lower alkyl group is of the same meaning as defined above.

Q' is preferably an aryl which may be substituted by halogen (fluorine, chlorine, bromine, nitrogen).

$R^{13}$ is preferably an optionally substituted monoaralkylamino. The optionally substituted aralkyl in the optionally substituted monoaralkylamino is of the same meaning as defined above. The aralkyl is preferably benzyl.

$R^{14}$ is preferably optionally substituted phenyl which is of the same meaning as defined above.

The optionally substituted condensed-bicyclic compound consisting of a homo or hetero 5- to 7-membered ring group and a homo or hetero 5- to 7-membered ring group is preferably a compound of the formula (V):

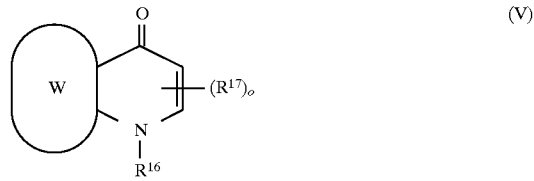

wherein ring W, $R^{16}$ $R^{17}$ and o are the same meaning as defined above; or a compound of the formula (VII):

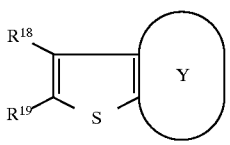

wherein $R^{18}$ and $R^{19}$ are each independently an optionally substituted hydrocarbon residue and ring Y is of the same meaning as defined above.

The optionally substituted hydrocarbon residue shown by $R^{18}$ or $R^{19}$ is the same meaning as defined above.

The ring Y is preferably an optionally substituted hetero 5- to 7-membered ring group except for 4-pyridone. More preferably, the ring Y is a ring group of the formula (VIII):

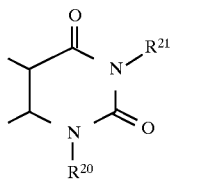

wherein $R^{20}$ and $R^{21}$ are of the same meaning as defined above.

The ring W is preferably a ring group of the formula (VI):

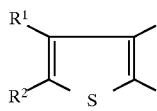

wherein $R^1$ and $R^2$ are of the same meaning as defined above.

The compounds (I), (II), (VII) and their salts can be produced easily by per se known methods, as exemplified by the following production methods 1 to 16.

The above-mentioned optionally substituted condensed-bicyclic compound consisting of a homo or hetero 5- to 7-membered ring group and a homo or hetero 5- to 7-membered ring group can be produced by the production methods 1 to 16 or the same production methods thereof.

[Production Method 1]

In accordance with the method disclosed by K. Gewald, E. Schinke and H. Bøttcher, Chem. Ber., 99, 94–100 (1966), an adequate ketone or aldehyde having an active methylene (i) was allowed to react with a cyanoacetic acid ester derivative and sulfur to convert into a 2-aminothiophene derivative (ii). More specifically, in the case of using ketone ($R^{1'} \neq H$), it is subjected to heating under reflux together with a cyanoacetic acid ester derivative, in the presence of acetic acid and ammonium acetate, in a proper solvent such as toluene to give an alkylidene cyanoacetic acid ester derivative, which is then heated in an adequate solvent, for example, ethanol in the presence of sulfur and a base to afford a 2-aminothiophene derivative (ii). And, in the case of using aldehyde ($R^{1'}=H$), it is heated in a proper solvent, for example, dimethylformamide, in the presence of a cyanoacetic acid ester derivative, sulfur and a base to give a 2-aminothiophene derivative (ii). The compound (ii) thus obtained is heated, in accordance with the method disclosed by Kuwata et al. [cf. German Patent 2,435,025], with diethyl ethoxymethylenemalonate to give an adduct (iii). The adduct is stirred in a solvent, which does not give undesirable effect on the reaction, (e.g. alcohols such as ethanol and methanol), in the presence of a base (e.g. alkali metal hydroxide such as potassium hydroxide and sodium hydroxide) at temperatures ranging from about 10° to 70° C. to give carboxylic acid (iv). Then, the carboxylic acid (iv) thus obtained was subjected to ring-closure by heating in polyphosphoric acid ester (PPE) to give a thieno[2,3-b]pyridine derivative (v). The compound (v) is stirred in a solvent, which does not give undesirable effect on the reaction, (e.g. amides such as dimethylformamide and dimethylacetamide), in the presence of a halogenated aralkyl derivative and a base (e.g. an organic base such as pyridine and triethylamine) at temperatures ranging from about 10° to 100° C. to give a 4,7-dihydro-4-oxothieno[2,3-b]pyridine-5-carboxylic acid ester derivative shown by the formula (Ia). Then, the compound (Ia) is stirred together with N-bromosuccinimide (NBS) in a solvent, which does not give undesirable effect on the reaction, (e.g. halogenated hydrocarbons such as carbon tetrachloride and chloroform) in the presence of α, α'-azobisisobutyronitrile, at temperatures ranging from about 30° to 100° C. to give a compound (Ib). The compound (Ib) is stirred together with various amines in a solvent, which does not give undesirable effect on the reaction, (e.g. amides such as dimethylformamide and dimethylacetamide, nitrile such as acetonitrile and alcohols such as ethanol) in the presence of a base at temperatures ranging from about 10° to 100° C. to produce the compound (I). The production method 1 described above is shown in Scheme 1:

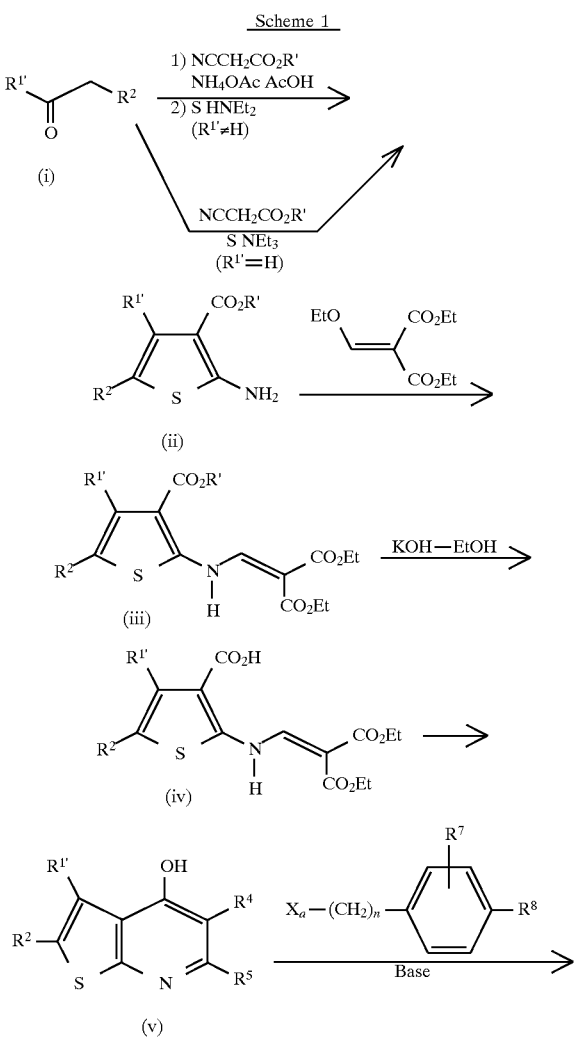

-continued
Scheme 1

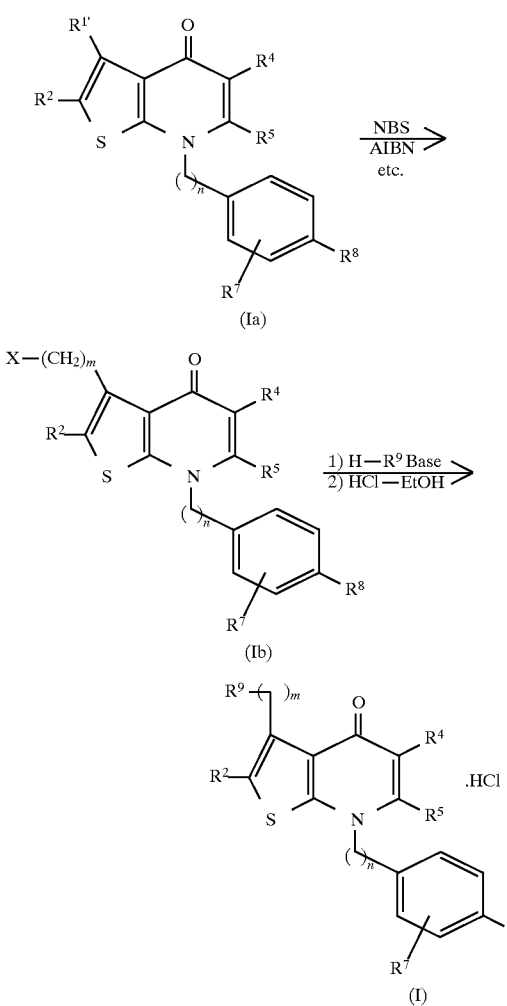

wherein $R^{1'}$ is hydrogen or an alkyl group, R' is an alkyl group, X is a leaving group, Xa is halogen, and $R^2, R^4, R^5, R^7, R^8, R^9$, m and n are of the same meaning as defined in the above.

The alkyl group shown by $R^{1'}$ and R' is of the same meaning as defined above.

As the leaving group shown by X, mention is made of, for example, a group which is potentially substituted by a nucleophilic reagent such as a hydrocarbon residue having a hetero atom (e.g. an oxygen atom, a sulfur atom, a nitrogen atom) being negatively charged. The preferable examples of the leaving group include halogen (e.g. iodine, bromine chlorine), alkanoyloxy (e.g. acetoxy), alkylsulfonyloxy (e.g. methanesulfonyloxy), alkyl-arylsulfonyloxy (e.g. p-toluenesulfonyloxy).

The halogen shown by Xa is fluorine, iodine, chlorine, iodine. Among these, bromine is more preferable.

[Production Method 2]

In substantially the same manner as in [production Method 1], a 2-aminothiophene derivative whose 5-position is unsubstituted (vi), which can be synthesized by the method disclosed by Karl Gewald [K. Gewald, Chem. Ber., 98, 3571–3577 (1965); K. Gewald and E. Schinke, Chem. Ber., 99, 2712–2715 (1966)] is allowed to react with diethyl ethoxymethylene malonate under heating, in accordance with the method disclosed by Kuwata et al. [German Patent 2,435,025], to give an adduct (vii). The adduct is stirred at temperatures ranging from 10° to 60° C. in a solvent, which does not affect adversely on the reaction, (e.g. alcohols such as ethanol and methanol) in the presence of a suitable base (e.g. alkali metal hydroxide such as potassium hydroxide and sodium hydroxide to give carboxylic acid (viii). The compound (viii) is subjected to various cationoid substitution reactions and, depending on cases, to a suitable change of functional groups to introduce the substituent shown by $R^2$, which is then subjected to ring-closure reaction under heating in polyphosphoric acid ester (PPE) to give a thieno[2,3-b]pyridine derivative (ix). The compound (ix) is stirred together with a halogenated aralkyl derivative in a solvent, which does not affect adversely on the reaction, (e.g. amides such as dimethylformamide and dimethylacetamide), in the presence of a base, at temperatures ranging from about 10° to 100° C., to give a 4,7-dihydro-4-oxothieno[2,3-b]pyridine-5-carboxylic acid ester derivative shown by the formula (Ia). As the cationoid-substitution reaction, mention is made of, for example, nitration (fuming nitric acid—concentrated sulfuric acid, sodium nitrate—concentrated sulfuric acid), acylation (acid chloride—aluminum chloride), formylation (phosphorus oxychloride—dimethylformamide or N-methylformanilide) and bromination (N-bromosuccinimide, bromine-pyridine). The compound (Ia) is then processed in substantially the same manner as in [Production Method 1] to produce the compounds (Ib) and (I). The Production Method 2 is shown in Scheme 2:

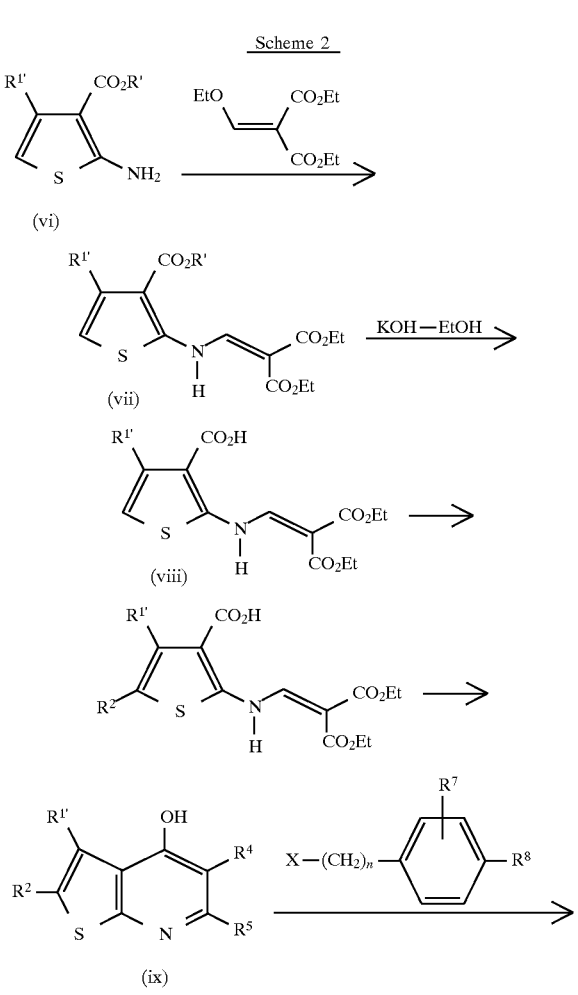

-continued
Scheme 2

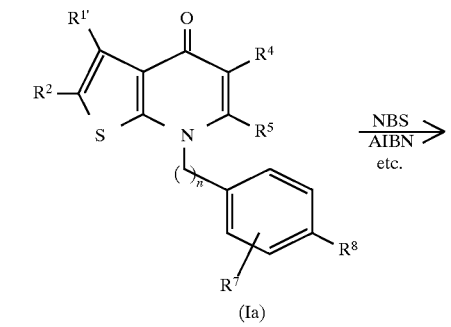

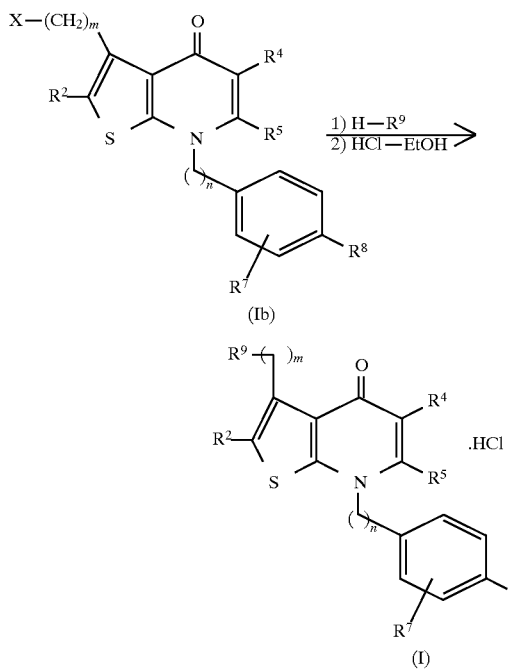

wherein each symbol has the same meaning as defined above.

[Production Method 3]

An alantoic acid derivative (x) is stirred at temperatures ranging from about 30° to 110° C. together with an equivalent or an excess amount of triphosgene relative the compound (x) in a solvent which does not adversely affect on the reaction (e.g. ethers such as tetrahydrofuran and 1,4-dioxane) to give an isatoic acid anhydride derivative (xi). Then, a halogenated derivative shown by the formula (xii) is stirred at temperatures ranging from about 40° to 130° C. in a solvent, which does not affect adversely on the reaction, (ethers such as tetrahydrofuran and 1,4-dioxane, aromatic hydrocarbons such as benzene and toluene, amides such as N,N-dimethylformamide and N,N-dimethylacetamide, alkylsulfoxides such as dimethyl sulfoxide), in the presence of a base (e.g. alkali metal carbonate such as potassium carbonate, alkali metal hydride such as sodium hydride and potassium hydride, and alkali metal alkoxide such as potassium-butoxide), to give a substituted derivative (xiii). The derivative (xiii) is allowed to react with an equivalent or a little excess amount (e.g. about 1.1 to 1.5 equivalent) of a β-keto-acid ester derivative (xiv) relative to the compound (xiii) at temperatures ranging from 40° to 110° C. in a solvent, which does not affect adversely on the reaction, (e.g.

ethers such as tetrahydrofuran and 1,4-dioxane, aromatic hydrocarbons such as benzene and toluene, amides such as N,N-dimethylformamide and N,N-dimethylacetamide, and alkyl sulfoxide such as dimethyl sulfoxide), in the presence of a base (e.g. alkali metal carbonate such as potassium carbonate, alkali metal hydride such as sodium hydride and potassium hydride, and alkali metal alkoxide such as potassium-butoxide) to give the compound (Va). The foregoing production method 3 is shown in Scheme 3:

Scheme 3

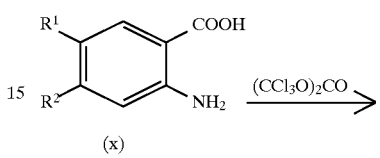

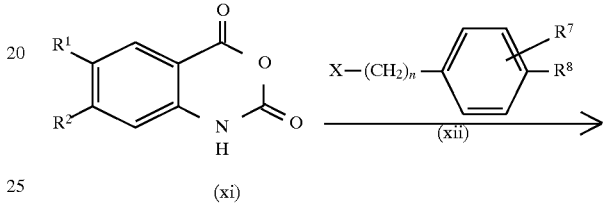

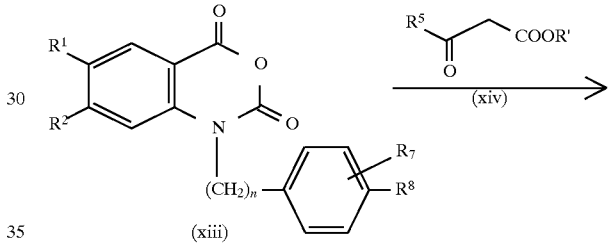

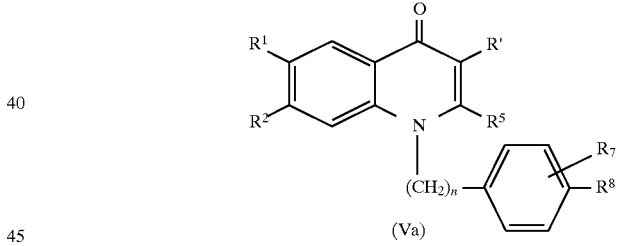

wherein each symbol is of the same meaning as defined above.

[Production Method 4]

A pyridine derivative (xv) is stirred, together with equivalent or an excess amount of triphosgene relative to the compound (xv), in a solvent, which does not affect adversely on the reaction, (e.g. ethers such as tetrahydrofuran and 1,4-dioxane), at temperatures ranging from about 30° to 110° C. to give an acid anhydride derivative (xvi). Then, the halogenated derivative shown by (xii) is stirred in a solvent, which does not affect adversely on the reaction, (e.g. ethers such as tetrahydrofuran and 1,4-dioxane, aromatic hydrocarbons such as benzene and toluene, amides such as N,N-dimethylformamide and N,N-dimethylacetamide, and alkyl sulfoxides such as dimethyl sulfoxide), at temperatures ranging from about 40° to 130° C. in the presence of a base (e.g. alkali metal carbonate such as potassium carbonate, alkali metal hydride such as sodium hydride and potassium hydride, and alkali metal alkoxide such as potassium-butoxide) to give a substituted derivative (xvii). The derivative (xvii) is allowed to react with equivalent or a little excess amount (e.g. 1.1 to 1.5 equivalent) of a β-keto-acid ester derivative (xiv) in a solvent, which does not affect adversely on the reaction, (e.g. ethers such as tetrahydrofuran and 1,4-dioxane, aromatic hydrocarbons such as benzene and toluene, amides such as N,N-dimethylformamide and M,N-dimethylacetamide, and alkyl sulfoxides such as dimethyl sulfoxide), in the presence of a base (e.g. alkali metal carbonate such as potassium carbonate, alkali metal hydride such as sodium hydride and potassium hydride and alkali metal alkoxide such as potassium-butoxide), at temperatures ranging from about 40° to 110° C., to give the compound (Vb). The foregoing production method 4 is shown by Scheme 4:

together with a Grignard's reagent, at temperatures ranging from about 0° to 80° C. in a solvent, which does not affect adversely on the reaction, (e.g. ethers such as tetrahydrofuran and ethyl ether) to give a corresponding secondary alcohol derivative (Ie). The compound (Ie) is stirred, together with a suitable oxidizing agent (e.g. metal oxide such as manganese dioxide), in a proper solvent (e.g. halogenated hydrocarbons such as dichloromethane and chloroform) at temperatures ranging from 10° to 80° C. to give a 5-carbonyl derivative (If). The foregoing production method 5 is shown in Scheme 5:

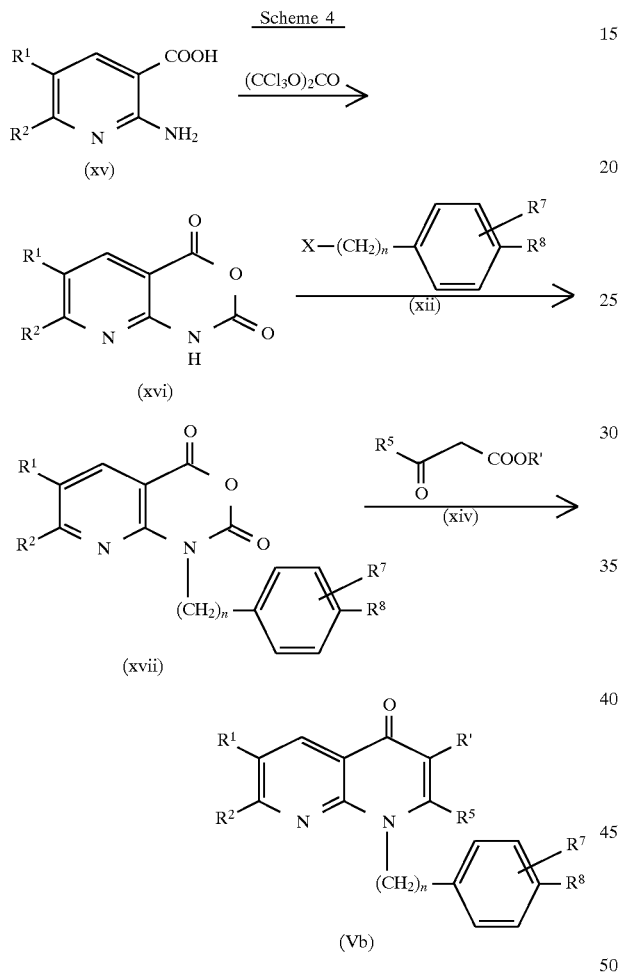

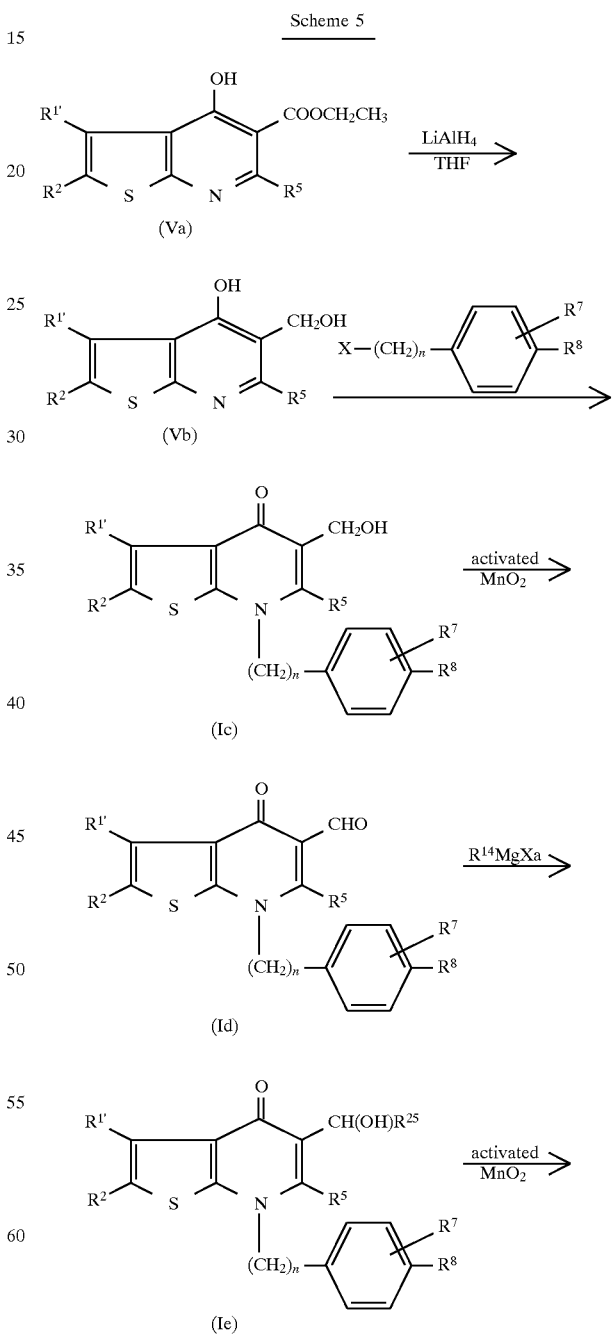

wherein each symbol is of the same meaning as defined above.

[Production Method 5]

In a proper solvent, which does not affect adversely on the reaction, (e.g. ethers such as tetrahydrofuran, ethyl ether and dioxane), 4,7-dihydro-4-oxothieno[2,3-b]pyridine-5-carboxylic acid ester derivative (va) is stirred together with a suitable reducing agent (e.g. lithium aluminum hydride) at temperatures ranging from about 0° to 80° C. to give a 4,7-dihydro-thieno[2,3-b]pyridine-4-one derivative shown by the formula (Ic). The said derivative is stirred, together with a suitable oxidizing agent (e.g. manganese dioxide), in a proper solvent (e.g. dichloromethane or chloroform) at temperatures ranging from 10° to 80° C. to give a 5-formyl derivative. The derivative (Id) thus produced is stirred, -continued
Scheme 5

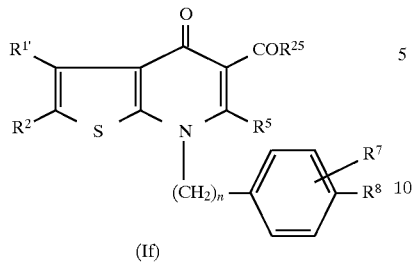

(If)

wherein $R^{25}$ is hydrocarbon residue, and other symbols are of the same meaning as defined above.

The hydrocarbon residue shown by the above $R^{25}$ is of the same meaning as the hydrocarbon residue in the carbonyl group optionally substituted with hydrocarbon residue shown by the above-described $R^4$.

[Production Method 6]

4,7-Dihydro-4-oxothieno[2,3-b]pyridine-5-carboxylic acid ester derivative (Ia') is stirred at temperatures ranging from 10° to 100° C., together with an aluminum amide derivative previously produced from a proper aluminum reagent [(e.g. trimethyl aluminum and diisobutyl aluminum hydride (DIBAL)] and amine in a suitable solvent, which does not affect adversely on the reaction, (e.g. halogenated hydrocarbons such as dichloromethane and ethers such as tetrahydrofuran, ethyl ether and dioxane), to give a 4,7-dihydro-4-oxothieno[2,3-b]pyridine-5-carboxylic acid amide derivative (Ia"). The said derivative (Ia") is stirred, together with a Grignard's reagent, in a proper solvent, which does not affect adversely on the reaction, (e.g. tetrahydrofuran and ethyl ether) at temperatures ranging from about −78° C. to 80° C. to give a corresponding ketone derivative (If). The foregoing production method 6 is shown in Scheme 6:

Scheme 6

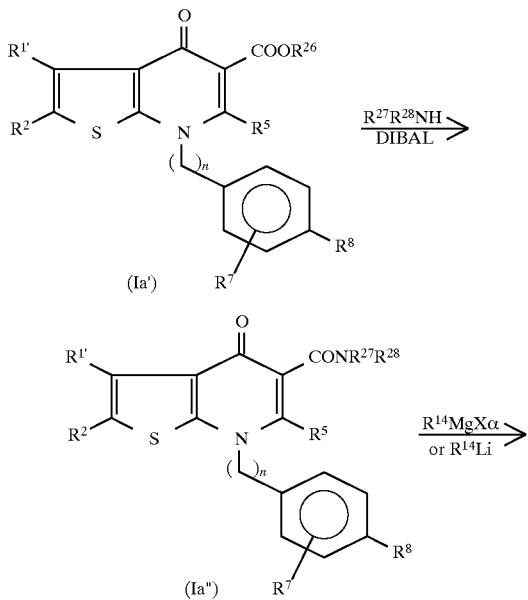

-continued
Scheme 6

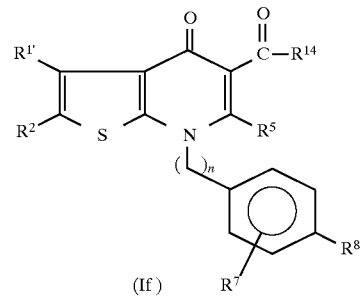

(If)

wherein $R^{26}$ is alkyl or aryl; $R^{27}$ and $R^{28}$ are each hydrogen or hydrocarbon residue; and other symbols are of the same meaning as defined above.

The alkyl and aryl shown by the above $R^{26}$ are of the same meaning as defined above.

The hydrocarbon residue shown by the above $R^{27}$ and $R^{28}$ has the same meaning as the hydrocarbon residue in the carbonyl group optionally substituted with hydrocarbon residue shown by the above $R^4$.

[Production Method 7]

In a proper solvent, which does not affect adversely on the reaction, (e.g. halogenated hydrocarbons such as dichloromethane; ethers such as tetrahydrofuran, ethyl ether and dioxane; and pyridine), a 4,7-dihydro-5-hydroxymethylthieno[2,3-b]pyridine-4-one derivative (Ia''') is stirred together with a suitable halogenating reagent (e.g. thionyl chloride and methanesulfonyl chloride) at temperatures ranging from about 0° to 100° C. to give a 4,7-dihydrothieno[2,3-b]pyridine one derivative (Ig). The said derivative (Ig) is stirred, together with a suitable nucleophilic reagent, in a proper solvent, which does not affect adversely on the reaction, (e.g. ethers such as tetrahydrofuran and ethyl ether; and amides such as dimethylformamide) to give a corresponding 5-substituted derivative (Ih). The above production method 7 is shown in Scheme 7:

Scheme 7

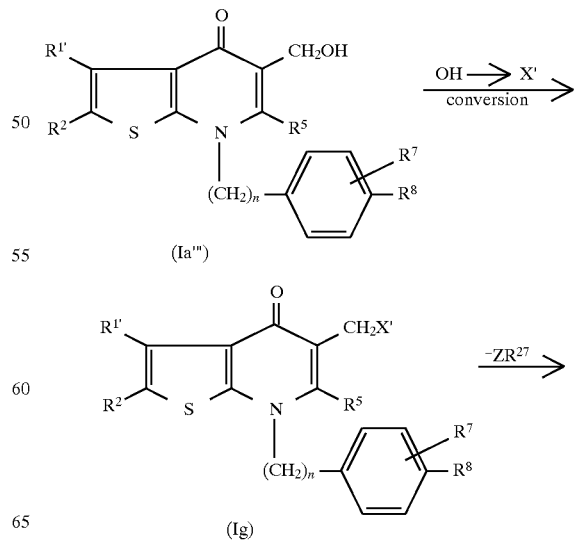

-continued
Scheme 7

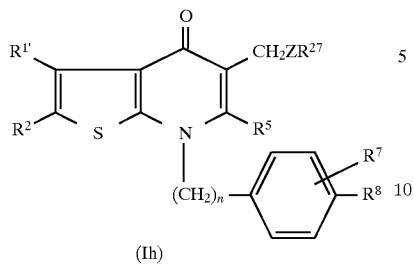

(Ih)

wherein X' is a leaving group, Z is an oxygen atom, a sulfur atom or a nitrogen atom optionally substituted with hydrocarbon residue, and other symbols are of the same meaning as defined above.

As the leaving group shown by the above X', mention is made of, for example, groups readily susceptible to substitution reaction by a nucleophilic reagent [e.g. the hydrocarbon residue having a hetero-atom with negative electric charge (e.g. oxygen atom, sulfur atom and nitrogen atom) shown by the above $^-YR^{16}$]. More specifically, for example, aralkyloxy (e.g. acetoxy), alkylsulfonyloxy (e.g. methanesulfonyloxy) and alkyl-aryl sulfonyloxy (e.g. p-toluenesulfonyloxy) are mentioned.

The hydrocarbon residue in the nitrogen atom optionally substituted with hydrocarbon residue mentioned above has the same meaning as defined in reference to the hydrocarbon residue in the carbonyl group optionally substituted with hydrocarbon residue shown by the above-mentioned $R^4$.

[Production Method 8]

In a proper solvent, which does not affect adversely on the reaction, (e.g. ethers such as tetrahydrofuran, ethyl ether and dioxane; and pyridine), 4,7-dihydro-5-formylthieno[2,3-b]pyridine-4-one derivative (Ih) is stirred together with a suitable Wittig reagent at temperatures ranging from about 0° to 100° C. to give a 4,7-dihydrothieno[2,3-b]pyridine-4-one derivative (Ij). The said derivative (Ij) is stirred at temperatures ranging from 10° to 100° C. together with a suitable reducing reagent [e.g. hydrogenation using, in hydrogen streams, a catalyst (e.g. palladium-carbon catalyst)] in a proper solvent, which does not affect adversely on the reaction (e.g. alcohols such as ethyl alcohol, esters such as acetic acid ethyl ester, ethers such as tetrahydrofuran, ethyl ether and dimethylformamide) to give a corresponding 5-substituted derivative (Ik). The above production method 8 is shown in Scheme 8:

Scheme 8

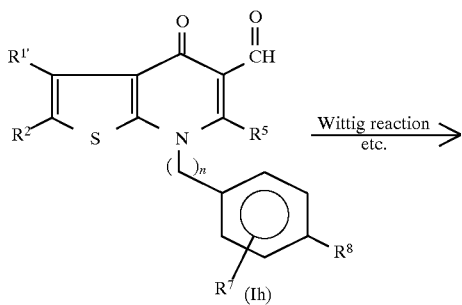

(Ih)

-continued
Scheme 8

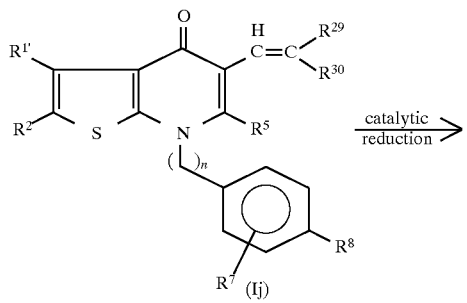

(Ij)

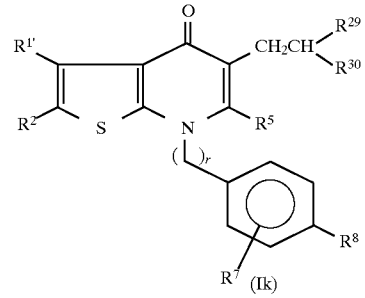

(Ik)

wherein $R^{29}$ and $R^{30}$ are each hydrogen or hydrocarbon residue, and other symbols are of the same meaning as defined above.

The hydrocarbon residue shown by the above-mentioned $R^{29}$ and $R^{30}$ has the same meaning as the hydrocarbon residue in the carbonyl group optionally substituted with the hydrocarbon residue shown by the above-mentioned $R^4$.

[Production Method 9]

In a proper solvent, which does not affect adversely on the reaction, (e.g. ethers such as tetrahydrofuran and dioxane; and alcohols such as ethyl alcohol), 4,7-dihydro-4-oxothieno[2,3-b]pyridine-5-carboxylic acid ester derivative (Ia') is subjected to hydrolysis under stirring at temperatures ranging from 10° to 100° C. by adding an acid (e.g. inorganic acid such as hydrochloric acid) or an alkaline aqueous solution (e.g. 1–4N aqueous solution of alkali metal hydroxide such as sodium hydroxide, potassium hydroxide and lithium hydroxide). The resulting 5-carboxylic acid derivative is heated at temperatures ranging from about 50° to 200° C. in a proper solvent, which does not affect adversely on the reaction, to give a corresponding decarboxylated derivative (In). The foregoing production method 9 is shown by Scheme 9:

Scheme 9

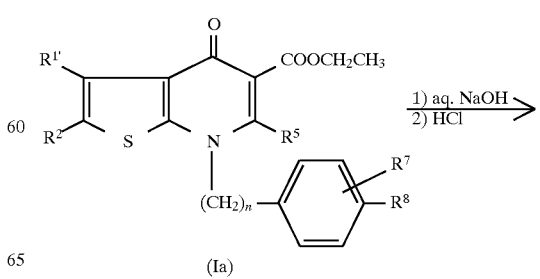

(Ia)

-continued
Scheme 9

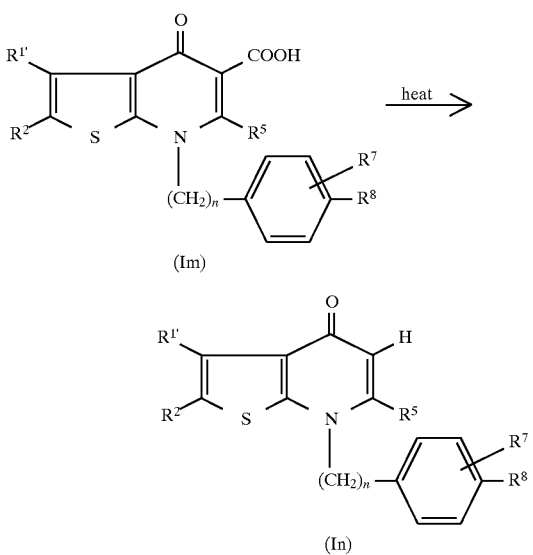

wherein each symbol is of the same meaning as defined above.

[Production Method 10]

Starting from the 2-aminothiophene derivative (ii), the urea derivative (II) was produced by, for example, the following method A or B.

1. Method A: The 2-aminothiophene derivative (ii) produced by the method described in Production Method 1 or a salt thereof is allowed to react with an isocyanate derivative. The isocyanate derivative is exemplified by derivatives represented by the formula, $R^{12}$—NCO (wherein $R^{12}$ is of the same meaning as defined above). The reaction of the compound (ii) or a salt thereof with the isocyanate derivative is conducted in an solvent which does not adversely affect on the reaction (e.g. tetrahydrofuran, pyridine, dioxane, benzene, dichloromethane, 1,2-dichloroethane, toluene, xylene) at temperatures ranging from about 15° to about 130° C. The isocyanate derivative is employed in an amount of about 1 to 5 equivalents, preferably about 1.1 to 2.5 equivalents, relative to 1 equivalent of the compound (ii). The reaction time ranges from several hours to several days, preferably from about 15 minutes to about two days.

2. Method B: Amine [e.g. a compound represented by the formula $R^{12}$—$NH_2$ (wherein $R^{12}$ is of the same meaning as defined above)] is subjected to addition reaction to an isocyanate derivative produced by allowing a 2-aminothiophene derivative (ii) or a salt thereof to react with phosgene or an equivalent compound thereof [e.g. diphosgene such as bis(trichloromethyl)carbonate, triphosgene such as trichloromethylchloroformate]. The reaction of the compound (ii) or a salt thereof with phosgene or an equivalent compound thereof is conducted in a solvent which does not affect adversely on the reaction (e.g. dioxane, tetrahydrofuran, benzene, toluene, xylene, 1,2-dichloroethane, chloroform) at temperatures ranging from about 40° to 120° C. Phosgene or an equivalent compound thereof is employed in an amount ranging from about 0.5 to 2 equivalents, preferably from about 0.9 to 1.1 equivalent). The reaction time ranges from several minutes to several days, preferably from about 15 minutes to about two days. The addition reaction of amine is conducted in a solvent which does not affect adversely on the reaction (e.g. pyridine, tetrahydrofuran, dioxane, benzene, dichloromethane, 1,2-dichloroethane, toluene, xylene) at temperatures ranging from about 15° to 130° C. Amine is employed in an amount ranging from about 1 to 5 equivalents, preferably from about 1.1 to 3 equivalents. The reaction time ranges from several minutes to several days, preferably from about 15 minutes to about two days.

The compound (XV) or a salt thereof thus produced is processed with a base to cause ring-closure reaction to thereby produce a thieno [2,3-d] pyrimidine derivative (XVI). The ring-closure reaction is conducted in a solvent which does not affect adversely on the reaction. The solvent is exemplified by alcohols such as methanol, ethanol or propanol, and ethers such as dioxane or tetrahydrofuran.

As the base, use is made of, for example, an alkali metal alkoxide such as sodium methylate, sodium ethylate or sodium isopropoxide, and an alkali metal hydride such as sodium hydride.

The amount of the base to be employed ranges from 1 to 5 equivalents, preferably from about 1.5 to 3 equivalents, relative to 1 equivalent of the compound (XV).

The reaction temperature ranges from about 10° C. to the boiling point of the solvent then employed, preferably from about 25° C. to the boiling point of the solvent then employed.

The reaction time ranges from several minutes to several days, preferably from about 10 minutes to two days.

The compound (XVI) and a halogenated aralkyl derivative are stirred, in the presence of a base (e.g. an organic base such as pyridine or triethylamine), in a solvent which does not affect adversely on the reaction (e.g. amides such as dimethylformamide or dimethylacetamide), at 10° to 100° C., to produce a 2,4-dioxothieno[2,3-d]pyrimidine derivative (IIa). Subsequently, the said compound (IIa) is stirred together with N-bromosuccinimide (NBS) in a solvent which does not affect adversely on the reaction (e.g. halogenated hydrocarbons such as carbon tetrachloride or chloroform), in the presence of α, α'-azobisisobutyronitrile, to thereby produce the compound (IIb). Further, the said compound is stirred together with various amines, in the presence of a base, in a solvent which does not affect adversely on the reaction (e.g. amides such as dimethylformamide or dimethylacetamide, nitrites such as acetonitrile, alcohols such as ethanol), at temperatures ranging from 10° to 100° C., to thereby produce the compound (II). When necessary, the said compound is made into a corresponding salt with a suitable acid (e.g. hydrochloric acid or oxalic acid).

The foregoing Production Method 10 is shown by Scheme 10:

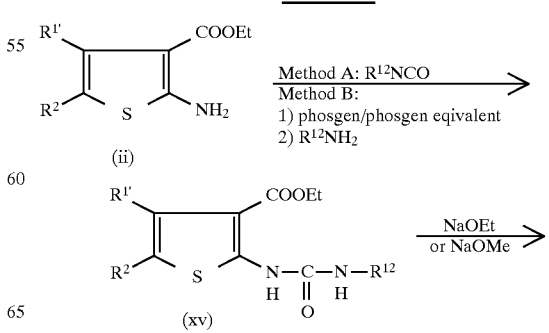

-continued
Scheme 10

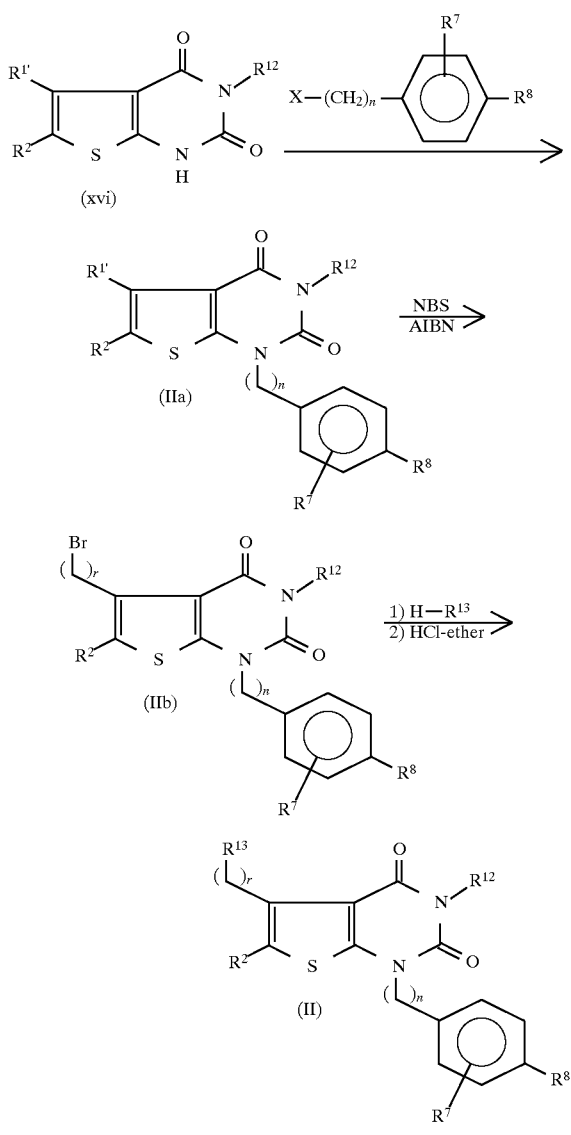

wherein each symbol is of the same meaning as defined above.

[Production Method 11]

The amino group of a 2-aminothiophene derivative (xvii) was protected (e.g. Boc), which was stirred, in accordance with the method of T. Hirohashi et al. [Ger. Pat., 2155403 (1972), among others] or the method of M. Nakanishi et al. [Jap. Pat., 73, 01664 (1973), among others], together with a halogenated acyl derivative, in the presence of a base, in a solvent which does not affect adversely on the reaction (e.g. amides such as dimethylformamide or dimethylacetamide) at temperatures ranging from about 0° to 100° C. to give a derivative (xviii), which was stirred together with a suitable salt (e.g. lithium iodide) in a suitable solvent (e.g. acetone or methyl ethyl ketone) to give a derivative (xix), which was subjected to substitution reaction with a suitable amine (e.g. ammonia) to give a derivative (xx), which was stirred in a solvent which does not affect adversely on the reaction (e.g. toluene, dimethylformamide, dimethylacetamide, methanol or ethanol), when necessary in the presence of a suitable catalyst (e.g. sodium ethoxide or toluenesulfonic acid) at temperatures ranging from about 30° to 120° C., to cause dehydro-cyclization to thereby produce a derivative (VIIa). The said compound was stirred, together with a halogenated aralkyl derivative, in the presence of a base (e.g. organic bases including potassium carbonate, pyridine and triethylamine), in a solvent which does not affect adversely on the reaction (e.g. amides including dimethylformamide and dimethylacetamide), at temperatures ranging from 10° to 100° C. to give a 2-oxothieno [2,3-e] azepine derivative (VIIb). Subsequently, the said compound (VIIb) was stirred together with N-bromosuccinimide (NBS) in a solvent (e.g. halogenated hydrocarbons including carbon tetrachloride and chloroform), in the presence of α,α'-azobisisobutyronitrile, at temperatures ranging from about 30° to 100° C., to give a compound (VIIc). The said compound was stirred with various amines in the presence of a base, in a solvent which does not affect adversely on the reaction (e.g. amides including dimethylformamide and dimethylacetamide, nitriles including acetonitrile, and alcohols including ethanol) at temperatures ranging from 10° to 100° C. to give a compound (VId). When necessary, the said compound was made into a corresponding salt with a suitable acid (e.g. hydrochloric acid or oxalic acid). The foregoing Production Method 2 is shown in Scheme 11:

Scheme 11

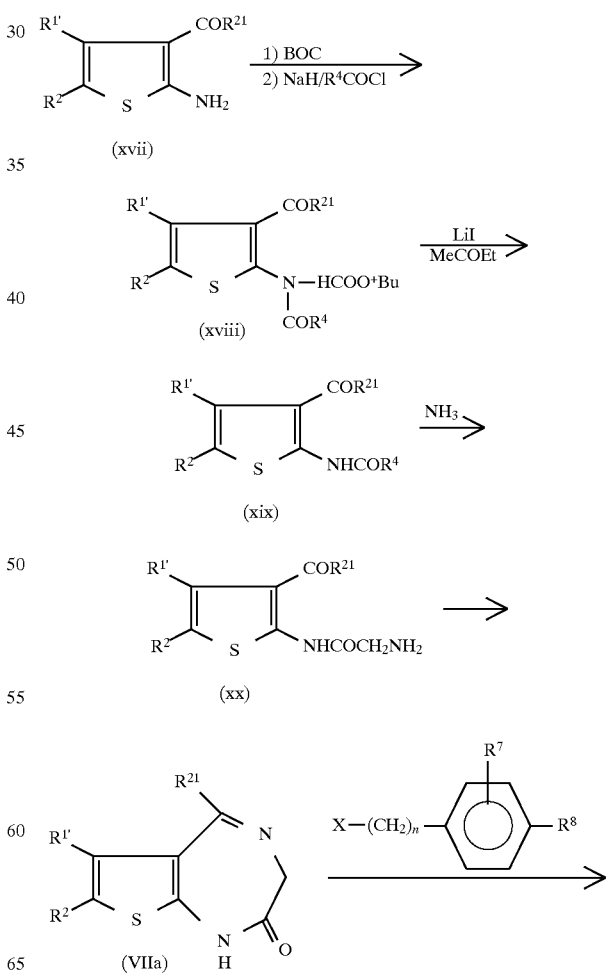

-continued
Scheme 11

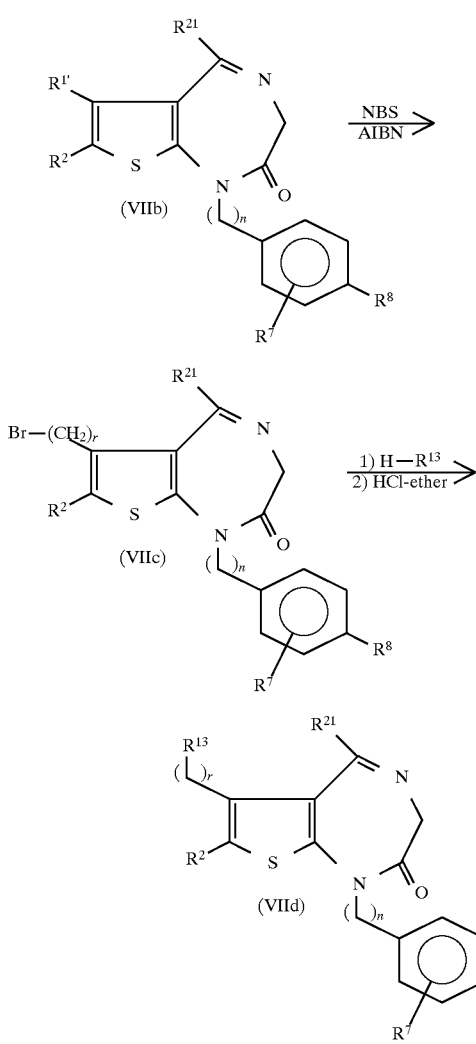

wherein each symbol is of the same meaning as defined above.

[Production Method 12]

The amino group of a 2-aminothiophene derivative producible by the method described in Production Method 1 was protected (e.g. Boc), which was stirred together with a halogenated aralkyl derivative, in the presence of a base (e.g. organic bases including potassium carbonate, pyridine and triethylamine), in a solvent which does not affect adversely on the reaction (e.g. amides including dimethylformamide and dimethylacetamide), at temperatures ranging from about 10° to 100° C., to give a derivative (xxi), which was subjected to alkali hydrolysis with a suitable alkali (e.g. sodium hydroxide) in a suitable solvent (e.g. methanol, tetrahydrofuran), and, the derivative thus produced was stirred together with DPPA in a solvent which does not affect adversely on the reaction (e.g. toluene, tetrahydrofuran, dimethylformamide, dimethylacetamide, ethanol) at temperatures ranging from about 0° to 100° C., and the resultant was made into a carbamic acid ester derivative (xxii) with a suitable alcohol (e.g. ethanol). The said derivative was stirred, in the presence of a base (e.g. sodium ethoxide), in a solvent which does not affect adversely on the reaction (e.g. dimethylformamide, dimethylacetamide), at temperatures ranging from about 0° to 100° C. to give a thieno[2,3-d] imidazol-2-one derivative (VIIe). The said compound was stirred together with a halogenated alkyl derivative, in the presence of a base, in a solvent which does not affect adversely on the reaction (e.g. amides including dimethylformamide, dimethylacetamide), at temperatures ranging from about 0° to 100° C. to give a compound (VIIf). Subsequently, the said compound (VIIf) was stirred, together with N-bromosuccinimide (NBS), in a solvent which does not affect adversely on the reaction (e.g. halogenated hydrocarbons including carbon tetrachloride and chloroform), in the presence of α,α'-azobisisobutyronitrile, at temperatures ranging from about 30° to 100° C. to give a compound (VIIg). The said compound was further stirred, together with various amine, in the presence of a base, in a solvent which does not affect adversely on the reaction (e.g. amides including dimethylformamide and dimethylacetamide, nitriles including acetonitrile, alcohols including ethanol), at temperatures ranging from about 10° to 100° C. to produce a compound (VIIh). The said compound, when necessary, was made into a corresponding salt with a suitable acid (e.g. hydrochloric acid, oxalic acid). The foregoing Production Method 12 is shown in Scheme 12:

Scheme 12

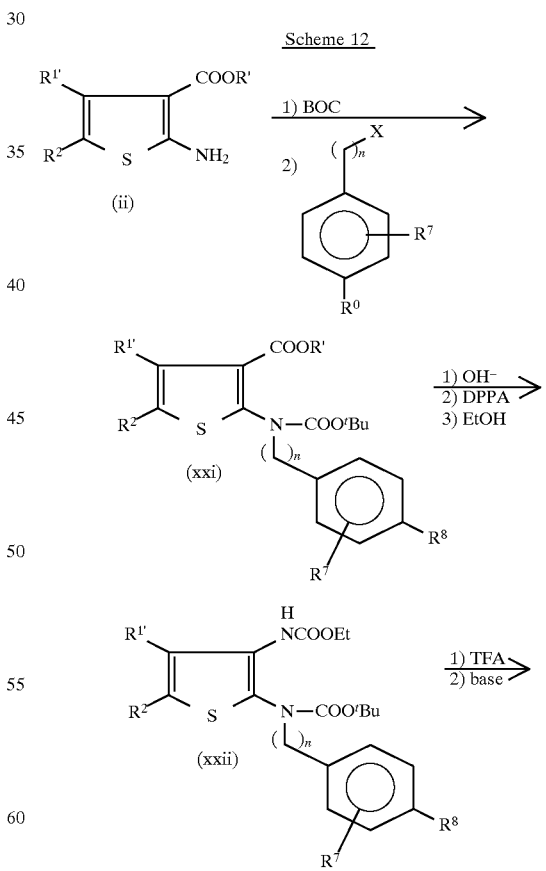

-continued
Scheme 12

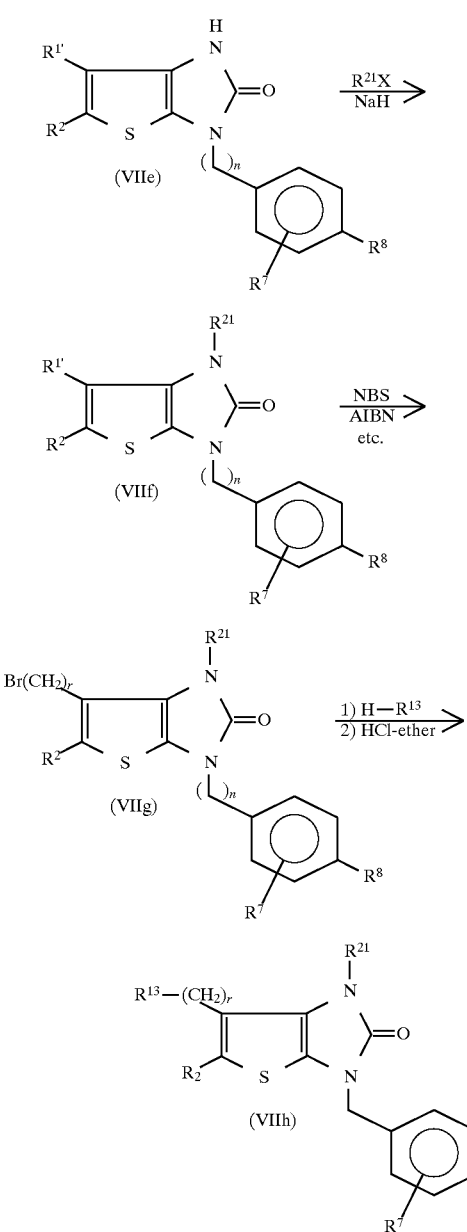

wherein each symbol is of the same meaning as defined above.

[Production Method 13]

Starting from a 2-aminothiophene derivative (ii) producible by the method described in Production Method 1 or a salt thereof, 4,5-dihydro-7-hydroxy-5-oxothieno [3,2-b] pyridine-6-carboxylic acid ethyl derivative (VIIj) was produced by the method of J. M. Barker et al. [J. Chem. Res. (M), 1980, 113; J. Chem. Res. (s), 6(1980)]. More specifically, the 2-aminothiophene derivative (ii) or a salt thereof was allowed to react with malonic acid ester to give the compound (xxii), which was stirred, in the presence of a suitable base (e.g. sodium hydride), in a solvent which does not affect adversely on the reaction (e.g. amides including dimethylformamide and dimethyl acetamide), at temperatures ranging from 10° to 100° C. to give the derivative (VIIj). The said derivative (VIIj) was stirred, together with a halogenated aralkyl derivative, in the presence of a base (e.g. organic bases including potassium carbonate, pyridine and triethylamine), in a solvent which does not affect adversely on the reaction (e.g. amides including dimethylformamide and dimethyl acetamide), at temperatures ranging from 10° to 100° C. to give a derivative (VIIk), and,the said derivative was stirred, together with N-bromosuccinimide (NBS), in a solvent which does not affect adversely on the reaction (e.g. halogenated hydrocarbons including carbon tetrachloride and chloroform), in the presence of α,α'-azobisisobutyronitrile, at temperatures ranging from about 30° to 100° C. to give the compound (VIIm). Further, the said compound was stirred, together with various amines, in the presence of a base, in a solvent which does not affect adversely on the reaction (e.g. amides including dimethylformamide and dimethyl acetamide, nitriles including acetonitrile, alcohols including ethanol), at temperatures ranging from about 10° to 100° C. to produce the compound. (VIIn). When necessary, the said compound was made into a corresponding salt with a suitable acid (e.g. hydrochloric acid, oxalic acid). The foregoing Production Method 13 was shown in Scheme 13:

Scheme 13

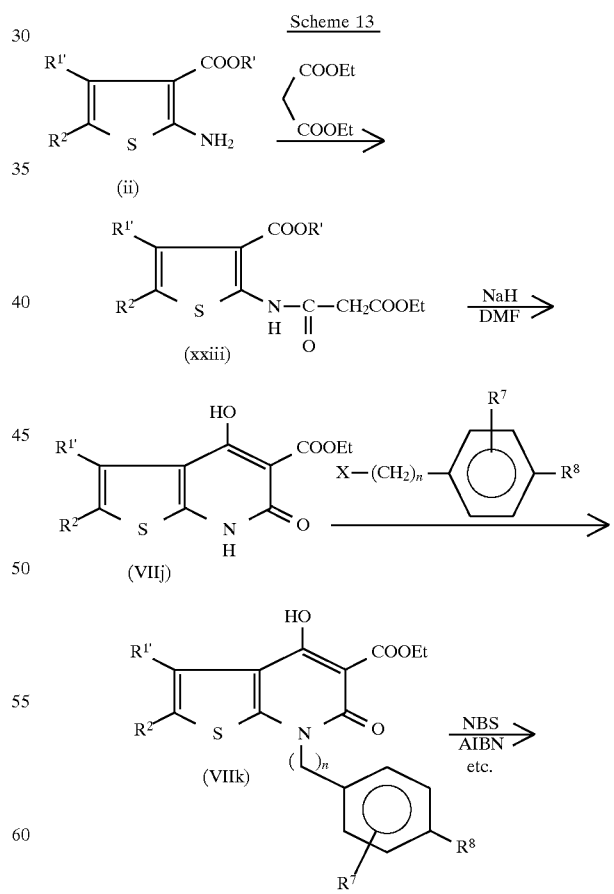

-continued
Scheme 13

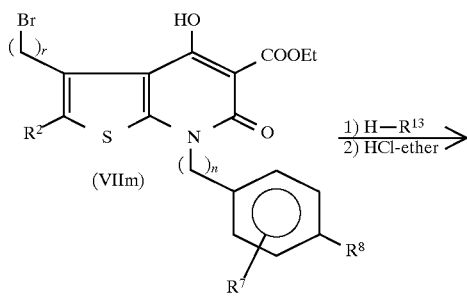

(VIIm)

(VIIn)

wherein each symbol is of the same meaning as defined above.

[Production Method 14]

In a suitable solvent which does not affect adversely on the reaction (e.g. halogenated hydrocarbons including dichloromethane, and ethers including tetrahydrofuran, ethyl ether and dioxane), the 1,4-dihydro-4-oxoquinoline-3-carboxylic acid ester derivative (Va') was stirred, together with an aluminum amide derivative produced from a suitable aluminum reagent [e.g. trimethyl aluminum, triethyl aluminum or diisobutyl aluminum hydride (DIBAL)] and amines, at temperatures ranging from 10° to 100° C. to give a 1,4-dihydro-4-oxoquinoline-3-carboxylic acid amide derivative (Va"). The said derivative was stirred, together with a Grignard reagent, in a suitable solvent (e.g. tetrahydrofuran and ethyl ether) at temperatures ranging from 0° to 80° C. to give a corresponding ketone derivative (Vc). The above production method 14 is shown in Scheme 14:

Scheme 14

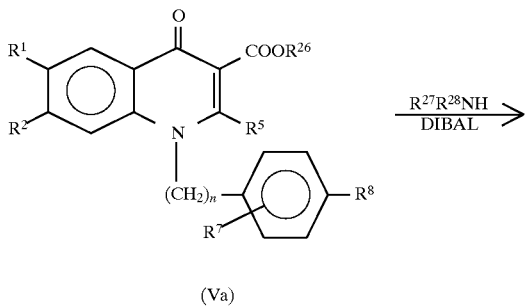

(Va)

-continued
Scheme 14

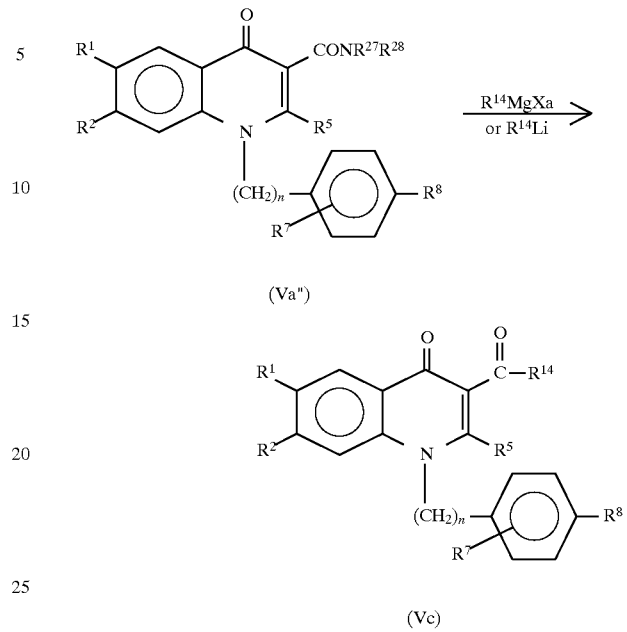

(Va")

(Vc)

wherein $R^{26}$ is alkyl or aryl, $R^{27}$ and $R^{28}$ are each hydrogen or hydrocarbon residue, and other symbols are of the same meaning as defined in the foregoing.

The alkyl and aryl shown by the above-mentioned $R^{26}$ is of the same meaning as defined in the foregoing.

The hydrocarbon residues shown by the above-mentioned $R^{27}$ and $R^{28}$ are of the same meaning as the hydrocarbon residue in the optionally substituted carbonyl group with a hydrocarbon residue shown by the above-mentioned R'.

[Production Method 15]

In a suitable solvent which does not affect adversely on the reaction (e.g. halogenated hydrocarbons including dichloromethane, and ethers including tetrahydrofuran, ethyl ether and dioxane), 1,4-dihydro-4-oxopyrido [2,3-b] pyridine-3-carboxylic acid ester derivative (Vd) is stirred, together with an aluminum amide derivative produced from a suitable aluminum reagent [e.g. trimethyl aluminum, triethyl aluminum and diisobutyl aluminum hydride (DIBAL)] and amines, at temperatures ranging from 10° to 100° C. to give a 1,4-dihydro-4-oxopyrido[2,3-b]pyridine-3-carboxylic acid amide derivative (Vd'). The said derivative is stirred, together with a Grignard reagent, in a suitable solvent which does not affect adversely on the reaction (e.g. tetrahydrofuran and ethyl ether), at temperatures ranging from about 0° to 80° C. to give a corresponding ketone derivative (Ve). The production method is shown in Scheme 15:

Scheme 15

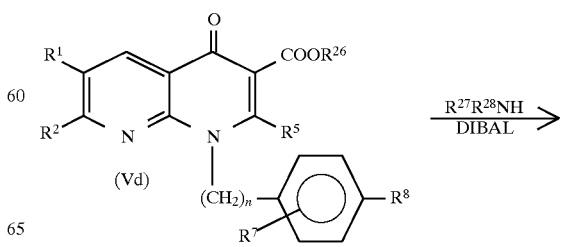

(Vd)

-continued
Scheme 15

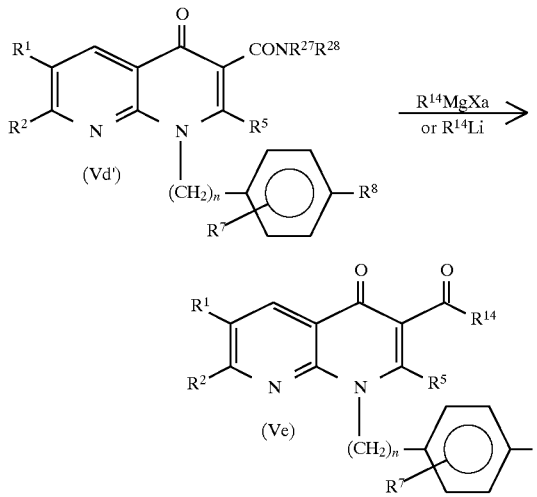

wherein $R^{26}$ is alkyl or aryl, $R^{27}$ and $R^{28}$ are each hydrogen or hydrocarbon residue, and other symbols are of the same meaning as defined above.

The alkyl and aryl shown by the above $R^{26}$ are of the same meaning as defined above.

The hydrocarbon residue shown by the above $R^{27}$ and $R^{28}$ is of the same meaning as the hydrocarbon residue in the carbonyl group optionally substituted with hydrocarbon residue shown by the above-mentioned R'.

[Production Method 16]

In a suitable solvent which does not affect adversely on the reaction (e.g. ethers including 1,2-dimethoxyethane, tetrahydrofuran and dioxane and alcohols including ethyl alcohol). To the solution is added, in the presence of equimolar to an excess amount (2 to 10 equivalents) of a suitable base (e.g. sodium carbonate), a suitable aryl boric acid derivative (e.g. phenyl boric acid, 3-methoxyphenyl boric acid and 4-ethoxycarbonyl phenyl boric acid). To the mixture is added, in the streams of an inert gas (e.g. argon gas), a suitable catalyst [e.g. palladium metal including tetrakis (triphenylphosphine) palladium]. The mixture is stirred for a period ranging from several minutes to several hours at temperatures ranging from about 10° to 100° C. Insolubles are removed to leave the desired derivative (Iq). The foregoing production method 16 is shown in Scheme 16:

Scheme 16

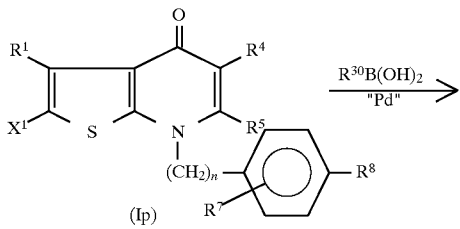

-continued
Scheme 16

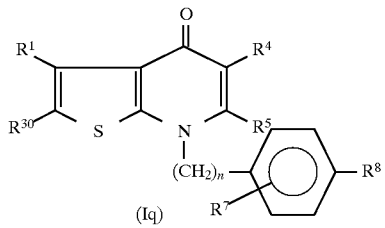

wherein $R^{30}$ is an optionally substituted aryl group, and other symbols are of the same meaning as defined above.

As salts of the compounds of this invention obtained thus above, physiologically acceptable acid addition salts are preferable. Examples of such salts include those with an inorganic acid (e.g. hydrochloric acid, hydrobromic acid, nitric acid, sulfuric acid and phosphoric acid) or those with an organic acid (e.g. formic acid, acetic acid, trifluoroacetic acid, fumaric acid, oxalic acid, tartaric acid, maleic acid, citric acid, succinic acid, malic acid, methanesulfonic acid, bezenesulfonic acid, and p-toluenesulfonic acid). Further, when the compound (I) of this invention has an acid group such as —COOH, the compound(I) may form a salt with an inorganic base (e.g. an alkali metal or alkaline earth metal such as sodium, potassium, calcium and magnesium; ammonia) or an organic base (e.g. trimethylamine, triethylamine, pyridine, picolin, ethanolamine, diethanolamine, triethanolamine, dicyclohexylamine and N,N'-dibenzylethylenediamine).

Especially preferable examples of the compounds or their salts of this invention include 3-(N-benzyl-N-methylaminomethyl)-4,7-dihydro-7-(2-methoxybenzyl)-2-(4-methoxyphenyl)-4-oxothieno[2,3-b]pyridine-5-carboxylic acid ethyl ester, (3-(N-benzyl-N-methylaminomethyl)-4,7-dihydro-7-(2-fluorobenzyl)-2-(4-methoxyphenyl)-4-oxothieno[2,3-b]pyridine-5-carboxylic acid ethyl ester, 2-(4-acetylaminophenyl)-3-(N-benzyl-N-methylaminomethyl)-4,7-dihydro-7-(2-fluorobenzyl)-4-oxothieno[2,3-b]pyridine-5-carboxylic acid ethyl ester, 5-benzylmethylaminomethyl-1-(2-chloro-6-fluorobenzyl)-2,4(1H,3H)-dioxo-6-(4-methoxyphenyl)-3-phenylthieno[2,3-d]pyrimidine, 5-benzoul-3-(N-benzyl-N-methylaminomethyl)-7-(2,6-difluorobenzyl)-4,7-dihydro-4-oxo-2-(4-propionylaminophenyl)thieno[2,3-b]pyridine, 5-benzoyl-3-(N-benzyl-N-methylaminomethyl)-7-(2,6-difluorobenzyl)-4,7-dihydro-2-(4-N'-methylureidophenyl)-4-oxothieno[2,3-b]pyridine, 3-(N-benzyl-N-methylaminomethyl)-7-(2,6-difluorobenzyl)-4,7-dihydro-5-isobutyryl-4-oxo-2-(4-propionylaminophenyl)thieno[2,3-b]pyridine, 3-(N-benzyl-N-methylaminomethyl)-7-(2,6-difluorobenzyl)-4,7-dihydro-2-5-isobutyryl-(4-N'-methylureidophenyl)-4-oxothieno[2,3-b]pyridine, 3-(N-benzyl-N-methylaminomethyl)-7-(2,6-difluorobenzyl)-4,7-dihydro-2-(4-N'-methylureidophenyl)-4-oxothieno[2,3-b]pyridine-5-(N-isopropyl)carboxamide, 3-(N-benzyl-N-methylaminomethyl)-7-(2,6-difluorobenzyl)-4,7-dihydro-2-(4-N'-methylureidophenyl)-4-oxothieno[2,3-b]pyridine-5-(N-isopropyl-N-methyl)carboxamide, 3-(N-benzyl-N-methylaminomethyl)-7-(2,6-difluorobenzyl)-4,7-dihydro-2-(4-N'-methylureidophenyl)-4-oxothieno[2,3-b]pyridine-5-(N-benzyl-N-methyl)carboxamide or their salts.

The compounds or salts thereof of the present invention produced thus above can be isolated and purified by a conventional separating means such as recrystallization, distillation and chromatography. In the case where the compound (I) is produced in the free form, it can be converted to a salt thereof by a per se conventional means or a method analogous thereto. On the contrary, when it is obtained in the form of a salt, it can be converted to its free form or to any other salt.

In the case where the compound or a salt thereof of the present invention is an optically active compound, it can be separated into d-compound and l-compound by means of a conventional optical resolution.

Since the compounds of this invention have a GnRH antagonistic activity and low in toxicity, they can be safely used for the therapy of male hormone or female hormone dependent diseases as well as the therapy of diseases caused by excess secretion of these hormones, in warm-blooded animals (e.g. human, monkey, cow, horse, dog, cat, rabbit, rat and mouse), suppressing the secretion of gonadotropic hormone by the action of GnRH receptor antagonistic action. More specifically, the compounds of this invention are effective as a prophylactic or therapeutic agent for the prevention or treatment of several hormone dependent diseases, for example, a sex hormone dependent cancer (e.g. prostate cancer, cancer of the uterine cervix, breast cancer, pituitary adenoma), benign prostatic hypertrophy, myoma of the uterus, endometriosis, precocious puberty, amenorrhea, premenstrual syndrome, polycystic ovary syndrome and acne vulgaris. And, the compounds of this invention are also effective as a fertility controlling agent in both sexes (e.g. pregnancy controlling agents and menstrual cycle controlling agents). The compounds of this invention can be further used as a contraceptive of male or female and, as an ovulation-inducing agent of female. The compound of this invention can be used as an infertility treating agent by using a rebound effect owing to a stoppage of administration thereof. Further, the compounds of this invention are useful as modulating estrous cycles in animals in the field of animal husbandry, and as an agent for improving the quality of edible meat or promoting the growth of animals. Besides, the compounds of this invention are useful as an agent of spawning promotion in fish. While the compounds of this invention can be used singly, they can also effectively be used by administering in combination with a steroidal or non-steroidal antiandrogenic agent. The compound of this invention can be used for the suppressing a passing ascent of testosterone concentration in plasma, the ascent which occurs in administration of GnRH super antagonist such as leuprorelin acetate. The compound of this invention can effectively be used by administering in combination with a chemoterapeutic agent for cancer. In treatment of prostate cancer, examples of the chemoterapeutic agent include Ifosfamide, UFT, Adriamycin, Peplomycin, Cisplatin and the like. In treatment of breast cancer, examples of the chemoterpeutic agent include Cyclophohamide, 5—FU—, UFT, Methotrexate, Adriamycin, Mitomycin C, Mitoxantrone and the like.

When the compound of this invention is employed, in the field of animal husbandry or fisheries, as prophylactic and therapeutic agents of the above-mentioned diseases, is can be administered orally or non-orally in accordance with per se known means. It is mixed with a pharmaceutically acceptable carrier and usually administered orally as a solid preparation such as tablet, capsule, granule or powder, or non-orally as intravenous, subcutaneous or intramuscular injection, or as suppository or sublingually administrable tablet. Further, it is sublingually, subcutaneously or intramuscularly administered as a prolonged release formulation such as sublingually administrable tablets, or microcapsules. The daily dose varies with the degree of affliction; age, sex, body weight and difference of sensitivity of the subject to be administered; the time and intervals of administration, properties, dosage forms and kinds of the medicinal preparation; and kinds of the effective components, and it ranges usually, though not specifically limited, from about 0.01 to 10 mg, preferably from about 0.02 to 2 mg, more preferably from about 0.01 to 1 mg, relative to 1 kg body weight of warm-blooded animals, which is administered usually once daily or by 2 to 4 divided dosages. The daily dose when used in the field of animal husbandry or fishery varies with the conditions analogous to those mentioned above, it ranges, relative to 1 kg body weight of the subject animal or fish, from about 0.001 to 5 mg, preferably from about 0.002 to 2 mg, once or 2 to 3 divided dosages.

As the above-mentioned pharmaceutically acceptable carriers, conventional various organic or inorganic carriers are used, and they are incorporated as excipients, lubricants, binders and disintegrants in solid compositions; and as solvents, solubilisers, suspending agents, isotonizing agents, buffering agents and pain-easing agents in liquid compositions. And, depending on necessity, further additives such as preservatives, anti-oxidants, coloring agents and sweeteners can also be used.

Preferable examples of the above-mentioned excipients include lactose, sugar, D-mannito, starch, crystalline cellulose and more volatile silicon dioxide. Preferable examples of above-mentioned lubricants include magnesium stearate, calcium stearate, talc and colloid silica. Preferable examples of the above-mentioned binders include crystalline cellulose, sugar, D-mannitol, dextrin, hydroxypropyl cellulose, hydroxymethyl cellulose and polyvinyl pyrrolidone. Preferable examples of the above-mentioned disintegrants include starch, carboxymethyl cellulose, carboxymethyl cellulose calcium, cross carmelose sodium, cross carmelose sodium and carboxymethyl starch sodium. Preferable examples of the above-mentioned solvents include water for injection, alcohol, propylene glycol, macrogol, sesame oil and corn oil. Preferable examples of the above-mentioned solubilizers include polyethylene glycol, propylene glycol, D-mannitol, benzyl benzoate, ethanol, tris-aminomethane, cholesterol, triethanolamine, sodium carbonate and sodium citrate. Preferable examples of the above-mentioned suspending agents include surfactants such as stearyl triethanolamine, sodium lauryl sulfate, lauryl aminopropionic acid, lecithin, benzalkonium chloride, benzetonium chloride and monostearic glyceryl ester; and hydrophilic polymers such as polyvinyl alcohol, polyvinyl pyrrolidone, sodium carboxymethyl cellulose, methyl cellulose, hydroxymethyl cellulose, hydroxyethyl cellulose and hydroxypropyl cellulose. Preferable examples of the above-mentioned isotonizing agents include sodium chloride, glycerin and D-mannitol. Preferable examples of the above-mentioned buffering agents include buffer solutions such as phosphate, acetate, carbonate and citrate. Preferable examples of the above-mentioned pain-easing agents include benzyl alcohol. Preferable examples of the above-mentioned preservatives include para-hydroxybenzoic acid esters, chlorobutanol, benzyl alcohol, phenethyl alcohol, dehydroacetic acid and sorbic acid. Preferable examples of the above-mentioned anti-oxidants include sulfite and ascorbic acid.

To the compound of this invention, are added, for example, a suspending agent, a solubilizer, a stabilizer, an isotonizing agent and a preservative, then the mixture is formulated, in accordance with a per se known method, into an intravenous, subcutaneous or intramuscular injection. These injections can be processed into lyophilized preparations, when necessary, by a per se known method.

Examples of the above-mentioned pharmaceutical composition are oral agents (e.g. diluted powders, granules, capsules and tablets), injections, dropping injections, external agents (e.g. transnasal preparations, percutaneous preparations, etc.), ointments (e.g. rectal ointment, vaginal ointment, etc.) and the like.

Such pharmaceutical compositions can be manufactured by a per se known method commonly used in preparing pharmaceutical compositions.

The compound of the present invention or a salt thereof can be made into injections either in a form of an aqueous injection together with dispersing agents [e.g. Tween 80 (Atlas Powder, U.S.A.), HCO 80 (Nikko Chemicals, Japan), polyethylene glycol, carboxymethylcellulose, sodium alginate, etc.], preservatives (e.g. methyl paraben, propyl paraben, benzyl alcohol, etc.), isotonizing agents (e.g. sodium chloride, mannitol, sorbitol, glucose, etc.) and the like or in a form of an oily injection by dissolving, suspending or emulsifying in plant oil (e.g. olive oil, sesame oil, cotton seed oil, corn oil, etc.), propylene glycol and the like.

In preparing a pharmaceutical composition for oral use, the compound of the present invention or a salt thereof is molded by compressing, for example, with fillers (e.g. lactose, sucrose, starch, etc.), disintegrating agents (e.g. starch, calcium carbonate, etc.), binders (e.g. starch, gum arabic, carboxymethylcellulose, polyvinylpyrrolidone, hydroxypropylcellulose, etc.) or lubricants (e.g. talc, magnesium stearate, polyethylene glycol 6000, etc.) and the like. If necessary, the composition is coated by a per se known method with an object of masking the taste, enteric coating or long-acting. Examples of the coating agent therefore are hydroxypropylmethylcellulose, ethylcellulose, hydroxymethylcellulose, hydroxypropylcellulose, polyoxyethylene glycol, Tween 80, pluronic F 68, cellulose acetate phthalate, hydroxypropylmethylcellulose phthalate, hydroxymethylcellulose acetate succinate, Eudragit (a copolymer of methacrylic acid with acrylic acid; manufactured by Rohm, Germany), red oxide of iron and the like. Subcoating layer may be provided between the enteric coating and the core according to per se known method.

In preparing an external composition, the compound of the present invention or a salt thereof as it is or a salt thereof is subjected to a per se known method to give a solid, semisolid or liquid agent for external use. For example, the solid preparation is manufactured as follows. Thus, the compound of the present invention as it is or after adding/mixing fillers (e.g. glycol, mannitol, starch, microcrystalline cullulose, etc.), thickeners (e.g. natural gums, cellulose derivatives, acrylic acid polymers, etc.) and the like thereto/therewith is made into a powdery composition. With respect to the liquid composition, an oily or aqueous suspension is manufactured by the manner nearly the same as in the case of the injection. In the case of a semisolid composition, the preferred one is an aqueous or oily gel or an ointment. Each of them may be compounded with a pH adjusting agent (e.g. carbonic acid, phosphoric acid, citric acid, hydrochloric acid, sodium hydroxide, etc.), an antiseptic agent (e.g. p-hydroxybenzoates, chlorobutanol, benzalkonium chloride, etc.) and the like.

In the manufacture of an ointment for example, the compound of the present invention or a salt thereof can be made into an oily or an aqueous solid, semisolid or liquid ointment. Examples of the oily base material applicable in the above-mentioned composition are glycerides of higher fatty acids [e.g. cacao butter, Witepsols (manufactured by Dynamite-Nobel), etc.], medium fatty acids [e.g. Miglyols (manufactured by Dynamite-Nobel), etc.] and plant oil (e.g. sesame oil, soybean oil, cotton seed oil, etc.) and the like. Examples of the aqueous base material are polyethylene glycols and propylene glycol and those of the base material for aqueous gel are natural gums, cellulose derivatives, vinyl polymers, acrylic acid polymers, etc.

BEST MODE FOR CARRYING OUT OF THE INVENTION

By way of the following Reference Examples, Working Examples and Test Examples, the present invention will be described more specifically, but they are not intended to limit the scope of this invention thereto.

$^1$H-NMR spectra were taken with the Varian GEMINI 200 (200 MHz) type spectrometer, JEOL LAMBDA300 (300 MHz) type spectrometer or the Brucker AM 500 (500 MHz) type spectrometer, employing tetramethylsilane as the internal standard. All delta values were expressed in ppm.

The symbols used in the present specification have the following meanings:

s: singlet, d: doublet, t: triplet, dt: double triplet, m: multiplet, br: broad

Reference Example 1

2-Amino-5-phenylthiophene-3-carboxylic acid ethyl ester

To a mixture of ethyl cyanoacetate (6.1 g, 50 mmol), sulfur (1.61 g, 50 mmol) triethylamine (3.5 ml, 25 mmol) and dimethylformamide (10 ml) was added dropwise, with stirring at 45° C., phenylacetaldehyde (50% diethylphthalate solution; 12.05 g, 50 mmol) for 20 minutes. The mixture was stirred for 9 hours at 45° C., and the reaction mixture was concentrated. The resulting residue was extracted with ethylacetate. The extract was washed with an aqueous sodium chloride solution, which was then dried (MgSO$_4$), followed by distilling off the solvent under reduced pressure. The residue was chromatographed on silica gel, followed by crystallization from ether-hexane to give slightly yellow plates (5.55 g, 45%), m.p.124.5°–125.5° C. (value in literature reference 123°–124° C.).

| Elemental Analysis for $C_{13}H_{13}NO_2S$: | | | |
|---|---|---|---|
| | C(%) | H(%) | N(%) |
| Calcd. | 63.13 | 5.30 | 5.66 |
| Found | 62.99 | 5.05 | 5.63 |

$^1$H-NMR (200 MHz, CDCl$_3$) δ: 1.37(3H,t,J=7.1 Hz), 4.30(2H,d,J=7.1 Hz), 5.97(2H,br), 7.17–7.46(6H,m). IR(KBr): 3448, 3320, 1667, 1590, 1549 cm$^{-1}$.

Reference Example 2

2-Amino-4-methyl-5-(4-methoxyphenyl)thiophene-3-carboxylic acid ethyl ester

A mixture of 4-methoxyphenylacetone (16.5 g, 0.10 mol), ethyl cyanoacetate (12.2 g, 0.10 mol), ammonium acetate (1.55 g, 20 mmol), acetic acid (4.6 ml, 80 mmol) and benzene (20 ml) was heated for 24 hours under reflux, while removing water produced in the reaction mixture using a Dean and Stark apparatus. After cooling, the reaction mixture was concentrated under reduced pressure. The residue was partitioned between dichloromethane and an aqueous sodium hydrogencarbonate solution. The organic layer was washed with an aqueous sodium chloride solution, which was then dried (MgSO$_4$), followed by distilling of the solvent under reduced pressure. To an ethanol (30 ml) solution of the residue were added sulfur (3.21 g, 0.10 mol)

and diethylamine (10.4 ml, 0.10 mol). The mixture was stirred at 50°–60° C. for 2 h and then concentrated, and the concentrate was extracted with ethyl acetate. The extract was washed with an aqueous sodium chloride solution and dried (MgSO$_4$), followed by distilling off the solvent under reduced pressure. The residue was chromatographed on silica gel, which was the crystallized from ether-hexane to give a pale yellow plates (11.5 g, 40%), m.p.79°–80° C.

| Elemental Analysis for C$_{15}$H$_{17}$NO$_3$S: | | | | |
|---|---|---|---|---|
| | C(%) | H(%) | N(%) | S(%) |
| Calcd. | 61.83 | 5.88 | 4.81 | 11.01 |
| Found | 61.81 | 5.75 | 4.74 | 10.82 |

$^1$H-NMR (200 MHz, CDCl$_3$) δ: 1.37(3H,t,J=7.1 Hz), 2.28(3H,s), 3.83(3H,s), 4.31(2H,q,J=7.1 Hz), 6.05(2H,brs), 6.91(2H,d,J=8.8 Hz), 7.27(2H,d,J=8.8 Hz). IR(KBr): 3426, 3328, 1651, 1586, 1550, 1505, 1485 cm$^{-1}$. FAB-MS m/z: 291(M$^+$)

Reference Example 3

Employing various acetone derivatives in place of 4-methoxyphenylacetone, compounds shown in Table 1 were produced in accordance with substantially the same manner as described in Reference Example 2.

TABLE 1

| R. Ex. 3 Cpd. No. | R$^{20}$ | R$^{21}$ | Yield (%) | m.p. (°C.) |
|---|---|---|---|---|
| 1 | methyl | phenyl | 40 | 64–65 |
| 2 | methyl | 2-methoxyphenyl | 12 | 70–71 |

Reference Example 4

{3-Ethoxycarbonyl-5-(4-methoxyphenyl)-4-methylthiophen-2-yl}aminomethylene malonic acid diethyl ester To the compound produced in Reference Example 2 (10 g, 343.3 mmol) was added diethyl ehoxymethylene malonate (7.45 g, 34.5 mmol). The mixture was stirred for 2 hours at 120° C. After cooling, to the reaction mixture was added ether to precipitate crystals. The crystals were collected by filtration and washed with ether once more, followed by drying over phosphorus pentaoxide under reduced pressure to give pale yellow crystals (14.2 g, 90%), m.p.122°–123° C.

$^1$H-NMR (200 MHz, CDCl$_3$) δ: 1.32(3H,t,J=7.1 Hz), 1.38(3H,t,J=7.2 Hz), 1.41(3H,t,J=7.2 Hz), 2.34(3H,s), 3.85 (3H,s), 4.25(2H,q,J=7.1 Hz), 4.38(2H,q,J=7.2 Hz), 4.45(2H, q,J=7.2 Hz), 6.95(2H,d,J=8.8 Hz), 7.31(2H,d,J=8.8 Hz), 8.22(1H,d,J=13.4 Hz), 12.74(1H,d,J=13.1 Hz) IR(KBr): 2984, 1720, 1707, 1688, 1653, 1599, 1518, 1499 cm$^{-1}$.

Reference Example 5

Employing, as starting materials, compounds produced in Reference Example 3 or commercially available various thiophene compounds, in accordance with substantially the same manner as described in Reference Example 4, the compounds shown in Table 2 were produced.

TABLE 2

| R. Ex. 5 Cpd. No. | R$^{20}$ | R$^{21}$ | Yield (%) | m.p. (°C.) |
|---|---|---|---|---|
| 1 | methyl | phenyl | 92 | 108–109 |
| 2 | phenyl | methyl | 92 | 137–138 |
| 3 | methyl | H | 92 | 132–133 |
| 4 | methyl | 2-methoxyphenyl | 100 | amorphous |

Reference Example 6

{3-carboxy-5-(4-methoxyphenyl)-4-methylthiophen-2-yl}aminomethylene malonic acid diethyl ester To a solution of the compound produced in Reference Example 4 (7.0 g, 15.2 mmol) in dioxane (20 ml) was added a solution of potassium hydroxide (5.0 g, 75.7 mmol) in ethanol (30 ml) at 60°–70° C. with stirring. The mixture was stirred for one hour at the same temperature range, which was allowed to stand for one hour at room temperature. To the reaction mixture was added 2N HCl (40 ml, 80 mmol) with ice-cooling. The reaction mixture was concentrated under reduced pressure. Resulting yellow precipitate was collected by filtration, which was washed with a mixture of cold water and ethanol, followed by drying over phosphorus pentaoxide under reduced pressure to give a yellow powder (6.1 g, 93%), m.p. 184°–187° C.

$^1$H-NMR (200 MHz, DMSO-d$_6$) δ: 1.24(3H,t,J=7.1 Hz), 1.28(3H,t,J=7.2 Hz), 2.30(3H,s), 3.80(3H,s), 4.15(2H,q,J= 7.1 Hz), 4.24(2H,q,J=7.2 Hz), 7.03(2H,d,J=8.7 Hz), 7.37 (2H,d,J=8.7 Hz), 8.08(1H,d,J=13.6 Hz), 12.41(1H,d,J=13.6 Hz). IR(KBr): 3422, 2980, 1719, 1653, 1607, 1551, 1512 cm$^{-1}$.

Reference Example 7

Employing compounds obtained in Reference Example 5 as starting materials, in accordance with substantially the same manner as Reference Example 6, the compounds shown in Table 3 were produced.

TABLE 3

| R. Ex. 7 Cpd. No. | R$^{20}$ | R$^{21}$ | Yield (%) | m.p. (°C.) |
|---|---|---|---|---|
| 1 | methyl | phenyl | 98 | 187–190 |
| 2 | phenyl | methyl | 65 | 173–175 |
| 3 | methyl | H | 94 | 187–189 |
| 4 | methyl | 2-methoxyphenyl | 88 | 167–169 |

Reference Example 8

4-Hydroxy-2-(4-methoxyphenyl)-3-methylthieno[2,3-b] pyridine-5-carboxylic acid ethyl ester To polyphosphoric ester (PPE) (90 ml) was added the compound produced in Reference Example 6 (6.0 g, 13.8 mmol) in small portions at 190° C. with stirring.

The mixture was stirred for 30 minutes at the same temperature. The reaction mixture was poured into ice-water, which was subjected to extraction with ethylacetate. The extract solution was washed with an aqueous sodium chloride solution, which was then dried (MgSO$_4$), followed by distilling off the solvent under reduced pressure. The residue was chromatographed on silica gel to give a yellow powder (3.65 g, 77%). As the sample for elemental analysis, the powder was recrystallized from ethanol to give yellow crystals, m.p.162°–163° C.

| Elemental Analysis for C$_{18}$H$_{17}$NO$_4$S: | | | | |
|---|---|---|---|---|
| | C(%) | H(%) | N(%) | S(%) |
| Calcd. | 62.96 | 4.99 | 4.08 | 9.34 |
| Found | 62.89 | 5.04 | 4.01 | 9.34 |

$^1$H-NMR (200 MHz, CDCl$_3$) δ: 1.47(3H,t,J=7.1 Hz), 2.63(3H,s), 4.87(3H,s), 4.49(2H,q,J=7.1 Hz), 6.99(2H,d,J=8.8 Hz), 7.44(2H,d,J=8.8 Hz), 8.84(1H,s), 12.11(1H,s). IR(KBr): 3434, 2992, 1692, 1601, 1582, 1535, 1504 cm$^{-1}$. FAB-MS m/z: 344 (MH$^+$)

Reference Example 9

Employing compounds produced in Reference Example 7 as starting materials, in accordance with substantially the same manner as described in Reference Example 8, the compounds shown in Table 4 were produced.

TABLE 4

OH
R$^{20}$ ... COOC$_2$H$_5$
R$^{21}$ S N

| R. Ex. 9 Cpd. No. | R$^{20}$ | R$^{21}$ | Yield (%) | m.p. (°C.) |
|---|---|---|---|---|
| 1 | methyl | phenyl | 60 | 155–157 |
| 2 | phenyl | methyl | 69 | 146–147 |
| 3 | methyl | H | 21 | 175–177 |
| 4 | methyl | 2-methoxyphenyl | 73 | amorphous |

Reference Example 10

4-Hydroxy-2-(4-nitrophenyl)-3-methylthieno[2,3-b]pyridine-5-carboxylic acid ethyl ester To a solution of the compound 1 produced in Reference Example 9 (3.76 g, 12.0 mmol) in conc. sulfuric acid (10 ml) was added dropwise, a solution of sodium nitrate (1.27 g, 15.0 mmol) in conc. sulfuric acid (5 ml) with ice-cooling. The mixture was stirred for 30 minutes at the same temperature. The reaction mixture was poured into ice-water, which was subjected to extraction with chloroform. The extract was washed with an aqueous sodium chloride solution, which was then dried (MgSO$_4$), followed by distilling off the solvent under reduced pressure. The residue was chromatographed on silica gel to give a yellow powder, which was recrystallized from ethanol to afford yellow crystals (1.75 g, 41%), m.p.260°–261° C.

| Elemental Analysis for C$_{17}$H$_{14}$N$_2$O$_5$S: | | | |
|---|---|---|---|
| | C(%) | H(%) | N(%) |
| Calcd. | 56.98 | 3.94 | 7.82 |
| Found | 56.66 | 3.91 | 7.86 |

$^1$H-NMR (200 MHz, CDCl$_3$) δ: 1.49(3H,t,J=7.1 Hz), 2.70(3H,s), 4.51(2H,q,J=7.1 Hz), 7.70(2H,d,J=8.8 Hz), 8.34 (2H,d,J=8.8 Hz), 8.89(1H,s), 12.27(1H,s). IR(KBr): 3002, 1692, 1605, 1514, 1350, 1290 cm$^{-1}$. FAB-MS m/z: 358 (MH$^+$)

Reference Example 11

4-Hydroxy-5-hydroxymethyl-2-(4-methoxyphenyl)-3-methylthieno[2,3-b]pyridine

To a suspension (6 ml) of lithium aluminum hydride (0.0326 g, 0.87 mmol) in anhydrous tetrahydrofuran was added dropwise a solution of the compound produced in Reference Example 8 (0.20 g, 0.58 mmol) in anhydrous tetrahydrofuran (3 ml) at room temperatures (15°–35° C., the same range applies hereinafter). The mixture was then stirred for 30 minutes at room temperature, to which was added an aqueous solution of Rochelle salt. Resulting precipitate was removed by filtration. In this process, when necessary, the reaction mixture was subjected to heating under reflux to complete the reaction. The precipitate was washed with ethyl alcohol and chloroform, which was combined with the filtrate, followed by concentration under reduced pressure. The concentrate was partitioned between ethyl acetate and an aqueous sodium chloride solution. The organic layer was dried (MgSO$_4$), from which the solvent was distilled off under reduced pressure to give white crystals (0.13 g, 74%).

mp >300° C.; $^1$H-NMR (200 MHz, DMSO-d$_6$) δ: 2.55 (3H,s), 3.81(3H,s), 4.41(2H,s), 7.03(2H,d,J=8.8 Hz), 7.40 (2H,d,J=8.8 Hz), 7.75(1H,s) IR(KBr): 3210, 2930, 1613, 1506, 1255 cm$^{-1}$. FAB-MS m/z: 302 (MH$^+$)

Reference Example 12

2-Benzoyl-4-hydroxy-3-methylthieno[2,3-b]pyridine-5-carboxylic acid ethyl ester

To a mixture of the compound 3 produced in Reference Example 7 (5.0 g, 15.3 mmol) and anhydrous aluminum chloride (8.6 g, 64.5 mmol) in nitromethane (100 ml) was added dropwise gradually, in an atmosphere of nitrogen with ice cooling, benzoyl chloride (3.6 ml, 31.0 mmol). The mixture was stirred for one hour at room temperature and, then, for 14 hours at 50° C. The reaction mixture was poured into ice-water, followed by extraction with ethyl acetate. The extract was washed with an aqueous sodium chloride solution, which was dried (MgSO$_4$), then the solvent was distilled off under reduced pressure to give a brownish powder (7.58 g). The powder was added, in small portions, to polyphosphoric acid ester (PPE), while stirring at 120° C. The mixture was stirred for 90 minutes at the same temperature, which was then poured into ice-water, followed by extraction with ethyl acetate. The extract was washed with an aqueous sodium chloride solution and dried (MgSO$_4$), then the solvent was distilled off under reduced pressure. The residue was chromatographed on silica gel to give a yellow powder (0.82 g, 16%). As the sample for elemental analysis, the powdery product was recrystallized from chloroform-methanol to give a yellow crystals. m.p.241°–243° C.

Elemental Analysis for $C_{18}H_{15}NO_4S \cdot 0.25H_2O$:

|  | C(%) | H(%) | N(%) |
|---|---|---|---|
| Calcd. | 62.51 | 4.52 | 4.05 |
| Found | 62.77 | 4.22 | 4.30 |

$^1$H-NMR (200 MHz, $CDCl_3$-$CD_3OD$) δ: 1.49(3H,t,J=7.1 Hz), 2.71(3H,s), 4.53(2H,q,J=7.1 Hz), 7.49–7.70(3H,m), 8.96(1H,s). IR(KBr): 3004, 1692, 1638, 1603, 1582, 1537, 1431 $cm^{-1}$.

Reference Example 13

2-Phenylacetyl-4-hydroxy-3-methylthieno[2,3-b]pyridine-5-carboxylic acid ethyl ester Employing the compound 3 (10.0 g, 30.55 mmol) produced in Reference Example 7, in substantially the same manner as in Reference Example 12, using phenylacetyl chloride in place of benzoyl chloride, the above-titled compound (1.47 g, 14%) were produced. m.p.208°–214° C.

Elemental Analysis for $C_{19}H_{17}NO_4S \cdot 0.1EtOAc$:

|  | C(%) | H(%) | N(%) |
|---|---|---|---|
| Calcd. | 63.98 | 4.93 | 3.85 |
| Found | 64.25 | 4.66 | 3.52 |

$^1$H-NMR (200 MHz, $CDCl_3$-$CD_3OD$) δ: 1.47(3H,t,J=7.1 Hz), 2.99(3H,s), 4.20(2H,s), 4.49(2H,q,J=7.1 Hz), 7.26–7.41(5H,m), 8.96(1H,s), 12.50(1H,s). IR(KBr): 3424, 2986, 1694, 1601, 1580, 1535, 1495, 1439 $cm^{-1}$.

Reference Example 14

2-Bromo-4-hydroxy-3-methylthieno[2,3-b]pyridine-5-carboxylic acid ethyl ester

To a solution of the compound 3 produced in Reference Example 7 (17.8 g, 54.4 mmol) and pyridine (22 ml, 0.272 mmol) in chloroform (120 ml) was added dropwise gradually a solution of bromine (3.4 ml, 66.0 mmol) in chloroform (30 ml). The mixture was stirred for 40 minutes at room temperature, and then, the reaction mixture was concentrated under reduced pressure. To the concentrate was added dilute hydrochloric acid. The resulting crystalline precipitate was collected by filtration, which was washed with water and a small volume of cold ether, followed by drying over phosphorus pentaoxide under reduced pressure to give a brown powder (20 g). This powder was added, in small portions, to polyphosphoric acid ester (PPE) (100 ml) at 120° C. under stirring. The mixture was stirred for 90 minutes at the same temperature. The reaction mixture was then poured into ice-water, which was subjected to extraction with ethyl acetate. The extract was washed with an aqueous saline solution and dried ($MgSO_4$), then the solvent was distilled off under reduced pressure. The residue was chromatographed on silica gel to give a pale yellow powder (9.93 g, 58%). As the sample for elemental analysis,the powder was recrystallized from chloroformmethanol to give colorless needles, m.p.214°–216° C.

Elemental Analysis for $C_{11}H_{10}NO_3SBr$:

|  | C(%) | H(%) | N(%) |
|---|---|---|---|
| Calcd. | 41.79 | 3.19 | 4.43 |
| Found | 41.55 | 3.14 | 4.53 |

$^1$H-NMR (200 MHz, $CDCl_3$-$CD_3OD$) δ: 1.47(3H,t,J=7.1 Hz), 2.60(3H,s), 4.50(2H,q,J=7.1 Hz), 8.82(1H,s). IR(KBr): 2990, 1694, 1605, 1578, 1533 $cm^{-1}$.

Reference Example 15

2-Bromo-4-hydroxy-3-methylthieno[2,3-b]pyridine-5-carboxylic acid ethyl ester (alternative method of producing the compound produced in Reference Example 14)

A mixture of the compound 3 produced in Reference Example 9 (0.24 g, 1.01 rmnol), N-bromosuccinimide (10.198 g, 1.11 mol) and chloroform (10 ml) was refluxed for 3 hours. After cooling, the reaction mixture was poured into an aqueous sodium chloride solution, followed by extraction with chloroform. The extract was washed with an aqueous sodium chloride solution and dried ($MgSO_4$), then the solvent was distilled off under reduced pressure. The residue was chromatographed on silica gel to give a yellow powder, which was recrystallized from chloroformmethanol to give colorless needles (0.29 g, 91%). m.p.214°–216° C.

Reference Example 16

7-Benzoyl-4,7-dihydro-2-(4-methoxyphenyl)-3-methyl-4-oxothieno[2,3-b]pyridine-5-carboxylic acid ethyl ester To a solution of the compound produced in Reference Example 8 (5 g, 14.6 mmol) in pyridine (100 ml) was added, under ice-cooling, benzoyl chloride (1.78 ml, 15.3 mmol). After stirring for 150 minutes at room temperature, to the reaction mixture was added ethanol (1 ml). The mixture was concentrated under reduced pressure. The residue was partitioned between dichloromethane and a saturated aqueous sodium chloride solution. The aqueous layer was extracted with dichloromethane. The organic layers were combined, washed with water and dried ($MgSO_4$). The solvent was distilled off, and the residue was chromatographed on silica gel, which was crystallized from ethanol to give white crystals (6.41 g, 98%), m.p.110°–112° C.

Elemental Analysis for $C_{25}H_{21}NO_5S$:

|  | C(%) | H(%) | N(%) |
|---|---|---|---|
| Calcd. | 67.10 | 4.73 | 3.13 |
| Found | 66.95 | 4.68 | 2.93 |

$^1$H-NMR (200 MHz, $CDCl_3$) δ: 1.14(3H,t,J=7.7 Hz), 2.42(3H,s), 3.85(3H,s), 4.26(2H,q,J=7.2 Hz), 6.98(2H,d,J=6.7 Hz), 7.40(2H,d,J=8.9 Hz), 7.57(2H,t,J=7.6 Hz), 7.70 (1H,t,J=5.9 Hz), 8.27(2H,d,J=7.0 Hz), 9.14(1H,s). IR(KBr): 2972, 1717, 1607, 1580, 1522, 1502 $cm^{-1}$.

Reference Example 17

7-Benzoyl-3-bromomethyl-4,7-dihydro-2-(4-methoxyphenyl)-4-oxothieno[2,3-b]pyridine-5-carboxylic acid ethyl ester A mixture of the compound produced in Reference Example 16 (6.39 g, 14.3 mmol), N-bromosuccinimide (2.67 g, 15 mmol), α,α'-azobisisobutyronitrile (0.47 g, 2.86 mmol) and carbon tetrachloride (100 ml) was refluxed for one hour. Upon cooling, resulting insolubles were filtered off. The filtrate was diluted with chloroform. The organic layer was washed with a saturated aqueous sodium chloride solution and dried ($MgSO_4$), followed by distilling off the solvent under reduced pressure. The residue was crystallized from ethyl acetate to give colorless needles (7.02 g, 93%). m.p.124°–126° C.

Elemental Analysis for $C_{25}H_{20}NO_5SBr$:

|  | C(%) | H(%) | N(%) |
|---|---|---|---|
| Calcd. | 57.04 | 3.83 | 2.66 |
| Found | 57.16 | 3.85 | 2.70 |

$^1$H-NMR (200 MHz, CDCl$_3$) δ: 1.14(3H,t,J=7.2 Hz), 3.88(3H,s), 4.26(2H,q,J=7.2 Hz), 4.68(2H,s), 7.04(2H,d,J= 8.8 Hz), 7.53–7.75(5H,m), 8.35(2H,d,J=7.0 Hz), 9.20(1H,s). IR(KBr): 2984, 1717, 1605, 1502 cm$^{-1}$.

Reference Example 18

3-(N-Benzyl-N-methylaminomethyl)-4-hydroxy-2-(4-methoxyphenyl)-thieno[2,3-b]pyridine-5-carboxylic acid ethyl ester A mixture of the compound produced in Reference Example 17 (6.73 g, 12.8 mmol), N-ethyldiisopropylamine (2.30 ml, 13.4 mmol), N-benzylmethylamine (1.73 ml, 13.4 mmol) and dimethylformamide (100 ml) was stirred for 40 minutes at room temperature. The solvent was distilled off under reduced pressure, and the residue was partitioned between dichloromethane and a saturated aqueous sodium chloride solution. The organic layer was washed with water and dried (MgSO$_4$). The solvent was distilled off under reduced pressure, and the residue was dissolved with a mixture of dichloromethane (100 ml) and ethanol (50 ml). To the solution was added, under ice-cooling, a solution of sodium ethoxide (0.88 g, 13 mmol) in ethanol (50 ml), and the mixture was stirred for 4 hours at room temperature. The reaction mixture was neutralized with acetic acid, then the solvent was distilled off under reduced pressure. The residue was subjected to partition between dichloromethane and water. The organic layer was washed with water and dried (MgSO$_4$), then the solvent was distilled off under reduced pressure. The residue was chromatographed on silica gel, which was crystallized from ethanol to give colorless needles (4.32 g, 73%). m.p.175°–177° C.

Elemental Analysis for $C_{26}H_{26}N_2O_4S$:

|  | C(%) | H(%) | N(%) |
|---|---|---|---|
| Calcd. | 67.51 | 5.67 | 6.06 |
| Found | 67.43 | 5.72 | 6.06 |

$^1$H-NMR (200 MHz, CDCl$_3$) δ: 1.45(3H,t,J=7.2 Hz), 2.35(3H,s), 3.75(2H,brs), 3.89(3H,s), 3.92(2H,s), 4.44(2H, q,J=7.2 Hz), 7.01(2H,d,J=6.7 Hz), 7.21–7.37(7H,m), 8.87 (1H,s). IR(KBr): 3424, 3000, 1686, 1607, 1504 cm$^{-1}$.

Reference Example 19

2-Amino-4-methyl-5-(4-nitrophenyl)thiophene-3-carboxylic acid ethyl ester

In substantially the same procedure as described in Reference Example 1, using 4-nitrophenylacetone (35.0 g, 195 mmol) in place of 4-methoxyphenyl acetone, ethyl cyanoacetate (23 g, 19.5 mmol), ammonium acetate (3.1 g, 40 mmol), acetic acid (9.1 ml, 159 mmol), sulfur (5.0 g, 160 mmol) and diethylamine (16.0 ml, 160 mmol), the titled compound was produced as colorless crystals (22.2 g, 52%). m.p.168°–170° C. (recrystallized from ether-hexane).

Elemental Analysis for $C_{14}H_{14}N_2O_4S$:

|  | C(%) | H(%) | N(%) |
|---|---|---|---|
| Calcd. | 54.89 | 4.61 | 9.14 |
| Found | 54.83 | 4.90 | 9.09 |

$^1$H-NMR (200 MHz, CDCl$_3$) δ: 1.39(3H,t,J=7.1 Hz), 2.40(3H,s), 4.34(2H,q,J=7.1 Hz), 6.27(2H,brs), 7.48(2H,d, J=8.7 Hz), 8.23(2H,d,J=8.7 Hz). IR (KBr): 3446, 3324, 1667, 1580, 1545, 1506, 1491, 1475, 1410, 1332 cm$^{-1}$.

Reference Example 20

2,4(1H,3H)-Dioxo-5-methyl-6-(4-methoxyphenyl)-thieno [2,3-d]pyrimidin-3-acetic acid ethyl ester To a solution of the compound produced in Reference Example 1 (5.00 g, 17.20 mmol) was added ethyl isocyanatoacetate (2.90 ml, 25.80 mmol). The mixture was stirred for 6 hours at 45° C., followed by concentration under reduced pressure. The concentrate was dissolved in ethanol (6 ml), to which was added sodium ethoxide [prepared from ethanol (30 ml) and sodium (0.79 g, 34.30 mmol)]. The mixture was stirred for 24 hours at room temperature, to which was added 2N HCl (18 ml, 36 mmol). Ethanol was distilled off under reduced pressure, and the residue was subjected to filtration, which was washed with water-ethanol and dried under reduced pressure, followed by recrystallization from ethanol to give white needles (5.70 g, 89%). m.p.164°–165° C.

Elemental Analysis for $C_{18}H_{18}N_2O_5S$:

|  | C(%) | H(%) | N(%) |
|---|---|---|---|
| Calcd. | 57.74 | 4.85 | 7.48 |
| Found | 57.78 | 5.03 | 7.45 |

$^1$H-NMR (200 MHz, CDCl$_3$) δ: 1.30(3H,t,J=7.2 Hz), 2.45(3H,s), 3.85(3H,s), 4.26(2H,q,J=7.2 Hz), 4.78(2H,s), 6.95(2H,d,J=8.8 Hz), 7.31(2H,d,J=8.8 Hz), 10.58(1H,s). IR (KBr): 2914, 1742, 1713, 1655, 1605, 1568, 1528, 1499 cm$^{-1}$.

Reference Example 21

Employing, as starting materials, the compounds produced in Reference Examples 2, 3 and 19, compounds set forth in Table 5 were produced, in accordance with the method described in Reference Example 20.

TABLE 5

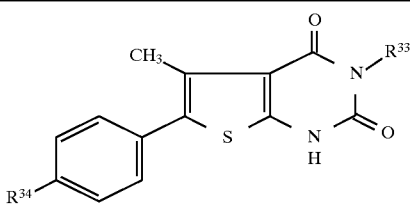

| R. Ex. 21 Cpd. No. | R$^{33}$ | R$^{34}$ | Yield (%) | m.p. (°C.) |
|---|---|---|---|---|
| 1 | ethyl acetate | H | 85 | 119–120 |
| 2 | methyl | methoxy | 84 | 273–276 |
| 3 | phenyl | methoxy | 85 | >300 |
| 4 | phenyl | nitro | 84 | >300 |
| 5 | benzyl | methoxy | 92 | 241–242 |

TABLE 5-continued

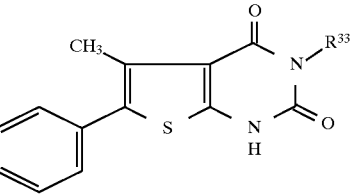

| R. Ex. 21 Cpd. No. | R³³ | R³⁴ | Yield (%) | m.p. (°C.) |
|---|---|---|---|---|
| 6 | 4-methoxyphenyl | methoxy | 99 | >300 |
| 7 | cyclohexyl | methoxy | 84 | 275–276 |
| 8 | 2-methoxyphenyl | methoxy | 81 | 257–258 |
| 9 | 3-methoxyphenyl | methoxy | 93 | >300 |
| 10 | 2-chlorophenyl | methoxy | 95 | 285–286 |
| 11 | 3-chlorophenyl | methoxy | 97 | >360 |
| 12 | 4-chlorophenyl | methoxy | 95 | >300 |

Reference Example 22
2,4(1H, 3H)-Dioxo-6-(4-nitrophenyl)-5-methylthieno[2,3-d]pyrimidin-3-acetic acid ethyl ester To the compound 1 produced in Reference Example 21 (2.20 g, 6.39 mmol) was added conc. sulfuric acid (12 ml). To the mixture was added dropwise, under ice-cooling, a solution of sodium nitrate (550 mg, 6.47 mmol) in conc. sulfuric acid, followed by stirring for one hour under ice-cooling. The reaction mixture was poured into ice-water, which was extracted with ethyl acetate. The extract was washed with an aqueous sodium chloride solution and dried (MgSO₄), followed by distilling off the solvent under reduced pressure. The residue was chromatographed on silica gel to give a yellowish solid (1.30 g, 52%), which was then recrystallized from ethyl acetate-hexane to yellow crystals, m.p.277°–280° C.

Elemental Analysis for $C_{17}H_{15}N_3O_6S.0.4H_2O$:

|  | C(%) | H(%) | N(%) |
|---|---|---|---|
| Calcd. | 51.48 | 4.01 | 10.59 |
| Found | 51.64 | 3.79 | 10.61 |

$^1$H-NMR (200 MHz, CDCl₃) δ: 1.33(3H,t,J=7.2 Hz), 2.56(3H,s), 4.28(2H,q,J=7.2 Hz), 4.79(2H,s), 7.57(2H,d,J=8.8 Hz), 8.30(2H,d,J=8.8 Hz), 10.30(1H,s). IR (KBr): 1748, 1719, 1663, 1522, 1460 cm⁻¹.

Reference Example 23
2,4(1H,3H)-Dioxo-1-(2-fluorobenzyl)-6-(4-nitrophenyl)-5-methylthieno[2,3-d]pyrimidin-3-acetic acid ethyl ester To a solution of the compound produced in Reference Example 22 (700 mg, 1.80 mmol) in dimethylformamide (10 ml) were added potassium carbonate (372 mg, 2.70 mmol), potassium iodide (299 mg, 1.80 mmol) and 2-fluorobenzyl chloride (0.43 ml, 3.60 mmol). The mixture was stirred for 2 hours at room temperature. The reaction mixture was concentrated, and the concentrate was partitioned between ethyl acetate and an aqueous sodium chloride solution. The aqueous layer was extracted with ethyl acetate. The combined extract was washed with an aqueous sodium chloride solution, which was then dried (MgSO₄), followed by distilling off the solvent under reduced pressure. The residue was chromatographed on silica gel to give a white powder (500 mg, 56%), m.p.155°–158° C.

Elemental Analysis for $C_{24}H_{20}N_3O_6SF.0.5H_2O$:

|  | C(%) | H(%) | N(%) |
|---|---|---|---|
| Calcd. | 56.91 | 4.18 | 8.30 |
| Found | 56.74 | 3.84 | 8.25 |

$^1$H-NMR (200 MHz, CDCl₃) δ: 1.32(3H,t,J=7.2 Hz), 3.84(3H,s), 4.27(2H,q,J=7.2 Hz), 4.84(2H,s), 5.30(2H,s), 7.06–7.33(4H,m), 7.54(2H,d,J=8.9 Hz), 7.27(2H,d,J=8.9 Hz). IR (KBr): 1748, 1711, 1673, 1520, 1491 cm⁻¹.

Reference Example 24

Starting from the compounds produced in Reference Example 21, compounds set forth in Table 6 were produced in accordance with the method described in Reference Example 23.

TABLE 6

| Ref. Ex. 24 Cpd. No. | R³³ | R³⁵ | R³⁴ | Yield (%) | m.p. (°C.) |
|---|---|---|---|---|---|
| 1 | ethyl acetate | 2-fluoro | methoxy | 87 | 127–128 |
| 2 | methyl | 2-methoxy | methoxy | 92 | 174–175 |
| 3 | methyl | 2-fluoro | methoxy | 97 | 179–180 |
| 4 | phenyl | 2-methoxy | methoxy | 93 | 240–241 |
| 5 | phenyl | 2-fluoro | methoxy | 96 | 252–253 |
| 6 | phenyl | 2-fluoro | nitro | 87 | 294–295 |
| 7 | phenyl | 3-fluoro | methoxy | 88 | 215–217 |
| 8 | phenyl | 4-fluoro | methoxy | 66 | 209–212 |
| 9 | phenyl | 2,4-difluoro | methoxy | 73 | 227–228 |
| 10 | phenyl | 2,6-difluoro | methoxy | 87 | 291–292 |
| 11 | phenyl | 2-chloro, 6-fluoro | methoxy | 91 | 287–288 |
| 12 | phenyl | 2-methylthio | methoxy | 81 | 239–240 |
| 13 | benzyl | 2-fluoro | methoxy | 86 | 124–126 |
| 14 | benzyl | 2,6-difluoro | methoxy | 82 | 161–163 |
| 15 | 4-methoxyphenyl | 2-fluoro | methoxy | 87 | 270–272 |
| 16 | 4-methoxyphenyl | 2,6-difluoro | methoxy | 83 | >300 |
| 17 | cyclohexyl | 2-fluoro | methoxy | 79 | 172–173 |
| 18 | cyclohexyl | 2,6-difluoro | methoxy | 73 | 207–208 |
| 19 | phenyl | 2,6-difluoro | nitro | 93 | 280–282 |
| 20 | 2-methoxyphenyl | 2-fluoro | methoxy | 84 | 195–198 |
| 21 | 2-methoxyphenyl | 2,6-difluoro | methoxy | 86 | 205–208 |
| 22 | 3-methoxyphenyl | 2-fluoro | methoxy | 89 | 241–242 |
| 23 | 3-methoxyphenyl | 2,6-difluoro | methoxy | 85 | 253–255 |
| 24 | 2-chlorophenyl | 2-fluoro | methoxy | 91 | 220–221 |
| 25 | 2-chloro- | 2,6- | methoxy | 83 | 178–182 |

TABLE 6-continued

| Ref. Ex. 24 Cpd. No. | R³³ | R³⁵ | R³⁴ | Yield (%) | m.p. (°C.) |
|---|---|---|---|---|---|
| 26 | phenyl 3-chloro-phenyl | difluoro 2-fluoro | methoxy | 90 | 247–248 |
| 27 | 3-chloro-phenyl | 2,6-difluoro | methoxy | 93 | 278–279 |
| 28 | 4-chloro-phenyl | 2-fluoro | methoxy | 79 | 269–270 |
| 29 | 4-chloro-phenyl | 2,6-difluoro | methoxy | 91 | >300 |

Reference Example 25

5-Bromomethyl-2,4(1H,3H)-dioxo-1-(2-fluorobenzyl)-6-(4-nitrophenyl)thieno[2,3-d]pyrimidin-3-acetic acid ethyl ester A mixture of the compound produced in Reference Example 23(0.300 g, 0.603 mmol), N-bromosuccinimide (0.107 g, 0.603 mmol), α,α'-azobisisobutyronitrile (10 mg, 0.60 mmol) and carbon tetrachloride (15 ml) was refluxed for 2 hours. Upon cooling resulting insolubles were filtered off from the reaction mixture. The filtrate was diluted with chloroform. The organic layer was washed with an aqueous sodium chloride solution and dried (MgSO₄), then the solvent was distilled off under reduced pressure. The residue was recrystallized from ethyl acetate to give colorless needles (0.284 g, 82%), m.p.165°–167° C.

| Elemental Analysis for $C_{24}H_{19}N_3O_6SBrF$: | | | |
|---|---|---|---|
| | C(%) | H(%) | N(%) |
| Calcd. | 50.01 | 3.32 | 7.29 |
| Found | 49.87 | 3.27 | 7.23 |

¹H-NMR (200 MHz, CDCl₃) δ: 1.31(3H,t,J=7.1 Hz), 4.26(2H,q,J=7.1 Hz), 4.78(2H,s), 4.86(2H,s), 5.30(2H,s), 7.07–7.37(4H,m), 7.75(2H,d,J=8.8 Hz), 8.33(2H,d,J=8.8 Hz). IR (KBr): 1713, 1673, 1524, 1477 cm⁻¹.

Reference Example 26

Starting from the compounds produced in Reference Example 24, compounds set forth in Table 7 were produced in accordance with the method described in Reference Example 25.

TABLE 7

| Ref. Ex. 26 Cpd. No. | R³³ | R³⁵ | R³⁴ | Yield (%) | m.p. (°C.) |
|---|---|---|---|---|---|
| 1 | ethyl acetate | 2-fluoro | methoxy | 70 | 152–153 |
| 2 | methyl | 2-methoxy | methoxy | 63 | 173–176 |
| 3 | methyl | 2-fluoro | methoxy | 82 | 175–177 |
| 4 | phenyl | 2-methoxy | methoxy | 93 | 240–241 |
| 5 | phenyl | 2-fluoro | methoxy | 86 | 230–233 |
| 6 | phenyl | 2-fluoro | nitro | 86 | 224–225 |
| 7 | phenyl | 3-fluoro | methoxy | 84 | 215–216 |
| 8 | phenyl | 4-fluoro | methoxy | 84 | 232–233 |
| 9 | phenyl | 2,4-difluoro | methoxy | 84 | 230–231 |
| 10 | phenyl | 2,6-difluoro | methoxy | 87 | 250–252 |
| 11 | phenyl | 2-chloro, 6-fluoro | methoxy | 86 | 255–257 |
| 12 | phenyl | 2-methyl-thio | methoxy | 90 | 212–214 |
| 13 | benzyl | 2-fluoro | methoxy | 83 | 132–134 |
| 14 | benzyl | 2,6-difluoro | methoxy | 89 | 154–155 |
| 15 | 4-methoxyphenyl | 2-fluoro | methoxy | 88 | 226–228 |
| 16 | 4-methoxyphenyl | 2,6-difluoro | methoxy | 80 | 249–251 |
| 17 | cyclohexyl | 2-fluoro | methoxy | 86 | 149–151 |
| 18 | cyclohexyl | 2,6-difluoro | methoxy | 77 | 192–194 |
| 19 | phenyl | 2,6-difluoro | nitro | 94 | 228–229 |
| 20 | 2-methoxyphenyl | 2-fluoro | methoxy | 77 | 180–181 |
| 21 | 2-methoxyphenyl | 2,6-difluoro | methoxy | 79 | 212–214 |
| 22 | 3-methoxyphenyl | 2-fluoro | methoxy | 82 | 234–235 |
| 23 | 3-methoxyphenyl | 2,6-difluoro | methoxy | 88 | 255–256 |
| 24 | 2-chlorophenyl | 2-fluoro | methoxy | 85 | 175–178 |
| 25 | 2-chlorophenyl | 2,6-difluoro | methoxy | 88 | 191–193 |
| 26 | 3-chlorophenyl | 2-fluoro | methoxy | 81 | 243–246 |
| 27 | 3-chlorophenyl | 2,6-difluoro | methoxy | 92 | 270–273 |
| 28 | 4-chlorophenyl | 2-fluoro | methoxy | 84 | 271–274 |
| 29 | 4-chlorophenyl | 2,6-difluoro | methoxy | 78 | 265–268 |

Reference Example 27

5-Benzylmethylaminomethyl-2,4(1H,3H)-dioxo-1-(2-fluorobenzyl)-6-nitrophenyl)thieno[2,3-d]pyrimidin-3-acetic acid ethyl ester hydrochloride To a solution of the compound produced in Reference Example 25 (0.270 g, 0.47 mmol) in dimethylformamide (10 ml) were added, under ice-cooling, ethyl diisopropylamine (0.12 ml, 0.710 mmol) and benzylmethyl amine (0.07 ml, 0.56 mmol). The mixture was stirred for 20 hours at room temperature. The reaction mixture was concentrated, and the concentrate was partitioned between ethyl acetate and a saturated aqueous solution of sodium hydrogencarbonate. The aqueous layer was extracted with ethyl acetate. Organic layers were combined and dried (MgSO$_4$), then the solvent was distilled off under reduced pressure. The residue was chromatographed on silica gel to give a colorless oil (0.297 g, 100%). To a solution of this oil in ethyl acetate was added, under ice-cooling, 1N ethereal hydrochloric acid. The mixture was stirred for 10 minutes at the same temperature. The reaction mixture was concentrated under reduced pressure, and the concentrate was crystallized from ethyl acetate ether to give the corresponding hydrochloride (0.084 g) as white crystals. m.p.[hydrochloride] 120°–128° C.

Elemental Analysis for C$_{37}$H$_{29}$N$_4$O$_6$SF.HCl.H$_2$O:

|  | C(%) | H(%) | N(%) |
|---|---|---|---|
| Calcd. | 57.27 | 4.81 | 8.35 |
| Found | 57.23 | 4.55 | 8.42 |

$^1$H-NMR (200 MHz, CDCl$_3$) [free amine] δ: 1.31(3H,t,J=7.1 Hz), 2.16(3H,s), 3.61(2H,s), 3.97(2H,s), 4.27(2H,q,J=7.1 Hz), 4.87(2H,s), 5.31(2H,s), 7.10–7.35(9H,m), 7.97(2H,d,J=8.8 Hz), 8.23(2H,d,J=8.8 Hz). IR (KBr) [hydrochloride]: 1711, 1665, 1522, 1493 cm$^{-1}$.

Working Example 1
4,7-Dihydro-7-(2-methoxybenzyl)-2-(4-methoxyphenyl)-3-methyl-4-oxothieno[2,3-b]pyridine-5-carboxylic acid ethyl ester To a suspension of sodium hydride (60% oil; 123 mg, 3.08 mmol) in dimethylformamide (3 ml) was added dropwise, in an atmosphere of nitrogen under ice-cooling, a solution of the compound produced in Reference Example 8 (1.0 g, 2.91 mmol) in dimethylformamide (20 ml). The mixture was stirred for 30 minutes under ice-cooling, to which was added dropwise a solution of 2-methoxybenzyl chloride (0.92 g, 5.87 mmol) in dimethylformamide (3 ml). The reaction mixture was stirred for 23 hours at room temperature, then for 2 hours at 70° C. The reaction mixture was then concentrated, and the concentrate was partitioned between ethyl acetate and an aqueous ammonium chloride solution. The aqueous layer was extracted with ethyl acetate. The extract was washed with an aqueous sodium chloride solution and dried (MgSO$_4$), then the solvent was distilled off under reduced pressure. The residue was chromatographed on silica gel to give a pale yellow amorphous (0.95 g, 70%). As the sample for elemental analysis, the amorphous was recrystallized from dichloromethane-ether to afford yellow prisms, m.p.165°–167° C.

Elemental Analysis for C$_{26}$H$_{25}$NO$_5$S.0.5H$_2$O:

|  | C(%) | H(%) | N(%) |
|---|---|---|---|
| Calcd. | 66.08 | 5.55 | 2.96 |
| Found | 66.33 | 5.44 | 2.74 |

$^1$H-NMR (200 MHz, CDCl$_3$) δ: 1.41(3H,t,J=7.1 Hz), 2.65(3H,s), 3.85(3H,s), 3.86(3H,s), 4.39(2H,q,J=7.1 Hz), i 5.16(2H,s), 6.92–7.00(4H,m), 7.21–7.41(4H,m), 8.41(1H,s). IR(KBr): 2980, 1727, 1684, 1609, 1590, 1497, 1464 cm$^{-1}$.

Working Example 2

Employing the compound produced in Reference Example 8 as the starting material, in accordance with substantially the same reaction as described in Working Example 1, the compounds shown in Table 8 were produced.

TABLE 8

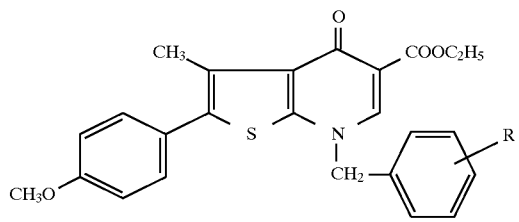

| W. Ex. 2 Cpd. No. | R | Yield (%) | m.p. (°C.) |
|---|---|---|---|
| 1 | H | 49 | 170–172 |
| 2 | 3-methoxy | 71 | 153–155 |
| 3 | 4-methoxy | 72 | 132–134 |
| 4 | 2-methyl | 63 | 199–201 |
| 5 | 2-acetoxy | 52 | 154–156 |
| 6 | 2-methylthio | 49 | 152–154 |
| 7 | 4-nitro | 97 | 98–99 |
| 8 | 4-(2-cyanophenyl) | 62 | 134–136 |
| 9 | 4-(2-t-butoxy-carbonyl)phenyl | 76 | 120–122 |

Working Example 3

Employing the compounds produced in Reference Examples 9 and 10 as the starting materials, the compounds shown in Table 9 were produced by substantially the same procedure as described in Working Example 1.

TABLE 9

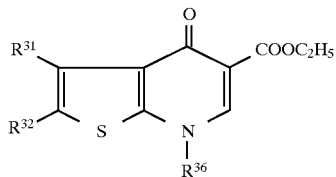

| W. Ex. 3 Cpd. No. | R$^{31}$ | R$^{32}$ | R$^{36}$ | Yield (%) | m.p. (°C.) |
|---|---|---|---|---|---|
| 1 | methyl | 4-nitrophenyl | 2-methoxybenzyl | 69 | 194–195 |
| 2 | methyl | phenyl | 2-methoxybenzyl | 91 | amorphous |
| 3 | phenyl | methyl | 2-methoxybenzyl | 73 | 184–186 |
| 4 | methyl | benzyl | 2-methoxyphenyl | 47 | 65–70 |
| 5 | methyl | phenylacetyl | 2-methoxyphenyl | 64 | 167–170 |
| 6 | methyl | 2-methoxyphenyl | 2-methoxyphenyl | 57 | 194–196 |
| 7 | methyl | bromine | 2-methoxyphenyl | 90 | 161–163 |
| 8 | methyl | 4-nitrophenyl | 2-fluorobenzyl | 90 | 184–186 |
| 9 | methyl | 4-methoxyphenyl | 2-fluorobenzyl | 81 | 117–120 |
| 10 | methyl | 4-methoxyphenyl | 2,6-difluorobenzyl | 80 | amorphous |
| 11 | methyl | 4-nitrophenyl | 2,6-difluorobenzyl | 81 | 215–217 |
| 12 | methyl | 4-nitrophenyl | 2-chloro-6-fluorobenzyl | 80 | 211–213 |
| 13 | methyl | phenyl | 2,6-difluorobenzyl | 90 | 184–186 |

TABLE 9-continued

[Structure: thieno[2,3-b]pyridine with R31, R32, S, N-R36, O, COOC2H5 substituents]

| W. Ex. 3 Cpd. No. | R³¹ | R³² | R³⁶ | Yield (%) | m.p. (°C.) |
|---|---|---|---|---|---|
| 14 | methyl | phenyl | 2-chloro-6-fluorobenzyl | 86 | 171–173 |
| 15 | methyl | 4-methoxyphenyl | 1-naphthyl | 74 | 193–195 |
| 16 | methyl | 4-methoxyphenyl | 2-methoxyphenethyl | 50 | 134–136 |
| 17 | methyl | 4-methoxyphenyl | phenethyl | 54 | 182–184 |
| 18 | methyl | 4-methoxyphenyl | 3-phenylpropyl | 62 | 147–149 |
| 19 | methyl | 4-methoxyphenyl | cinnamyl | 64 | 170–172 |
| 20 | methyl | 4-methoxyphenyl | 3-picolyl | 28 | 142–144 |
| 21 | methyl | bromine | 2-fluorobenzyl | 78 | 211–213 |
| 22 | methyl | bromine | 2,6-difluorobenzyl | 73 | 175–176 |

Working Example 4

4,7-Dihydro-5-hydroxymethyl-7-(2-methoxybenzyl)-2-(4-methoxyphenyl)-3-methyl-4-oxothieno[2,3-b]pyridine To a solution of the compound produced in Reference Example 11 (0.12 g, 0.40 mmol) in dimethylformamide (10 ml) were added, at room temperature, potassium carbonate (0.083 g, 0.60 mol), 2-methoxybenzyl chloride (0.094 g, 0.60 mol) and potassium iodide (0.033 g, 0.20 mmol). The mixture was stirred for 90 minutes at room temperature, and then for 2 hours at 50° C. The reaction mixture was concentrated, and the concentrate was partitioned between dichloromethane and water. The aqueous layer was extracted with dichloromethane. The extract was washed with an aqueous sodium chloride solution, which was then dried (MgSO₄), then the solvent was distilled off under reduced pressure. The residue was chromatographed on silica gel to give a pale yellow amorphous, which was recrystallized from ethyl acetate to afford colorless crystals, m.p.153°–156° C.

| Elemental Analysis for $C_{24}H_{23}NO_4S$: | | | |
|---|---|---|---|
| | C(%) | H(%) | N(%) |
| Calcd. | 68.39 | 5.50 | 3.32 |
| Found | 68.11 | 5.58 | 3.24 |

¹H-NMR (200 MHz, CDCl₃) δ: 2.67(3H,s), 3.85(3H,s), 3.86(3H,s), 4.59(2H,s), 5.12(2H,s), 6.90–7.00(4H,m), 7.15 (1H,d), 7.3–7.4(3H,m), 7.45(1H,s). IR(KBr): 3400, 2936, 2838, 1618, 1547, 1504, 1249 cm¹.

Working Example 5

5-Acetoxymethyl-4,7-dihydro-7-(2-methoxybenzyl)-2-(4-methoxyphenyl)-3-methyl-4-oxothieno[2,3-b]pyridine To a solution of the compound produced in Working Example 4 in pyridine (0.400 g, 0.96 mmol) was added, at room temperature, anhydrous acetic acid (1.78 g, 19.0 mmol). The mixture was stirred for one hour at room temperature. The reaction mixture was concentrated. The concentrate was partitioned between ethyl acetate and dilute hydrochloric acid. The aqueous layer was extracted with ethyl acetate. The extract was chromatographed on silica gel to give a colorless amorphous, which was recrystallized from ethyl ether to give colorless crystals (0.46 g, 100%), m.p.158°–159° C.

| Elemental Analysis for $C_{26}H_{25}NO_5S$: | | | |
|---|---|---|---|
| | C(%) | H(%) | N(%) |
| Calcd. | 67.37 | 5.44 | 3.02 |
| Found | 67.09 | 5.09 | 3.06 |

¹H-NMR (200 MHz, CDCl₃) δ: 2.07(3H,s), 2.67(3H,s), 3.84(3H,s), 3.86(3H,s), 5.11(2H,s), 5.12(2H,s), 6.90–7.00 (4H,m), 7.18(1H,d,J=7.7 Hz), 7.3–7.4(3H,m), 7.69(1H,s). IR(KBr): 1752, 1626, 1578, 1508, 1506, 1255 cm⁻¹.

Working Example 6

3-Bromomethyl-4,7-dihydro-7-(2-methoxybenzyl)-2-(4-methoxyphenyl)-4-oxothieno[2,3-b]pyridine-5-carboxylic acid ethyl ester A mixture of the compound produced in Working Example 1(0.35 g, 0.755 mmol), N-bromosuccinimide (0.135 g, 0.758 mmol), α,α'-azobis isobutyronitrile (13 mg, 0.079 mmol) and carbon tetrachloride (5 ml) was refluxed for 2 hours. Upon cooling, resulting insolubles were filtered off from the reaction mixture, and the filtrate was diluted with chloroform. The organic layer was washed with an aqueous sodium chloride solution and, then, dried (MgSO₄). The solvent was distilled off under reduced pressure, and the residue was recrystallized from ethyl acetate to afford colorless needles (0.272 g, 66%), m.p.200°–201° C.

| Elemental Analysis for $C_{26}H_{24}NO_5SBr$: | | | |
|---|---|---|---|
| | C(%) | H(%) | N(%) |
| Calcd. | 57.57 | 4.46 | 2.58 |
| Found | 57.75 | 4.31 | 2.31 |

¹H-NMR (200 MHz, CDCl₃) δ: 1.40(3H,t,J=7.1 Hz), 3.86(6H,s), 4.40(2H,q,J=7.1 Hz), 5.05(2H,s), 5.16(2H,s), 6.92–7.04(4H,m), 7.23–7.28(1H,m), 7.34–7.43(1H,m), 7.57 (2H,d,J=8.9 Hz), 8.46(1H,s). IR(KBr): 2980, 1725, 1607, 1588, 1497 cm⁻¹.

Working Example 7

Employing the compounds produced in Working Examples 3, 4, 19, 65, 66 and 73 as starting materials, in accordance with substantially the same manner as described in Working Example 6, the compounds shown by Table 10 were produced.

TABLE 10

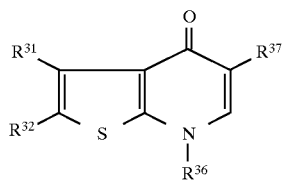

| W. Ex. 7 Cpd. No. | R³¹ | R³² | R³⁷ | R³⁶ | Yield (%) | m.p. (°C.) |
|---|---|---|---|---|---|---|
| 1 | bromo-methyl | 4-nitro-phenyl | ethoxy-carbonyl | 2-methoxy-benzyl | 95 | 173–175 |
| 2 | bromo-methyl | 4-methoxy-phenyl | acetoxy-methyl | 2-methoxy-benzyl | 37 | 131–133 |
| 3 | bromo-methyl | phenyl | ethoxy-carbonyl | 2-methoxy-benzyl | 71 | 194–196 |
| 4 | phenyl | bromo-methyl | ethoxy-carbonyl | 2-methoxy-benzyl | 40 | amorphous |
| 5 | bromo-methyl | benzoyl | ethoxy-carbonyl | 2-methoxy-benzyl | 36 | amorphous |
| 6 | bromo-methyl | 2-methoxy-phenyl | ethoxy-carbonyl | 2-methoxy-benzyl | 55 | amorphous |
| 7 | bromo-methyl | bromide | ethoxy-carbonyl | 2-methoxy-benzyl | 59 | 174–175 |
| 8 | bromo-methyl | 3-methoxy-phenyl | ethoxy-carbonyl | 2-methoxy-benzyl | 91 | 83–86 |
| 9 | bromo-methyl | 4-nitro-phenyl | ethoxy-carbonyl | 2-fluoro-benzyl | 69 | 202–204 |
| 10 | bromo-methyl | 4-methoxy-phenyl | ethoxy-carbonyl | 2-fluoro-benzyl | 100 | amorphous |
| 11 | bromo-methyl | 4-nitro-phenyl | ethoxy-carbonyl | 2,6-difluoro-benzyl | 81 | 200–202 |
| 12 | bromo-methyl | 4-nitro-phenyl | ethoxy-carbonyl | 2-chloro-6-fluoro-benzyl | 62 | 175–177 |
| 13 | bromo-methyl | 4-methoxy-phenyl | 1-acetoxy ethyl | 2-fluoro-benzyl | 43 | amorphous |
| 14 | bromo-methyl | 4-nitro-phenyl | benzoyl | 2,6-difluoro-benzyl | 80 | 236–238 |
| 15 | bromo-methyl | 4-nitro-phenyl | isobutyryl | 2,6-difluoro-benzyl | 84 | 123–124 |
| 16 | bromo-methyl | 4-methoxy-phenyl | isobutyryl | 2,6-difluoro-benzyl | 81 | 226–228 |
| 17 | bromo-methyl | 4-methoxy-phenyl | acetyl | 2-fluoro-benzyl | 75 | 186–187 |
| 18 | bromo-methyl | 4-methoxy phenyl | propionyl | 2-fluoro-benzyl | 45 | 165–166 |
| 19 | bromo-methyl | 4-methoxy phenyl | butyryl | 2-fluoro-benzyl | 65 | 165–166 |
| 20 | bromo-methyl | 4-methoxy-phenyl | hexanoyl | 2-fluoro-benzyl | 55 | 168–169 |
| 21 | bromo-methyl | 4-methoxy-phenyl | valeryl | 2-fluoro-benzyl | 63 | 173–174 |
| 22 | bromo-methyl | 4-methoxy-phenyl | heptonoyl | 2-fluoro-benzyl | 54 | 146–147 |
| 23 | bromo-methyl | 4-methoxy-phenyl | isovaleryl | 2-fluoro-benzyl | 74 | 187–189 |
| 24 | bromo- | 4- | benzoyl | 2-fluoro- | 75 | 145–147 |

TABLE 10-continued

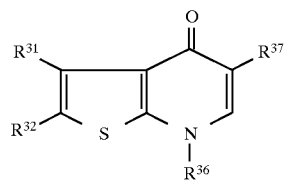

| W. Ex. 7 Cpd. No. | R³¹ | R³² | R³⁷ | R³⁶ | Yield (%) | m.p. (°C.) |
|---|---|---|---|---|---|---|
|  | methyl | methoxy-phenyl |  | benzyl |  |  |
| 25 | bromo-methyl | 4-ethoxy-carbonyl-phenyl | ethoxy-carbonyl | 2-methoxy-benzyl | 98 | 196–198 |
| 26 | bromo-methyl | 4-methoxy-phenyl | ethoxy-carbonyl | 2-fluoro-benzyl | 77 | 115–120 |
| 27 | bromo-methyl | 4-diethyl-amino-carbonyl-phenyl | ethoxy-carbonyl | 2-fluoro-benzyl | 40 | amorphous |
| 28 | bromo-methyl | 4-ethoxy-carbonyl-phenyl | benzoyl | 2,6-difluoro-benzyl | 88 | 190–192 |
| 29 | bromo-methyl | 4-butoxy-phenyl | ethoxy-carbonyl | 2-fluoro-benzyl | 40 | 138–140 |
| 30 | bromo-methyl | 4-methoxy phenyl | cyano | 2-fluoro-benzyl | 100 | 216–218 |

Working Example 8
3-Benzylaminomethyl-4,7-dihydro-7-(2-methoxybenzyl)-3-(4-methoxyphenyl)-4-oxothieno[2,3-b]pyridine-5-carboxylic acid ethyl ester hydrochloride To a solution of the compound produced in Working Example 6(0.245 g, 0.452 mmol) in dimethylformamide (5 ml) were added, under ice-cooling, triethylamine (0.10 ml, 0.717 mmol) and benzylamine (80 μl, 0.732 mmol). The mixture was stirred for 90 minutes at room temperature. The reaction mixture was concentrated, and the concentrate was partitioned between ethyl acetate and a saturated aqueous solution of sodium hydrogen carbonate. The aqueous layer was extracted with ethyl acetate. The organic layer was dried (MgSO$_4$),then the solvent was distilled off under reduced pressure. The residue was chromatographed on silica gel to give a colorless oil (0.135 g, 53%). To a solution of the oily in ethanol (4 ml) was added, under ice-cooling, IN ethanolic hydrochloric acid (0.2 ml). The mixture was stirred for 10 minutes with ice-cooling. The reaction mixture was concentrated under reduced pressure, which was crystallized from ethyl acetate and ether to give the corresponding hydrochloride (0.113 g) as white crystals, m.p.118°–119° C.

| Elemental Analysis for $C_{33}H_{32}N_2O_5S \cdot HCl \cdot 0.9H_2O$: | | | |
|---|---|---|---|
|  | C(%) | H(%) | N(%) |
| Calcd. | 63.79 | 5.64 | 4.51 |
| Found | 64.03 | 5.44 | 4.51 |

$^1$H-NMR (200 MHz, CDCl$_3$) [Free amine] δ: 1.40(3H,t, J=7.1 Hz), 2.05(1H,br), 3.81(3H,s), 3.86(3H,s), 3.87(2H,s), 3.94(2H,s), 4.40(2H,q,J=7.1 Hz), 5.18(2H,s), 6.80(2H,d,J= 8.8 Hz), 6.91–6.99(2H,m), 7.20–7.42(9H,m), 8.45(1H,s). IR(KBr) [hydrochloride]: 3422, 2938, 1719, 1605, 1560, 1545, 1502, 1460 cm$^{-1}$.

Working Example 9

Employing, as the starting material, the compound produced in Working Example 6, the compounds shown in Table 11 were produced by substantially the same procedures as described in Working Example 8.

TABLE 11

[Structure: thieno-pyridinone core with R³¹ and phenyl(4-OCH₃) on thiophene, COOC₂H₅ on pyridinone, N-CH₂-(2-methoxyphenyl) substituent]

| W. Ex. 9 Cpd. No. | R³¹ | Yield (%) | m.p. (°C.) |
|---|---|---|---|
| 1 | anilinomethyl | 44 | 173–174 |
| 2 | phenethylaminomethyl | 34 | 148–15 (oxalate) |
| 3 | phenylpropylaminomethyl | 36 | 116–118 (hydrochloride) |
| 4 | N'-methylpiperazinylmethyl | 63 | 138–139 |
| 5 | N'-phenylpiperazinylmethyl | 61 | 189–190 |
| 6 | 4-phenylpiperidinomethyl | 52 | 165–167 (oxalate) |
| 7 | N'-benzylpiperazinylmethyl | 86 | 109–110 (oxalate) |
| 8 | phthalimidomethyl | 46 | 221–223 |
| 9 | 1,2,3,4-tetrahydro-isoquinolylmethyl | 49 | 156–158 (hydrochloride) |
| 10 | benzhydrylaminomethyl | 52 | 133–135 (hydrochloride) |
| 11 | N-phenyl-N-benzylaminomethyl | 20 | 93–95 (hydrochloride) |
| 12 | methylaminomethyl | 100 | 118–120 (hydrobromide) |
| 13 | ethylaminomethyl | 100 | 114–116 (hydrobromide) |
| 14 | N-benzyl-N-methylaminomethyl | 69 | 96–98 (oxalate) |
| 15 | N-benzyl-N-methylaminomethyl | 77 | 147–152 (hydrochloride) |
| 16 | 2-methoxybenzylaminomethyl | 40 | 108–110 (hydrochloride) |
| 17 | 3-methylbenzylaminomethyl | 28 | 110–112 (hydrochloride) |
| 18 | 3,4-dimethoxybenzylaminomethyl | 10 | 129–131 (hydrochloride) |
| 19 | 2-phenylimidazo-1-ylmethyl | 49 | 130–132 |
| 20 | aminomethyl | 89 | 104–106 (hydrobromide) |
| 21 | N-benzyl-N-dimethylammonium methyl | 40 | 135–137 (bromide) |
| 22 | N-methyl-N-(2,3,4-trimethoxybenzyl)aminomethyl | 31 | 113–115 (hydrochloride) |
| 23 | N-methyl-N-(N-methylindol-3-yl)ethylaminomethyl | 43 | 151–153 (hydrochloride) |
| 24 | N-methyl-N-phenylpropylaminomethyl | 64 | 103–105 (hydrochloride) |
| 25 | N-methyl-N-(2-thiomethylbenzyl)aminomethyl | 77 | 115–117 (hydrochloride) |
| 26 | N-methyl-N-(3,5-trifluoro-methylbenzyl)aminomethyl | 53 | 130–132 (hydrochloride) |
| 27 | N-methyl-N-(2,6-dichlorobenzyl)aminomethyl | 75 | 124–126 (hydrochloride) |
| 28 | N-methyl-N-(2-nitrobenzyl)aminomethyl | 76 | 139–141 (hydrochloride) |
| 29 | t-butylaminomethyl | 80 | 126–128 (hydrobromide) |
| 30 | dimethylaminomethyl | 98 | 117–119 (hydrobromide) |
| 31 | N-methyl-N-(2-chlorobenzyl)-aminomethyl | 64 | 143–145 (hydrochloride) |
| 32 | N-methyl-N-(3-chlorobenzyl)-aminomethyl | 75 | 203–205 (hydrochloride) |
| 33 | N-methyl-N-(4-chlorobenzyl)-aminomethyl | 67 | 197–199 (hydrochloride) |
| 34 | N-methyl-N-(2-fluorobenzyl)-aminomethyl | 38 | 120–122 (hydrochloride) |
| 35 | dibenzylaminomethyl | 55 | 155–157 (hydrochloride) |
| 36 | N-hydroxyethyl-N-benzyl-aminomethyl | 60 | 112–144 (hydrochloride) |
| 37 | N-ethoxycarbonylethyl-N-benzylaminomethyl | 50 | 78–80 (hydrochloride) |
| 38 | N-benzyl-N-acetamidomethyl | 17 | 78–82 (hydrochloride) |
| 39 | N-propyl-N-benzylaminomethyl | 64 | 103–107 (hydrochloride) |
| 40 | N-benzyl-N-phenethyl aminomethyl | 67 | 105–111 (hydrochloride) |
| 41 | 2-indanylaminomethyl | 56 | 128–132 (hydrochloride) |
| 42 | N-methyl-N-(2-indanyl)aminomethyl | 24 | 121–125 (hydrochloride) |
| 43 | N-methyl-N-(3-nitrobenzyl)aminomethyl | 80 | 209–211 (hydrochloride) |
| 44 | N-methyl-N-(4-nitrobenzyl)aminomethyl | 80 | 199–201 (hydrochloride) |
| 45 | N-methyl-N-(2-phenyl-benzyl)aminomethyl | 70 | 112–114 (hydrochloride) |

Working Example 10

Employing the compounds produced in Working Example 7, the compounds shown in Table 12 were produced by substantially the same procedure described in Working Example 8.

TABLE 12

| W. Ex. 10 Cpd. No. | R³¹ | R³² | R³⁵ | R³⁷ | Yield (%) | m.p. (°C.) |
|---|---|---|---|---|---|---|
| 1 | N-benzyl-N-methylamino-methyl | 4-nitro-phenyl | 2-methoxy | ethoxy-carbonyl | 73 | 124–126 (hydro-chloride) |
| 2 | N-benzyl-N-methylamino-methyl | 4-methoxy-phenyl | 2-methoxy | acetoxy-methyl | 30 | 108–117 (hydro-chloride) |
| 3 | N-benzyl-aminomethyl | phenyl | 2-methoxy | ethoxy-carbonyl | 25 | 167–169 (hydro-chloride) |
| 4 | N-benzyl-N-methylamino-methyl | phenyl | 2-methoxy | ethoxy-carbonyl | 94 | 117–120 (hydro-chloride) |
| 5 | phenyl | N-benzyl-aminomethyl | 2-methoxy | ethoxy-carbonyl | 40 | 195–197 (hydro-chloride) |
| 6 | N-benzyl-N-methylamino-methyl | benzoyl | 2-methoxy | ethoxy-carbonyl | 70 | 90–95 (hydro-chloride) |
| 7 | N-benzyl-aminomethyl | 2-methoxy-phenyl | 2-methoxy | ethoxy-carbonyl | 18 | 114–118 (hydro-chloride) |
| 8 | N-benzyl-N-methylamino-methyl | 2-methoxy-phenyl | 2-methoxy | ethoxy-carbonyl | 57 | 119–122 |
| 9 | N-benzylamino-methyl | bromine | 2-methoxy | ethoxy-carbonyl | 60 | 207–211 (oxalate) |
| 10 | N-benzyl-N-methylamino-methyl | bromine | 2-methoxy | ethoxy-carbonyl | 78 | 112–116 (oxalate) |
| 11 | N-benzyl-N-methylamino-methyl | 3-methoxy-phenyl | 2-methoxy | ethoxy-carbonyl | 71 | 115–120 (hydro-chloride) |
| 12 | N-benzyl-N-methylamino-methyl | 4-methoxy-carbonyl-phenyl | 2-methoxy | ethoxy-carbonyl | 94 | 122–125 (hydro-chloride) |
| 13 | N-benzyl-N-methylamino-methyl | 4-methoxy-phenyl | 2-fluoro | cyano | 92 | 203–206 (hydro-chloride) |

Working Example 11

4,7-Dihydro-7-(2-methoxybenzyl)-2-(4-methoxyphenyl)-3-methyl-4-oxothieno[2,3-b]pyridine-N-benzylpiperazinyl-5-carboxamide To 1-benzylpiperazine (0.77 g, 4.37 mmol) was added dropwise, under ice-cooling, a toluene solution of diisobutyl aluminum hydride (1.5N, 2.9 ml, 4.37 mmol). The mixture was warmed to room temperature and stirred for 30 minutes. To this solution was, at room temperature, added a solution of the compound produced in working Example 1 (0.50 g, 1.08 mmol) in toluene (5 ml). After stirring for 15 hours at room temperature, to the reaction mixture was added methylene chloride (30 ml). The mixture was washed with water, then, dried over sodium sulfate. The solvent was distilled off under reduced pressure to leave a solid compound (1.03 g), which was recrystallized from methylene chloride-n-hexane to give the above-titled compound (0.48 g, 78%), m.p.233°–235° C.

| Elemental Analysis for $C_{35}H_{35}N_3O_4S \cdot 1/2H_2O$: | | | | |
|---|---|---|---|---|
| | C(%) | H(%) | N(%) | S(%) |
| Calcd. | 69.75 | 6.02 | 6.97 | 5.32 |
| Found | 69.88 | 6.06 | 6.98 | 5.39 |

$^1$H-NMR (200 MHz, CDCl$_3$) δ: 2.45–2.55(4H,m), 2.63 (3H,s), 3.43–3.49(2H,m), 3.55(2H,s), 3.73–3.82(2H,m), 3.84(6H,s), 5.11(2H,s), 6.89–6.98(4H,m), 7.21–7.40(9H,m), 7.79(1H,s).

Working Example 12

Employing, as the starting material, the compound produced in Working Example 1, in accordance with substantially the same procedure as described in Working Example 11, the compounds set forth in Table 13 were produced.

TABLE 13

[Structure: thieno[2,3-b]pyridine core with CH₃ at 3-position, R³² at 2-position on thiophene S, R³⁶ on N, and CONR³⁸R³⁹ at 5-position with C=O at 4-position]

| W. Ex. 12 Cpd. No. | R³² | R³⁶ | R³⁸ | R³⁹ | Yield (%) | m.p. (°C.) |
|---|---|---|---|---|---|---|
| 1 | 4-methoxyphenyl | 2-methoxybenzyl | 3-pyridyl | hydrogen | 54 | 214–216 |
| 2 | 4-methoxyphenyl | 2-methoxybenzyl | dimethylaminopropyl | hydrogen | 59 | 160–164 |
| 3 | 4-methoxyphenyl | 2-methoxybenzyl | 3-pyridylmethyl | hydrogen | 60 | 168–170 |
| 4 | 4-nitrophenyl | 2,6-difluorobenzyl | methyl | methoxy | 80 | 223–224 |
| 5 | phenyl | 2,6-difluorobenzyl | methyl | methoxy | 85 | amorphous |

Working Example 13

4,7-Dihydro-7-(2-methoxybenzyl)-2-(4-methoxyphenyl)-3-[N-methyl-N-(2-methoxybenzyl)aminomethyl]-4-oxothieno[2,3-b]pyridine-5-carboxylic acid ethyl ester·hydrochloride To a solution of the compound 12 produced in Working Example 9 (0.30 g, 0.52 mmol) in ethyl alcohol (5 ml) were added, at room temperature, triethylamine (0.21 g, 2.1 mmol) and 2-methoxybenzyl chloride (0.16 g, 1.0 mmol). The mixture was stirred for 60 hours at room temperature. The reaction mixture was concentrated, and the concentrate was partitioned between ethyl acetate and a saturated aqueous solution of sodium hydrogencarbonate. The aqueous layer was extracted with ethyl acetate. The combined organic layer was dried ($Na_2SO_4$), and then, the solvent was distilled off under reduced pressure. The residue was chromatographed on silica gel to give a yellow oil (0.23 g, 72%). To a solution of this oil (0.07 g, 0.10 mmol) in ethyl acetate (5 ml) was added, under ice-cooling, a 1N ether solution of hydrogen chloride (0.2 ml, 0.20 mmol) during 5 minutes. The reaction mixture was concentrated under reduced pressure. The resulting residue was recrystallized from ethyl acetate-ether to give the corresponding hydrochloride (0.07 g, 100%) as white crystals, m.p.107°–109° C.

Elemental Analysis for $C_{35}H_{36}N_2O_6S \cdot HCl \cdot H_2O$:

|  | C(%) | H(%) | N(%) |
|---|---|---|---|
| Calcd. | 63.01 | 5.89 | 4.20 |
| Found | 63.57 | 6.05 | 3.88 |

¹H-NMR (200 MHz, $CDCl_3$) [free amine] δ: 1.39(3H,t, J=7.2 Hz), 2.38(3H,s), 3.71(3H,s), 3.85(3H,s), 3.87(3H,s), 3.88(2H,s), 4.30(2H,s), 4.39(2H,q,J=7.2 Hz), 5.21(2H,s), 6.77–7.70(12H,m), 8.44(1H,s). IR(KBr) [hydrochloride]: 3422, 2944, 1721, 1605, 1499, 1464, 1383, 1294, 1253 cm⁻¹. FAB-Mass m/z 613(MH)⁺

Working Example 14

Employing, as the starting material, the compound 12 produced in Working Example 9, in accordance with substantially the same procedure as described in Working Example 13, the compounds set forth in Table 14 were produced.

TABLE 14

[Structure: thieno[2,3-b]pyridine core with R⁴⁰-N(R⁴¹)-CH₂ group, 4-methoxyphenyl substituent, 2-methoxybenzyl on N, and COOC₂H₅ group]

| W. Ex. 14 Cpd. No. | R⁴⁰ | R⁴¹ | Yield (%) | m.p. (°C.) |
|---|---|---|---|---|
| 1 | 2-methylbenzyl | methyl | 84 | 120–122 |
| 2 | 3-methoxybenzyl | methyl | 78 | 74–76 |
| 3 | 4-methoxybenzyl | methyl | 55 | 126–128 |
| 4 | 2,3-dimethoxybenzyl | methyl | 91 | 99–101 |
| 5 | 2-bromobenzyl | methyl | 24 | 141–143 |
| 6 | phenethyl | ethyl | 53 | 133–135 |
| 7 | 2-methoxyphenethyl | methyl | 31 | 154–156 |
| 8 | 2'-cyanobiphenyl-4-methyl | methyl | 87 | 120–122 |
| 9 | phenylcarbamoyl | methyl | 91 | 89–91 |
| 10 | 2-phenyl-2-propenyl | methyl | 13 | 152–154 |
| 11 | allyl | methyl | 36 | 138–140 |
| 12 | 3-pyridylmethyl | methyl | 20 | 160–162 |
| 13 | 1-naphthylmethyl | methyl | 47 | 161–163 |
| 14 | 2-naphthylmethyl | methyl | 47 | 148–150 |
| 15 | α-methylbenzyl | methyl | 35 | 149–151 |
| 16 | 2-hydroxybenzyl | methyl | 18 | 178–180 |
| 17 | 2-methoxycarbonylbenzyl | methyl | 36 | 129–131 |
| 18 | 2-trifluoromethylbenzyl | methyl | 33 | 129–123 |
| 19 | 2-thenyl | methyl | 26 | 133–135 |

Working Example 15

2-(4-Aminophenyl)-4,7-dihydro-7-(2-methoxybenzyl)-3-(N-methyl-benzylaminomethyl)-4-oxothieno[2,3-b]pyridine-5-carboxylic acid ethyl ester To a solution of the compound 1 produced in Working Example 10 (0.60 g, 1.00 mmol) in methyl alcohol (10 ml)

was added iron powder (0.22 g, 4.0 mmol). The mixture was vigorously stirred under ice-cooling, then the reaction mixture was poured into ice-water, which was neutralized with sodium hydrogencarbonate, followed by extraction with ethyl acetate. The organic layer was washed with an aqueous sodium chloride solution and dried (Na$_2$SO$_4$), and the solvent distilled off under reduced pressure. The residue chromatographed on silica gel, followed by crystallization from chloroform-ether to give yellow needles (0.40 g, 71%), m.p.120°–122° C.

Elemental Analysis for C$_{33}$H$_{33}$N$_3$O$_4$S.3/2H$_2$O:

|  | C(%) | H(%) | N(%) |
|---|---|---|---|
| Calcd. | 66.65 | 6.10 | 7.07 |
| Found | 66.16 | 5.76 | 7.13 |

$^1$H-NMR (200 MHz, CDCl$_3$) [free amine] δ: 1.38(3H,t,J=7.2 Hz), 2.14(3H,s), 3.68(3H,s), 3.87(3H,s), 4.17(2H,s), 4.39(2H,q,J=7.2 Hz), 5.21(2H,s), 6.72(2H,d), 6.96(2H,t), 7.20(4H,m), 7.35(1H,t), 7.64(2H,d), 8.37(1H,s). IR(KBr) [hydrochloride]: 3454, 1690, 1603, 1499, 1386, 1317 cm$^{-1}$. FAB-Mass m/z 568(MH)$^+$ Working Example 16
4,7-Dihydro-5-hydroxymethyl-3-(N-methyl-N-benzylaminomethyl)-7-(2-methoxybenzyl)-2-(4-methoxyphenyl)-4-oxothieno[2,3-b]pyridine hydrochloride To a solution of the compound 2 produced in Working Example 10 (0.390 g, 0.67 mmol) in methyl alcohol (40 ml) was added an aqueous solution of potassium carbonate [prepared from potassium carbonate (0.185 g, 1.34 mmol) and water (8 ml)]. After stirring for 30 minutes at room temperature, the reaction mixture was then concentrated. The concentrate was partitioned between ethyl acetate and a saturated aqueous solution of sodium hydrogencarbonate. The aqueous layer was extracted with ethyl acetate. The combined organic layer was dried (MgSO$_4$), and then the solvent was distilled off under reduced pressure to give a pale yellow oil (0.36 g, 100%). To a solution of this oil (0.10 g) in tetrahydrofuran (5 ml) was added, under ice-cooling, a 1N HCl-ether solution (0.37 ml, 0.37 mmol), and the mixture was stirred for 10 minutes under ice-cooling. The reaction mixture was concentrated under reduced pressure, which was crystallized from ether to give the corresponding hydrochloride (0.105 g, 100%) as white crystals, m.p. [hydrochloride] 135°–140° C.

Elemental Analysis for C$_{32}$H$_{33}$N$_2$O$_4$SCl:

|  | C(%) | H(%) | N(%) |
|---|---|---|---|
| Calcd. | 66.60 | 5.76 | 4.85 |
| Found | 66.57 | 5.90 | 4.54 |

$^1$H-NMR (500 MHz, CDCl$_3$) [free amine] δ: 2.76(3H,s), 3.86(3H,s), 3.89(3H,s), 4.37(2H,s), 4.45(1H,br s), 4.55(1H, br s), 4.77(2H,s), 5.53(2H,s), 6.94(2H,d,J=8.2 Hz), 6.98(1H, t,J=7.4 Hz), 7.06(2H,br d), 7.3–7.45(7H,m), 7.50(1H,m), 8.27(1H,s). IR(KBr) [hydrochloride]: 3388, 1607, 1499, 1460, 1253 cm$^{-1}$. FAB-Mass m/z 541(MH)$^+$ Working Example 17
4,7-Dihydro-7-(2-methoxybenzyl)-2-(4-methoxyphenyl)-3-(N-methyl-N-benzylaminomethyl)-4-oxothieno[2,3-b]pyridine-5-carboxamide hydrochloride Anhydrous ammonia (22 ml) was dissolved in toluene (5 ml) at –78° C., to which was added, at –78° C., a toluene solution of diisobutyl aluminum hydride. The mixture was then warmed to room temperature, which was stirred for further 30 minutes. To this solution was added, at room temperature, a solution of the compound 15 produced in Reference Example 9 (0.25 g, 0.425 mmol) in toluene (4 ml). The mixture was stirred for further one hour at room temperature, which was then partitioned between dichloromethane and water. The aqueous layer was extracted with dichloromethane. The combined organic layer was washed with water, followed by drying over magnesium sulfate, followed by distilling off the solvent under reduced pressure. The residue was chromatographed on silica gel to give colorless crystals. To a solution of these crystals (0.130 g, 0.23 mmol) in tetrahydrofuran (5 ml) was added, under ice-cooling, an 1N solution of hydrogen chloride in ether (0.46 ml, 0.46 mmol), and the mixture was stirred for 10 minutes under ice-cooling. The reaction mixture was concentrated under reduced pressure, which was crystallized from ether to give the corresponding hydrochloride (0.143 g, 100%) as white crystals, m.p.152°–157° C.

Elemental Analysis for C$_{32}$H$_{32}$N$_3$O$_4$SCl:

|  | C(%) | H(%) | N(%) |
|---|---|---|---|
| Calcd. | 66.71 | 5.60 | 4.86 |
| Found | 66.28 | 5.80 | 4.51 |

$^1$H-NMR (500 MHz, CDCl$_3$) [free amine] δ: 2.84(3H,s), 3.87(3H,s), 3.88(3H,s), 4.35(1H,q,J=4.8 Hz), 4.6–4.8(3H, m), 5.31(2H,s), 6.09(1H,s), 6.95(1H,t,J=7.6 Hz), 6.99(1H,t, J=7.6 Hz), 7.03(2H,d,J=8.0 Hz), 7.30–7.36(4H,m), 7.40–7.50(5H,m), 8.94(1H,s), 9.70(1H,br), 11.61(1H,br). IR(KBr) [hydrochloride] : 1663, 1605, 1578, 1502, 1255 cm$^{-1}$. FAB-Mass m/z 554(MH)$^{30}$ Working Example 18
The compound 15 obtained in Working Example 9 was allowed to react, in substantially the same procedure as described in Working Example 17, with various amine derivatives to produce the compounds set forth in Table 15.

TABLE 15

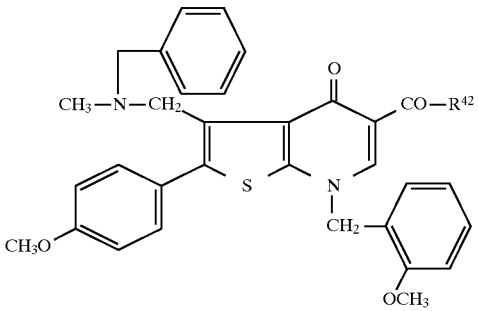

| W. Ex. 18 Cpd. No. | R$^{42}$ | Yield (%) | m.p. (°C.) |
|---|---|---|---|
| 1 | N,N-dimethylamino | 51 | 136–144 (hydrochloride) |
| 2 | N'-benzylpiperazino | 26 | 168–174 (hydrochloride) |
| 3 | piperidino | 38 | 133–142 (hydrochloride) |

Working Example 19
4,7-Dihydro-7-(2-methoxybenzyl)-2-(3-methoxyphenyl)-3-methyl-oxothieno[2,3-b]pyridine-5-carboxylic acid ethyl ester To a mixture of the compound 7 produced in Working Example 3 (0.615 g, 1.41 mmol), 3-methoxyphenyl boric acid (9.321 g, 2.11 mmol), 2M sodium carbonate (3.53 ml, 7.06 mmol) and 1,2-dimethoxyethane (30 ml) was added, in an atmospher of argon, tetrakis (triphenylphosphine) palladium (O) (0.163 g, 0.141 mmol), and the mixture was refluxed for 24 hours. After cooling, to the reaction mixture was added ethyl acetate. Insolubles were filtered off with celite. The filtrate was partitioned between ethyl acetate and an aqueous sodium chloride solution. The aqueous layer was extracted with ethyl acetate. The combined organic layer was washed with a saturated aqueous sodium chloride solution and dried over magnesium sulfate. The solvent was distilled off under reduced pressure, and the residue was chromatographed on silica gel to give white amorphous (0.446 g, 68%).

Elemental Analysis for $C_{26}H_{25}NO_5S \cdot 0.5H_2O$:

|  | C(%) | H(%) | N(%) |
|---|---|---|---|
| Calcd. | 66.08 | 5.55 | 2.96 |
| Found | 66.33 | 5.40 | 2.91 |

$^1$H-NMR (200 MHz, CDCl$_3$) δ: 1.41(3H,t,J=7.1 Hz), 2.69(3H,s), 3.84(3H,s), 3.87(3H,s), 4.39(2H,q,J=7.1 Hz), 5.16(2H,s), 6.87–7.02(5H,m), 7.22–7.42(3H,m), 8.42(1H,s). IR(KBr): 3440, 2938, 1727, 1688, 1607, 1493, 1465 cm$^{-1}$.

Working Example 20

4,7-Dihydro-2-(4-methoxyphenyl)-3-(N-methyl-N-benzylaminomethyl)-7-(2-methylthiobenzyl)-4-oxothieno[2,3-b]pyridine-5-carboxylic acid ethyl ester hydrochloride A mixture of the compound produced in Reference Example 18 (0.12 g, 0.26 mmol), K$_2$CO$_3$ (54 mg, 0.39 mmol), 2-methylthiobenzyl chloride (54 mg, 0.31 mmol), KI (18 mg, 0.1 mmol) and dimethylformamide (3 ml) was stirred for 2 hours at 50° C. After cooling, the solvent was distilled off under reduced pressure. The residue was chromatographed on silica gel, which was dissolved in ethyl acetate (20 ml). To the solution was added an 1N hydrogen chloride solution in ether (0.33 ml), which was concentrated under reduced pressure. The concentrate was crystallized from ether to give the corresponding hydrochloride as pale yellow crystals (0.1 g, 64%), m.p.118°–120° C.

Elemental Analysis for $C_{34}H_{34}N_2O_4S_2 \cdot HCl \cdot 0.4H_2O$:

|  | C(%) | H(%) | N(%) |
|---|---|---|---|
| Calcd. | 63.57 | 5.62 | 4.36 |
| Found | 63.81 | 5.82 | 4.49 |

$^1$H-NMR (200 MHz, CDCl$_3$) δ: 1.38(3H,t,J=7.1 Hz), 2.52(3H,s), 2.94(3H,s), 3.88(3H,s), 4.38(3H,q, like,J=7.1 Hz), 4.60(1H brs), 4.75(2H,brs), 5.39(2H,s), 7.04(2H,d,J= 8.7 Hz), 7.23–7.53(11H,m), 8.39(1H,s), 11.82(1H,brs). IR(KBr): 3406, 2980, 1719, 1605, 1502 cm$^{-1}$.

Working Example 21

Employing, as the starting material, the compound produced in Reference Example 18, reactions were conducted with various halogen compounds in substantially the same manner as described in Working Example 20 to produce the compounds set forth in Table 16.

TABLE 16

[Structure: CH$_3$-N-CH$_2$- with benzyl group, attached to thieno[2,3-b]pyridine core with CH$_3$O-C$_6$H$_4$- substituent, S, N-R$^{36}$, and COOC$_2$H$_5$ group, with C=O]

| W. Ex. 21 Cpd. No. | R$^{36}$ | Yield (%) | m.p. (°C.) |
|---|---|---|---|
| 1 | 3-methoxybenzyl | 65 | 109–113 (hydrochloride) |
| 2 | 4-methoxybenzyl | 65 | 200–204 (hydrochloride) |
| 3 | 2-fluorobenzyl | 61 | 203–207 (hydrochloride) |
| 4 | 1-naphthylmethyl | 62 | 187–192 (hydrochloride) |
| 5 | 2-naphthylmethyl | 77 | 122–125 (hydrochloride) |
| 6 | 2-methoxyphenethyl | 57 | 76–81 (hydrochloride) |
| 7 | 2-trifluoromethyl-benzyl | 66 | 189–194 (hydrochloride) |

Working Example 22

4,7-Dihydro-5-formyl-7-(2-methoxybenzyl)-2-(4-methoxyphenyl)-3-(N-methyl-N-benzylaminomethyl)-4-oxothieno[2,3-b]pyridine To a solution of the compound produced in Working Example 16 (0.54 g, 0.10 mmol) in chloroform (10 ml) was added active manganese dioxide (0.27 g), and the mixture was stirred for one hour at room temperature. The reaction mixture was filtered with celite, and then celite was washed with chloroform. The combined filtrate was concentrated. The concentrate was chromatographed on silica gel to give a yellow solid, which was recrystallized from ethyl acetate-ether to give white crystals (0.014 g, 25%), m.p.181°–185° C.

Elemental Analysis for $C_{32}H_{30}N_2O_4S \cdot 0.8SiO_2$:

|  | C(%) | H(%) | N(%) |
|---|---|---|---|
| Calcd. | 65.51 | 5.15 | 4.77 |
| Found | 63.25 | 5.13 | 5.25 |

$^1$H-NMR (200 MHz, CDCl$_3$) δ: 2.40(3H,s), 3.85(3H,s), 3.87(3H,s), 3.8–4.0(2H,br), 4.33(2H,s), 5.23(2H,s), 6.9–7.1 (5H,m), 7.2–7.4(7H,m), 7.64(1H,d,J=7.9 Hz), 8.31(1H,s), 10.45(1H,s). IR(KBr): 2934, 1688, 1603, 1502, 1386, 1255 cm$^{-1}$. FAB-Mass m/z 539(MH)$^+$

Working Example 23

2-(4-Acetylaminophenyl)-4,7-dihydro-7-(2-methoxybenzyl)-3-(N-methyl-N-benzylaminomethyl)-4-oxothieno[2,3-b]pyridine-5-carboxylic acid ethyl ester To a solution of the compound produced in Working Example 15 (0.11 g, 0.20 mmol) were added, with ice-cooling, acetic anhydride (1 ml) and pyridine (0.29 g, 10.0 mmol). The mixture was stirred for 8 hours at room temperature. The reaction mixture was poured into a saturated aqueous solution of sodium hydrogencarbonate, which was extracted with dichloromethane. The extract was washed with an aqueous sodium chloride solution and dried (Na$_2$SO$_4$), followed by distilling off the solvent under reduced pressure. The residue was chromatographed on silica gel, followed by recrystalization from ether to give white crystalline powder (0.07 g, 58%), m.p.161°–163° C.

$^1$H-NMR (500 MHz, DMSO-d$_6$) δ: 1.35(3H,t,J=7.2 Hz), 2.10(3H,s), 2.58(3H,s), 3.82(3H,s), 4.2–4.4(4H,m), 4.42 (1H,d), 4.58(1H,d), 5.51(2H,s), 6.70(1H,t), 7.05(1H,d), 7.1–7.3(1H,m), 7.3–7.5(7H,m), 7.68(1H,s), 7.78(2H,d), 8.88(1H,s), 10.33(1H,s). IR(KBr): 3258, 1717, 1686, 1605, 1495, 1317, 1253 cm$^{-1}$. FAB-Mass m/z 610(MH)$^+$ Working Example 24

4,7-Dihydro-2-(4-formylaminophenyl)-7-(2-methoxybenzyl)-3-(N-methyl-N-benzylaminomethyl)-4-oxothieno[2,3-b]pyridine-carboxylic acid ethyl ester To a solution of the compound produced in Working Example 15 (0.23 g, 4.00 mmol) in dichloromethane (5 ml) was added, with ice-cooling, a mixture of acetic acid anhydride and formic acid [prepared by adding, under ice-cooling, formic acid (99%, 6.00 mmol) to acetic anhydride (0.41 g, 4.00 mmol), followed by stirring for 2 hours at 60° C.]. The mixture was stirred for 8 hours at room temperature.

The reaction mixture was poured into a saturated aqueous solution of sodium hydrogencarbonate, which was extracted with dichloromethane. The extract was washed with an aqueous sodium chloride solution and dried (Na$_2$SO$_4$), then the solvent was distilled off under reduced pressure. The residue was chromatographed on silica gel, followed by recrystalization from chloroform-ether to give white needles (0.17 g, 72%), m.p.185°–187° C.

| Elemental Analysis for C$_{34}$H$_{33}$N$_3$O$_5$S.0.5H$_2$O: | | | |
|---|---|---|---|
| | C(%) | H(%) | N(%) |
| Calcd. | 67.53 | 5.67 | 6.95 |
| Found | 67.04 | 5.28 | 6.97 |

$^1$H-NMR (200 MHz, CDCl$_3$) δ: 1.38(3H,t,J=7.2 Hz), 2.13(3H,s), 3.65(2H,s), 3.87(3H,s), 4.17(2H,s), 4.38(2H,q), 5.18(2H,s), 6.97(1H,t), 7.1–7.3(8H,m), 7.38(1H,t), 7.5–7.7 (2H,m), 7.8–7.9(2H,m), 8.40(1H,s), 8.44(1H,s). IR(KBr): 3336, 2978, 1723, 1605, 1495, 1439, 1305 cm$^{-1}$. FAB-Mass m/z 596(MH)$^+$ Working Example 25

Employing, as the starting compounds, the compound produced in Reference Example 11 and derived from the compound in Reference Example 18 with reduction in accordance with substantially the same method as described in Reference Example 11, in accordance with substantially the same method as described in Working Example 4, the compound shown in Table 17 was produced.

TABLE 17

| W. Ex. 25 Cpd. No. | R$^{31}$ | R$^{32}$ | R$^{36}$ | Yield (%) | m.p. (°C.) |
|---|---|---|---|---|---|
| 1 | methyl | 4-methoxy-phenyl | 2-fluoro-benzyl | 76 | 184–185 |
| 2 | N-methyl-N-benzyl-aminomethyl | 4-methoxy-phenyl | 2-fluoro-benzyl | 92 | amor-phous |

Working Example 26

Employing, as the starting compound, the compound produced in Working Example 7, in accordance with substantially the same method as described in Working Example 8, the compounds shown in Table 18 were produced.

TABLE 18

| W. Ex. 26 Cpd. No. | R$^{32}$ | R$^{36}$ | Yield (%) | m.p. (°C.) |
|---|---|---|---|---|
| 1 | 4-nitrophenyl | 2-fluoro-benzyl | 83 | 140–144 |
| 2 | 4-nitrophenyl | 2,6-difluoro-benzyl | 91 | 145–147 |
| 3 | 4-nitrophenyl | 2-chloro-6-fluorobenzyl | 78 | 175–177 |

Working Example 27

Employing, as the starting compound, the compound produced in Working Example 26, in accordance with substantially the same reaction as described in Working Example 15, the compounds shown in Table 19 were produced.

TABLE 19

[Structure: pyridine-thiophene fused system with CH₃-N-CH₂-benzyl group, R³², S, N-R³⁶, and COOCH₂CH₃ substituents]

| W. Ex. 27 Cpd. No. | R³² | R³⁶ | Yield (%) | m.p. (°C.) |
|---|---|---|---|---|
| 1 | 4-aminophenyl | 2-fluorobenzyl | 79 | 158–160 |
| 2 | 4-aminophenyl | 2,6-difluoro-benzyl | 96 | 195–196 |
| 3 | 4-aminophenyl | 2-chloro-6-fluorobenzyl | 71 | 144–146 |

Working Example 28

4,7-Dihydro-7-(2-fluorobenzyl)-5-formyl-2-(4-methoxyphenyl)-3-methyl-4-oxothieno[2,3-b]pyridine:

The compound produced in Working Example 25 (4.10 g) was stirred for one hour at room temperature together with manganese dioxide (20.5 g) in chloroform (120 ml). The reaction mixture was filtered with celite. The filtrate was concentrated to dryness, the concentrate was chromatographed on silica gel, followed by recristalization from methylene chloride-ethyl acetate to give colorless crystals (3.72 g, yield 83%).

$^1$H-NMR (200 MHz, CDCl$_3$) δ ppm: 2.66(3H,s), 3.85(3H,s), 5.26(2H,s), 6.96(2H,d), 7.1–7.4(6H,m), 8.17(1H,s), 10.44(1H,s).

Working Example 29

4,7-Dihydro-7-(2-fluorobenzyl)-5-(1-hydroxyethyl)-2-(4-methoxyphenyl)-3-methyl-4-oxothieno[2,3-b]pyridine:

The compound produced in Working Example 28 (1.0 g) was dissolved in anhydrous tetrahydrofuran (50 ml). To the solution was added, with ice-cooling, methyl magnesium bromide (0.35 g), and the mixture was warmed to room temperature, followed by stirring for further 3 hours. The reaction mixture was filtered with celite. The filtrate was concentrated to dryness. To the residue were added a saturated aqueous solution of ammonium chloride (20 ml) and ethyl acetate (20 ml), then the mixture was stirred. The aqueous layer was extracted with ethyl acetate (20 ml). The combined organic layer was dried. The solvent was distilled off under reduced pressure. The residue was chromatographed on silica gel to give a yellow amorphous (1.10 g, yield 100%).

$^1$H-NMR (200 MHz, CDCl$_3$) δ ppm: 1.55(3H,d), 2.66(3H,s), 3.84(3H,s), 4.94(1H,q), 5.20(2H,s), 6.95(2H,d), 7.1–7.2(3H,m), 7.3–7.4(3H,m), 7.44(1H,s).

Working Example 30

The compound produced in Working Example 28 was subjected to reactions, in accordance with substantially the same manner as described in Working Example 29, with various Grignard's reagents in place of methyl magnesium bromide, to give the compounds set forth in Table 20.

TABLE 20

[Structure: thieno[2,3-b]pyridine with CH₃O-phenyl, S, CH₃, CH(OH)R', N-CH₂-phenyl-R substituents]

| W. Ex. 30 Cpd. No. | R | R' | Yield (%) | m.p. (°C.) |
|---|---|---|---|---|
| 1 | 2-methoxy | methyl | 100 | amorphous |
| 2 | 2-fluoro | ethyl | 97 | amorphous |
| 3 | 2-fluoro | n-propyl | 92 | amorphous |
| 4 | 2-fluoro | phenyl | 71 | amorphous |
| 5 | 2-fluoro | isopropyl | 85 | amorphous |
| 6 | 2-fluoro | n-butyl | 95 | amorphous |
| 7 | 2-fluoro | sec-butyl | 72 | amorphous |
| 8 | 2-fluoro | t-butyl | 77 | amorphous |
| 9 | 2-fluoro | n-pentyl | 75 | amorphous |
| 10 | 2-fluoro | cyclopentyl | 75 | amorphous |
| 11 | 2-fluoro | n-hexyl | 68 | amorphous |
| 12 | 2-fluoro | cyclohexyl | 100 | amorphous |
| 13 | 2-fluoro | 4-fluoro-phenyl | 92 | amorphous |
| 14 | 2-fluoro | benzyl | 46 | amorphous |

Working Example 31

5-Acetyl-4,7-dihydro-7-(2-fluorobenzyl)-2-(4-methoxyphenyl)-3-methyl-4-oxothieno[2,3-b]pyridine The compound produced in Working Example 29 (0.50 g) was stirred for 3 hours at 40° C. together with manganese dioxide in chloroform (50 ml). The reaction mixture was filtrated with celite. The filtrate was concentrated to dryness. The residue was recrystallized from hexane-ethyl acetate to give colorless crystals (0.35 g, yield 70%), m.p.215°–216° C.

| Elemental Analysis for C$_{24}$H$_{20}$NO$_3$S: | | | |
|---|---|---|---|
| | C(%) | H(%) | N(%) |
| Calcd. | 68.44 | 4.78 | 3.33 |
| Found | 68.35 | 4.70 | 3.41 |

$^1$H-NMR (200 MHz, CDCl$_3$) δ ppm: 2.66(3H,s), 2.78(3H,s), 3.85(3H,s), 5.25(2H,s), 6.96(2H,d), 7.1–7.5(6H,m), 8.37 (1H,s). FAB-Mass m/z 422(MH)$^+$

Working Example 32

Employing the compound produced in Working Example 30, in accordance with substantially the same procedure as described in Working Example 31, the compounds set forth in Table 21 were produced.

TABLE 21

[Structure: thieno[2,3-b]pyridine core with CH₃ group, 4-methoxyphenyl, COR' group, and N-CH₂-phenyl-R substituent]

W. Ex. 32

| Cpd. No. | R | R' | Yield (%) | m.p. (°C.) |
|---|---|---|---|---|
| 1 | 2-methoxy | methyl | 80 | 156–157 |
| 2 | 2-fluoro | ethyl | 67 | 180–181 |
| 3 | 2-fluoro | n-propyl | 65 | 170–171 |
| 4 | 2-fluoro | phenyl | 84 | 183–184 |
| 5 | 2-fluoro | isopropyl | 70 | 172–174 |
| 6 | 2-fluoro | n-butyl | 83 | 162–163 |
| 7 | 2-fluoro | sec-butyl | 75 | 132–133 |
| 8 | 2-fluoro | t-butyl | 44 | 141–144 |
| 9 | 2-fluoro | n-pentyl | 88 | 145–147 |
| 10 | 2-fluoro | cyclopentyl | 62 | 182–183 |
| 11 | 2-fluoro | n-hexyl | 66 | 125–126 |
| 12 | 2-fluoro | cyclohexyl | 69 | 191–192 |
| 13 | 2-fluoro | 4-fluoro-phenyl | 86 | 187–188 |

TABLE 22

[Structure: thieno[2,3-b]pyridine core with BrCH₂ group, 4-methoxyphenyl, COR' group, and N-CH₂-phenyl-R substituent]

W. Ex. 34

| Cpd. No. | R | R' | Yield (%) | m.p. (°C.) |
|---|---|---|---|---|
| 1 | 2-methoxy | methyl | 68 | 206–208 |
| 2 | 2-fluoro | ethyl | 48 | 186–187 |
| 3 | 2-fluoro | n-propyl | 65 | 165–166 |
| 4 | 2-fluoro | phenyl | 75 | 145–147 |
| 5 | 2-fluoro | isopropyl | 81 | 123–124 |
| 6 | 2-fluoro | n-butyl | 63 | 173–174 |
| 7 | 2-fluoro | sec-butyl | 68 | 146–148 |
| 8 | 2-fluoro | t-butyl | 80 | 98–99 |
| 9 | 2-fluoro | isobutyl | 74 | 187–189 |
| 10 | 2-fluoro | n-pentyl | 55 | 168–169 |
| 11 | 2-fluoro | cyclopentyl | 45 | 166–167 |
| 12 | 2-fluoro | n-hexyl | 54 | 146–147 |
| 13 | 2-fluoro | cyclohexyl | 61 | 169–170 |
| 14 | 2-fluoro | 4-fluoro-phenyl | 94 | 135–136 |

Working Example 33

5-Acetyl-3-bromomethyl-4,7-dihydro-7-(2-fluorobenzyl)-2-(4-methoxyphenyl)-4-oxothieno[2,3-b]pyridine The compound produced in Working Example 31 (0.32 g) was dissolved in carbon tetrachloride (60 ml). The solution was refluxed for 2 hours together with N-bromosuccinimide (0.144 g) and α,α'-azobisisobutyronitrile (0.013 g). After cooling, to the reaction mixture was added chloroform. The mixture was washed with a saturated aqueous solution of sodium hydrogencarbonate (20 ml). The organic layer was dried. The solvent was distilled off under reduced pressure. The residue was chromatographed on silica gel to give a yellow amorphous, which was recrystallized from chloroform-isopropyl ether-ethyl acetate to give colorless needles (0.29 g, yield 75%), m.p.226°–228° C.

$^1$H-NMR (200 MHz, CDCl$_3$) δ ppm: 2.81(3H,s), 3.86(3H, s), 5.03(2H,s), 5.26(2H,s), 7.03(2H,d), 7.1–7.5(4H,m), 7.55 (2H,d), 8.38(1H,s).

Working Example 34

Employing the compounds produced in Working Example 32 as the starting materials, in accordance with substantially the same reactions as described in Working Example 33, the compounds set forth in Table 22 were produced.

Working Example 35

5-Acetyl-4,7-dihydro-7-(2-fluorobenzyl)-2-(4-methoxyphenyl)-3-(N-methyl-N-benzylaminomethyl)-4-oxothieno[2,3-b]pyridine The compound produced in Working Example 33 (0.25 g) was dissolved in dimethylformamide (20 ml). To the solution were added, at room temperature, diisopropyl ethylamine (0.079 g) and N-benzylmethylamine (0.074 g). The mixture was stirred for 90 minutes at room temperature. The reaction mixture was concentrated to dryness under reduced pressure. The residue was partitioned between ethyl acetate (100 ml) and a saturated aqueous solution of sodium hydrogencarbonate (50 ml). The aqueous layer was extracted with ethyl acetate (100 ml). The combined organic layer was dried. The solvent was distilled off, and the residue was chromatographed on silica gel to give a yellow amorphous (0.27 g). The amorphous was dissolved in methylene chloride (5 ml), to which was added, with ice-cooling, an 1N solution of hydrogen chloride in ether (1 ml). The resulting crystalline precipitate was collected by filtration to give a titled compound (0.22 g, yield 77%), m.p.185°–193° C.

| Elemental Analysis for C$_{32}$H$_{30}$N$_2$O$_3$SClF.2H$_2$O: | | | |
|---|---|---|---|
| | C(%) | H(%) | N(%) |
| Calcd. | 62.68 | 5.59 | 4.57 |
| Found | 63.16 | 5.62 | 4.56 |

$^1$H-NMR (200 MHz, CDCl$_3$) δ ppm: 2.80(3H,s), 2.87(3H, s), 3.88(3H,s), 4.3–4.44(1H,m), 4.6–4.8(3H,m), 5.35(2H,s), 7.03(2H,d), 7.2–7.5(11H,m), 8.48(1H,s), 11.8(1H,br s). FAB-Mass m/z 541(MH)$^+$

Working Example 36

Employing the compounds produced in Working Example 34 as starting materials, in accordance with substantially the same reactions as described in Working Example, the compounds set forth in Table 23 were produced.

TABLE 23

[Structure: CH3-N-CH2 group with benzyl, connected to thieno[2,3-b]pyridine core with CH3O-phenyl, COR' substituent, N-CH2-phenyl-R group, ·HCl]

| W. Ex. 36 Cpd. No. | R | R' | Yield (%) | m.p. (°C.) |
|---|---|---|---|---|
| 1 | 2-methoxy | methyl | 100 | 124–130 |
| 2 | 2-fluoro | ethyl | 83 | 163–172 |
| 3 | 2-fluoro | n-propyl | 62 | 145–150 |
| 4 | 2-fluoro | phenyl | 50 | 154–161 |

Working Example 37

4,7-Dihydro-7-(2-fluorobenzyl)-3-(N-methyl-N-benzylaminomethyl)-2-(4-N'-methylureidophenyl)-4-oxothieno[2,3-b]pyridine-5-carboxylic acid ethyl ester To a solution of the compound produced in Working Example 26 (0.11 g, 0.20 mmol) in tetrahydrofuran (5 ml) was added pyridine (0.5 ml). To the mixture was added dropwise, with ice-cooling, methyl isocyanate (0.064 ml). The mixture was stirred for 4 hours at room temperature. The reaction mixture was then concentrated under reduced pressure. The concentrate was dissolved in chloroform, which was washed with an aqueous sodium chloride solution and dried ($Na_2SO_4$). The solvent was distilled off under reduced pressure, and the residue was chromatographed on silica gel, followed by recrystalization from ethanol-ethyl acetate to give white needles (0.09 g, 73%), m.p.216°–220° C.

Elemental Analysis for $C_{34}H_{33}N_4O_4SF.2H_2O$:

|  | C(%) | H(%) | N(%) |
|---|---|---|---|
| Calcd. | 62.95 | 5.75 | 8.64 |
| Found | 63.22 | 5.60 | 8.39 |

$^1$H-NMR (500 MHz, DMSO-$d_3$) δ: 1.44(3H,t), 2.25(3H, br s), 2.84(3H,s), 4.35(2H,br s), 4.43(2H,q), 4.90(2H,br s), 5.62(2H,s), 7.20–7.32(7H,m), 7.45–7.60(6H,m), 8.85(1H,s). IR(KBr): 3308, 1698, 1605, 1499, 1319, 1236, 1183 $cm^{-1}$. Mass m/z 613(MH)$^+$

Working Example 38

Employing the compounds produced in Working Example 27 as starting materials, in accordance with substantially the same reactions as described in Working Examples 23, 24 and 37, the compounds set forth in Table 24 were produced as the corresponding hydrochlorides.

TABLE 24

[Structure: CH3-N-CH2 with benzyl, thieno[2,3-b]pyridine core with $R^{32}$, COOCH2CH3, N-$R^{36}$]

| W. Ex. 38 Cpd. No. | $R^{21}$ | $R^{22}$ | Yield (%) | m.p. (°C.) |
|---|---|---|---|---|
| 1 | 4-acetyl-aminophenyl | 2-fluorobenzyl | 84 | 118–120 |
| 2 | 4-propionyl-aminophenyl | 2-fluorobenzyl | 74 | 221–223 |
| 3 | 4-isobutyryl-aminophenyl | 2-fluorobenzyl | 72 | 118–192 |
| 4 | 4-benzoyl-aminophenyl | 2-fluorobenzyl | 53 | 141–143 |
| 5 | 4-methane-sulfonamido-phenyl | 2-fluorobenzyl | 95 | >300 |

Working Example 39

5-Benzylmethylaminomethyl-2,4(1H,3H)-dioxo-1-(2-fluorobenzyl)-6-(4-methoxyphenyl)-3-phenylthieno[2,3-d]pyrimidine hydrochloride To a solution of the compound 15 produced in Reference Example 29 (0.150 g, 0.310 mmol) in dimethylformamide (10 ml), with ice-cooling, were added ethyldiisopropylamine (0.08 ml, 0.460 mmol) and methylbenzylamine (0.05 ml, 0.370 mmol). After stirring for 2 hours at room temperature, the reaction mixture was concentrated. The residue was partitioned between ethyl acetate and a saturated aqueous solution of sodium bicarbonate. The aqueous layer was extracted with ethyl acetate. The combined organic layer was dried ($MgSO^4$). The solvent was distilled off under reduced pressure, and the residue was chromatographed on silica gel to give a colourless oil (0.159 g, 97%). To the solution of this oil in ethyl acetate (4 ml) was added, with ice-cooling, an 1N solution of hydrogen chloride in ether (0.3 ml). After stirring for 10 minutes under ice-cooling, the reaction mixture was concentrated with reduced pressure. The residue was crystallized from ethyl acetate-ether to give a titled hydrochloride (0.144 g) as white crystals. m.p. [hydrochloride] 140°–143° C.

Elemental Analysis for $C_{35}H_{30}N_3O_3SF.HCl.H_2O$:

|  | C(%) | H(%) | N(%) |
|---|---|---|---|
| Calcd. | 65.05 | 5.14 | 6.50 |
| Found | 65.14 | 5.03 | 6.37 |

$^1$H-NMR (200 MHz, CDCl$_3$) [free amine]δ: 2.07(3H,s), 3.57(2H,s), 3.86(3H,s), 3.90(3H,s), 5.30(2H,s), 6.94(2H,d, J=8.8 Hz), 7.05–7.60(14H,m), 7.66(2H,d,J=8.8 Hz). IR(KBr) [hydrochloride]: 1711, 1665, 1543, 1477 $cm^{-1}$.

Working Example 40

Starting from the compounds produced in Reference Example 28, compounds set forth in Table 25 were produced in accordance with the method described in Working Example 39.

TABLE 25

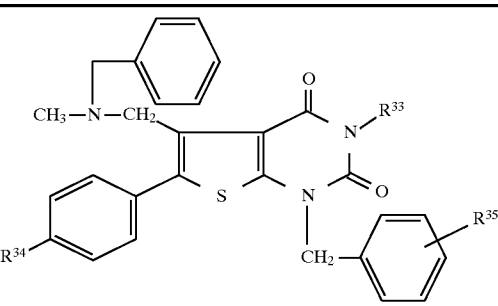

| W. Ex. 40 Cpd. No. | R³³ | R³⁵ | R³⁴ | Yield (%) | m.p. (°C.) |
|---|---|---|---|---|---|
| 1 | methyl | 2-methoxy | methoxy | 46 | 119–122 |
| 2 | methyl | 2-fluoro | methoxy | 97 | 128–131 |
| 3 | phenyl | 2-methoxy | methoxy | 95 | 97–105 |
| 4 | phenyl | 2-fluoro | nitro | 100 | 140–143 |
| 5 | phenyl | 3-fluoro | methoxy | 97 | 152–156 |
| 6 | phenyl | 4-fluoro | methoxy | 100 | 165–170 |
| 7 | phenyl | 2,4-difluoro | methoxy | 77 | 155–160 |
| 8 | phenyl | 2,6-difluoro | methoxy | 100 | 160–162 |
| 9 | phenyl | 2-chloro, 6-fluoro | methoxy | 98 | 150–155 |
| 10 | phenyl | 2-methylthio | methoxy | 76 | 152–158 |
| 11 | benzyl | 2-fluoro | methoxy | 89 | 128–134 |
| 12 | benzyl | 2,6-difluoro | methoxy | 100 | 123–127 |
| 13 | 4-methoxyphenyl | 2-fluoro | methoxy | 93 | 150–155 |
| 14 | 4-methoxyphenyl | 2,6-difluoro | methoxy | 84 | 153–157 |
| 15 | cyclohexyl | 2-fluoro | methoxy | 93 | 144–150 |
| 16 | cyclohexyl | 2,6-difluoro | methoxy | 97 | 145–150 |
| 17 | phenyl | 2,6-difluoro | nitro | 93 | 155–160 |
| 18 | 2-methoxyphenyl | 2-fluoro | methoxy | 93 | 152–153 |
| 19 | 2-methoxyphenyl | 2,6-difluoro | methoxy | 100 | 148–150 |
| 20 | 3-methoxyphenyl | 2-fluoro | methoxy | 92 | 155–158 |
| 21 | 3-methoxyphenyl | 2,6-difluoro | methoxy | 91 | 160–163 |
| 22 | 2-chlorophenyl | 2-fluoro | methoxy | 97 | 147–152 |
| 23 | 2-chlorophenyl | 2,6-difluoro | methoxy | 98 | 150–155 |
| 24 | 3-chlorophenyl | 2-fluoro | methoxy | 100 | 148–153 |
| 25 | 3-chlorophenyl | 2,6-difluoro | methoxy | 100 | 152–157 |
| 26 | 4-chlorophenyl | 2-fluoro | methoxy | 91 | 161–164 |
| 27 | 4-chlorophenyl | 2,6-difluoro | methoxy | 86 | 145–146 |

Working Example 41
3-Cyanomethyl-4,7-dihydro-7-(2-fluorobenzyl)-2-(4-methoxyphenyl)-4-oxothieno[2,3-b]pyridine-5-carboxylic acid ethyl ester To a suspension of the compound produced in Working Example 7 (Compound No.10) (0.80 g, 1.51 mmol) in dimethyl sulfoxide (DMSO) was added, at room temperature, sodium cyanide (0.084 g, 1.66 mmol). The reaction mixture was heated up to 60° C., which was stirred for further 4 hours. After cooling to room temperature, the reaction mixture was poured into water. The mixture was extracted with ethyl acetate (50 ml×2). The extract was washed with water, which was then dried. The resulting solution was evaporated to dryness to leave a pale yellow oil (0.77 g). This product was used in the following working example 42 without purification.

Working Example 42
4,7-Dihydro-3-ethoxycarbonylmethyl-7-(2-fluorobenzyl)-2-(4-methoxyphenyl)-4-oxothieno[2,3-b] pyridine-5-carboxylic acid ethyl ester To a solution of the compound produced in Working Example 41 (0.77 g) in anhydrous ethanol (250 ml) was added dropwise carefully, at room temperature, conc. sulfuric acid (50 drops). The reaction mixture was refluxed for 15 hours. The reaction mixture was neutralized, with ice-cooling, with an excess volume of an aqueous solution of sodium hydrogencarbonate, which was extracted with ethyl acetate (500 ml×3). The extract was washed with water and dried., followed by concentration under reduced pressure to give a brownish solid (0.72 g). This solid was chromatographed on silica gel to give crystals, followed by recrystallization from ethyl acetate-hexane to give colorless crystals (0.28 g, overall yield 35%), m.p.199°–201° C.

| Elemental Analysis for $C_{28}H_{26}NO_6SF.0.7H_2O$: | | | |
|---|---|---|---|
| | C(%) | H(%) | N(%) |
| Calcd. | 62.72 | 5.02 | 2.61 |
| Found | 62.57 | 4.84 | 2.53 |

$^1$H-NMR (300 MHz, CDCl$_3$) δ: 1.38(3H,t,J=7.2 Hz), 2.68(3H,t,J=7.2 Hz), 3.84(3H,s), 4.04(2H,s), 4.16(2H,q,J=7.2 Hz), 4.37(2H,q,J=7.2 Hz), 5.23(2H,s), 6.92–7.42(8H,m), 8.36(1H,s). IR (KBr): 3430, 1727, 1611, 1502, 1255, 1183, 1033, 762, 520 cm$^{-1}$.

Working Example 43
4,7-Dihydro-7-(2-fluorobenzyl)-3-hydroxyethyl-2-(4-methoxyphenyl)-4-oxothieno[2,3-b]pyridine-5-carboxylic acid ethyl ester To a solution of the compound (0.21 g) produced in Working Example 42 in anhydrous tetrahydrofuran (THF) was added, under ice-cooling, lithium aluminum hydride. The reaction mixture was allowed to warm to room temperature, and stirred for further one hour, which was poured into a saturated aqueous solution of ammonium chloride, followed by extraction with ethyl acetate (100 ml×3). The extract was washed with a saturated aqueous solution of ammonium chloride, and dried, followed by filtration. The filtrate was concentrated under reduced pressure to give a solid, which was chromatographed on silica gel to give a pale yellow amorphous (0.16 g, 66%).

$^1$H-NMR (300 MHz, CDCl$_3$) δ: 0.90(3H,t,J=7.2 Hz), 1.70(1H,br s), 3.29(2H,t,J=6.0 Hz), 3.84(3H,s), 4.20–4.23 (2H,m), 4.37(2H,q,J=7.2 Hz), 5.29(2H,s), 6.93–7.34(8H,m), 8.45(1H,s). FAB-Mass m/z 482(MH)$^+$.

Working Example 44
4,7-Dihydro-7-(2-fluorobenzyl)-2-(4-methoxyphenyl)3-(N-methyl-N-benzylaminoethyl)-4-oxothieno[2,3-b]pyridine-5-carboxylic acid ethyl ester To a solution of the compound produced in Working Example 43 (0.08 g,0.67 mmol) in methylene chloride (5 ml) was added, with ice-cooling, an excess volume of phorphorus tribromide (0.5 ml). The reaction mixture was allowed to warm to room temperature and stirred for further one hour, to which was added ethyl acetate (20 ml). The mixture was washed with water and dried. The filtrate was concentrated under reduced pressure to give a solid. This solid was dissolved in dimethylformamide (DMF) (5 ml), to which were added an excess amount of diisopropyl ethylamine (100 mg) and N-benzylmethyl amine (100 mg). The reaction mixture was stirred for further one hour, to which was added ethyl acetate (20 ml), followed by washing with a saturated aqueous solution of sodium hydrogencarbonate and a saturated aqueous sodium chloride solution, and, then, drying. The dried solution was concentrated under reduced pressure to give a solid, which was chromatographed on silica gel to give a pale yellow amorphous (0.005 g, 4%).

$^1$H-NMR (300 MHz, CDCl$_3$) δ: 1.40(3H,t,J=7.2 Hz), 2.70(3H,s), 3.30–3.60(4H,m), 3.83(3H,s), 4.06(2H,s), 4.40 (2H,q,J=7.2 Hz), 5.28(2H,s), 6.56–7.51(13H,m), 8.45(1H, s). FAB-Mass m/z 585(MH)$^+$.

Working Example 45

5-(1-Acetoxyethyl)-4,7-dihydro-7-(2-fluorobenzyl)-2-(4-methoxyphenyl)-3-methyl-4-oxothieno[2,3-b]pyridine To a solution of the compound produced in Working Example 29 (0.55 g, 1.32 mmol) in pyridine (25 ml) was added, under ice-cooling, anhydrous acetic acid (2.69 g, 26.3 mmol). The reaction mixture was allowed to warm to room temperature, which was stirred for further 24 hours. The reaction mixture was concentrated under reduced pressure. The concentrate was partitioned between ethyl acetate (50 ml) and 1N HCl (10 ml). The aqueous layer was extracted with ethyl acetate. The combined organic layer was washed with a saturated aqueous sodium chloride solution, and then dried. The dried solution was concentrated under reduced pressure to give a solid, which was chromatographed on silica gel to give a pale yellow solid (0.67 g), which was recrystallized from ethyl acetate-hexane to give colorless needles (0.492 g, 81%), m.p.145°–146° C.

$^1$H-NMR (200 MHz, CDCl$_3$) δ: 1.56(3H,d,J=6.5 Hz), 2.07(3H,s), 2.66(3H,s), 3.04(3H,s), 5.19(2H,s), 6.13(1H,q, J=6.5 Hz), 6.94(2H,d,J=8.8 Hz), 7.10–7.50(6H,m), 7.53(1H, s).

Working Example 46

5-(1-Acetoxyethyl)-4,7-dihydro-7-(2-fluorobenzyl)-2-(4-methoxyphenyl)-3-(N-methyl-N-benzylaminomethyl)-4-oxothieno[2,3-b]pyridine To a solution of the compound 13 produced in Working Example 7 (0.15 g, 0.28 mmol) in dimethylformamide (DMF) (15 ml) were added, at room temperature, ethyl diisopropylamine (0.094 g, 0.34 mmol) and N-benzylmethyl amine (0.041 g, 0.34 mmol). After stirring for one hour, the reaction mixture was concentrated under reduced pressure. The concentrate was partitioned between ethyl acetate (50 ml) and a saturated aqueous solution of sodium hydrogencarbonate (10 ml). The aqueous layer was extracted with ethyl acetate. The combined organic layer was washed with a saturated aqueous sodium chloride solution, which was then dried. The dried solution was concentrated under reduced pressure to give a solid, which was chromatographed on silica gel to give a pale yellow solid (0.05 g), which was recrystallized from ethyl acetate-diethyl ether to give colorless crystals (0.05 g, 29%), m.p.183°–187° C.

| Elemental Analysis for C$_{34}$H$_{33}$N$_2$O$_4$SF.2H$_2$2H$_2$O: | | | |
|---|---|---|---|
| | C(%) | H(%) | N(%) |
| Calcd. | 65.79 | 6.00 | 4.51 |
| Found | 63.69 | 5.55 | 5.02 |

$^1$H-NMR (500 MHz, CDCl$_3$) δ: 1.59(3H,d,J=6.9 Hz), 2.09(3H,s), 2.88(3H,d,J=4.7 Hz), 3.88(3H,s), 4.40(1H,m), 4.5–4.7(3H,m), 5.46(2H,s), 6.16(1H,m), 7.08(2H,d,J=7.2 Hz), 7.16(1H,t,J=9.5 Hz), 7.22(1H,t,J=7.6 Hz), 7.3–7.4(3H, m), 7.4–7.5(6H,m), 7.97(1H,s). FAB-Mass m/z 585(MH)$^+$.

Working Example 47

Starting from the compound produced in Working Example 7, compounds set forth in Table 26 were produced in accordance with substantially the same method as described in Working Example 46.

TABLE 26

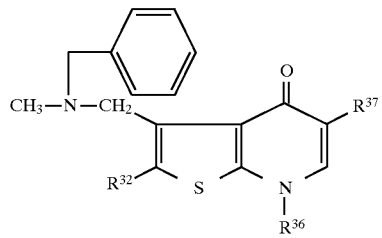

| W. Ex. 47 Cpd. No. | R$^{32}$ | R$^{36}$ | R$^{37}$ | Yield (%) | m.p. (°C.) |
|---|---|---|---|---|---|
| 1 | 4-nitrophenyl | 2,6-difluoro-benzyl | benzoyl | 83 | 197–199 |
| 2 | 4-nitrophenyl | 2,6-difluoro-benzyl | isobutyryl | 66 | 151–152 |
| 3 | 4-ethoxy-carbonyl-phenyl | 2,6-difluoro-benzyl | benzoyl | 87 | 175–180 (hydro-chloride) 169–171 (free base) |
| 4 | 4-butoxy-phenyl | 2-fluoro-benzyl | ethoxy-carbonyl | 72 | 200–202 |

Working Example 48

4,7-Dihydro-7-(2-fluorobenzyl)-5-(1-hydroxyethyl)-2-(4-methoxyphenyl)-3-(N-methyl-N-benzylaminomethyl)-4-oxothieno[2,3-b]pyridine To a solution of the compound produced in Working Example 46 (0.15 g, 0.28 mmol) in methanol (5 ml) was added an aqueous solution of potassium carbonate (prepared by dissolving 0.012 g of potassium carbonate in 1 ml of water). After stirring for 3 hours, the reaction mixture was concentrated under reduced pressure. The concentrate was partitioned between ethyl acetate (20 ml) and a saturated aqueous solution of sodium hydrogencarbonate (10 ml). The aqueous layer was extracted with ethyl acetate. The combined organic layer was washed with a saturated aqueous sodium chloride solution, and then dried. The dried solution was concentrated under reduced pressure to give a solid (0.018 g, 77%), m.p.183°–187° C.

| Elemental Analysis for $C_{32}H_{31}N_5O_3SF.H_2O$: | | | |
|---|---|---|---|
| | C(%) | H(%) | N(%) |
| Calcd. | 68.55 | 5.93 | 5.00 |
| Found | 68.69 | 5.79 | 4.92 |

$^1$H-NMR (500 MHz, CDCl$_3$) δ: 1.56(3H,d,J=6.4 Hz), 2.16(3H,s), 3.68(2H,br), 3.86(3H,s), 4.17(2H,s), 4.7–4.9 (1H,br s), 4.97(1H,q,J=6.4 Hz), 5.22(2H,s), 6.95(2H,d,J=6.9 Hz), 7.1–7.3(5H,m), 7.13–7.18(3H,m), 7.37(1H,m), 7.46 (1H,s), 7.74(2H,d,J=8.6 Hz). FAB-Mass m/z 543(MH)$^+$.

Working Example 49

Starting from the compound produced in Working Example 27, the compounds set forth in Table 27 were produced in accordance with substantially the same methods described in Working Examples 23, 24 and 37.

TABLE 27

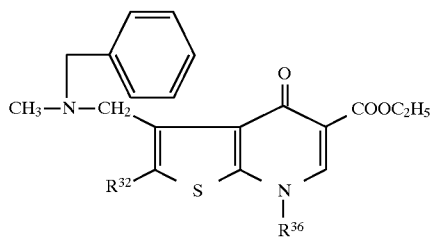

| W. Ex. 49 Cpd. No. | R$^{32}$ | R$^{36}$ | Yield (%) | m.p. (°C.) |
|---|---|---|---|---|
| 1 | 4-N'-methyl-ureidophenyl | 2-chloro-6-fluorobenzyl | 63 | 199–200 |
| 2 | 4-N'-methyl-ureidophenyl | 2-chloro-6-fluorobenzyl | 30 | 182–184 |
| 3 | 4-propionyl-aminophenyl | 2-chloro-6-fluorobenzyl | 46 | 172–173 |
| 4 | 4-N'-methyl-ureidophenyl | 2,6-difluoro-benzyl | 79 | 214–215 |
| 5 | 4-propionyl-aminophenyl | 2,6-difluoro-benzyl | 100 | 100–102 |
| 6 | 4-N'-methylthio-ureidophenyl | 2,6-difluoro-benzyl | 74 | 215–217 |
| 7 | 4-(2-methoxy-propionyl-amino)phenyl | 2,6-difluoro-benzyl | 62 | 110–112 |
| 8 | 4-n-butyryl-aminophenyl | 2-fluoro-benzyl | 48 | 203–204 |
| 9 | 4-valeryl-aminophenyl | 2-fluoro-benzyl | 47 | 206–208 |
| 10 | 4-ethoxy-carbonylamino-phenyl | 2-fluoro-benzyl | 40 | amor-phous |
| 11 | 4-N'-methyl-thioureido-phenyl | 2-fluoro-benzyl | 59 | 204–205 |
| 12 | 4-N'-phenyl-ureidophenyl | 2-fluoro-benzyl | 48 | 205–207 |

Working Example 50

4,7-Dihydro-7-(2,6-difluorobenzyl)-3-(N-methyl-N-benzylaminomethyl)-2-(4-nitrophenyl)-4-oxothieno[2,3-b]pyridine-5-(N-isopropyl)carboxamide To a solution of isopropylamine (0.296 g, 5 mmol) in anhydrous methylene chloride (5 ml) was added dropwise at 0° C. a hexane solution of trimethyl aluminum (15%, 2.41 ml, 5.0 mmol) in hexane. The mixture was allowed to warm to room temperature and stirred for further one hour. To this solution was added, with ice-cooling (0° C.), a solution of the compound 2 produced in Working Example 26 (0.12 g, 0.25 mmol) in anhydrous methylene chloride (3 ml), over a period of 30 minutes. The mixture was stirred for further one hour at room temperature, to which was added chloroform (50 ml), and the mixture was washed with water. The combined organic layer was dried over sodium sulfate, which was concentrated to give a solid. The solid was recrystallized from chloroform-ethyl acetate-ethyl ether to give colorless crystals (0.096 g, 70%), m.p.200°–202° C.

$^1$H-NMR (500 MHz, CDCl$_3$) [free amine] δ: 1.30(6H,d, J=6.7 Hz), 2.15(3H,s), 3.66(2H,s), 4.18(2H,s), 4.18–4.31 (1H,m), 5.32(2H,s), 7.00(2H,t,J=7.26 Hz), 7.13–7.25(5H, m), 7.42(1H,t,J=7.3 Hz), 8.02(2H,d,J=8.9 Hz), 8.26(2H,d, J=8.9 Hz), 8.73(1H,s), 10.02(1H,d,J=9.1 Hz). IR (KBr): 2974, 1661, 1597, 1547, 1497, 1346, 1212, 1035 cm$^{-1}$. FAB-Mass m/z 617(MH)$^+$.

Working Example 51

Starting from the compounds produced in Working Examples 26, 27, 37, 38 and 49, compounds set forth in Table 28 and Table 29 were produced in accordance with substantially the same procedure as described in Working Example 50.

TABLE 28

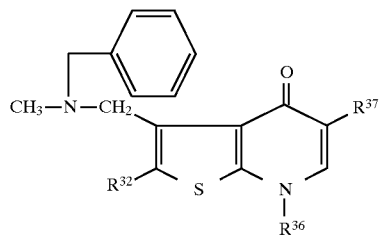

| W. Ex. 51 Cpd. No. | R$^{32}$ | R$^{36}$ | R$^{37}$ | Yield (%) | m.p. (°C.) |
|---|---|---|---|---|---|
| 1 | 4-N'-methyl-ureidophenyl | 2,6-difluoro-benzyl | N-isopropyl-N-methyl-carboxamide | 76 | 133–135 (184–186 as hydro-chloride) |
| 2 | 4-N'-methyl-ureidophenyl | 2,6-difluoro-benzyl | N-methyl-O-methyl-hydro-xamic acid | 80 | 138–140 |
| 3 | 4-propionyl-aminophenyl | 2,6-difluoro-benzyl | N,N-dimethyl-carboxamide | 55 | 110–112 |
| 4 | 4-propionyl-aminophenyl | 2,6-difluoro-benzyl | pyrrolidinyl amide | 43 | 130–132 |
| 5 | 4-propionyl-aminophenyl | 2,6-difluoro-benzyl | N',N'-dimethyl-amino-1,3-propylcar-boxamide | 46 | 90–92 |
| 6 | 4-propionyl-aminophenyl | 2,6-difluoro-benzyl | N-methyl-N-butyl-carboxamide | 28 | 120–122 |
| 7 | 4-N'-methyl-ureidophenyl | 2,6-difluoro-benzyl | N-methyl-N-benzyl-carboxamide | 27 | 135–137 (179–181 as hydro-chloride) |
| 8 | 4-N'-methyl-ureidophenyl | 2,6-difluoro-benzyl | N-isopropyl-carboxamide | 55 | 148–150 |
| 9 | 4-nitro-phenyl | 2,6-difluoro- | 4-methyl-O-methyl- | 96 | 100–102 |

TABLE 28-continued

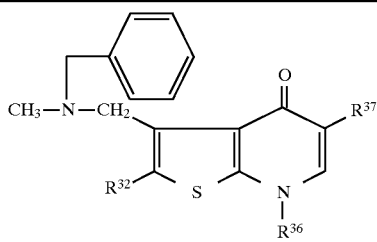

| W. Ex. 51 Cpd. No. | R³² | R³⁶ | R³⁷ | Yield (%) | m.p. (°C.) |
|---|---|---|---|---|---|
|  |  | benzyl | hydroxamic acid |  |  |
| 10 | 4-propionyl-aminophenyl | 2,6-difluorobenzyl | N-isopropyl-carboxamide | 56 | 144–146 |
| 11 | 4-propionyl-aminophenyl | 2,6-difluorobenzyl | N-butyl-carboxamide | 32 | 107–109 |
| 12 | 4-N'-methyl-ureidophenyl | 2-chloro-6-fluorobenzyl | N-isopropyl-carboxamide | 77 | 172–174 |
| 13 | 4-propionyl-aminophenyl | 2-chloro-6-fluorobenzyl | N-isopropyl-carboxamide | 75 | 120–122 |
| 14 | 4-propionyl-aminophenyl | 2-chloro-6-fluorobenzyl | N-butyl-carboxamide | 40 | 105–107 |
| 15 | 4-acetyl-aminophenyl | 2-fluoro-benzyl | N-isopropyl-carboxamide | 83 | 184–186 |
| 16 | 4-propionyl-aminophenyl | 2,6-difluorobenzyl | N-methyl-O-methyl-hydroxamic acid | 74 | amorphous |
| 17 | 4-N'-methyl-ureidophenyl | 2,6-difluorobenzyl | N-methyl-N-(2-pyridyl)-carboxamido | 54 | 156–158 (hydrochloride) |
| 18 | 4-propionyl-aminophenyl | 2,6-difluorobenzyl | N-methyl-N-(2-pyridyl)-carboxamido | 85 | 148–150 (hydrochloride) |
| 19 | 4-N'-methyl-ureidophenyl | 2,6-difluorobenzyl | N-ethyl-N-benzyl-carboxyamide | 26 | 125–127 (hydrochloride) |

TABLE 29

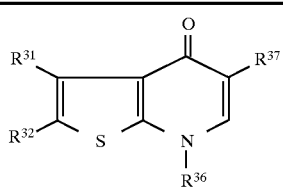

| W. Ex. 51 Cpd. No. | R³¹ | R³² | R³⁶ | R³⁷ | Yield (%) | m.p. (°C.) |
|---|---|---|---|---|---|---|
| 20 | methyl | bromine | 2,6-difluorobenzyl | N-methyl-O-methylcarbohydroxiamic acid | 87 | 192–194 |

Working Example 52

5-Benzoyl-(2,6-difluorobenzyl)-4,7-dihydro-7-3-methyl-2-(4-nitrophenyl)-4-oxothieno[2,3-b]pyridine The compound 4 produced in Working Example 12 (3.93 g, 7.87 mmol) was dissolved in anhydrous tetrahydrofuran (THF) under mild heating. To this solution was added dropwise, while keeping at 0° C., a solution of phenyl magnesium bromide in THF (1M, 15.7 ml, 15.7 mmol), over a period of 10 minutes. The mixture was stirred for further one hour. The reaction mixture was partitioned between ethyl acetate (300 ml) and water (50 ml). The aqueous layer was again extracted with ethyl acetate. The combined organic layer was dried over magnesium sulfate, which was concentrated under reduced pressure. The concentrate was chromatographed on silica gel to give yellow crystals (3.00 g, 74%), which was recrystallized from ethyl acetate-hexane; m.p.114°–116° C.

| Elemental Analysis for $C_{28}H_{18}N_2O_4SF_2 \cdot 0.7H_2O$: | | | |
|---|---|---|---|
|  | C(%) | H(%) | N(%) |
| Calcd. | 63.56 | 3.70 | 5.29 |
| Found | 63.83 | 3.95 | 5.08 |

$^1$H-NMR (500 MHz, CDCl$_3$) δ: 2.68(3H,s), 5.30(2H,s), 7.02(2H,t,J=8.1 Hz), 7.43(3H,t,J=7.2 Hz), 7.52–7.63(3H, m), 7.86(2H,d,J=7.5 Hz), 7.99(1H,s), 8.30(2H,d,J=8.7 Hz). IR (KBr): 3422, 3068, 1665, 1615, 1491, 1473, 1346, 853 cm$^{-1}$. FAB-Mass m/z 517(MH)$^+$.

Working Example 53

Starting from the compounds produced in Working Example 51, compounds set forth in Table 30 were produced in accordance with substantially the same procedure as described in Working Example 52.

TABLE 30

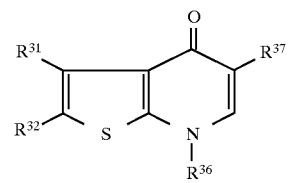

| W. Ex. 53 Cpd. No. | R³² | R³¹ | R³⁶ | R³⁷ | Yield (%) | m.p. (°C.) |
|---|---|---|---|---|---|---|
| 1 | 4-nitrophenyl | N-methyl-N-benzyl-aminomethyl | 2,6-difluorobenzyl | iso-butyryl | 10 | 236–238 (hydrochloride) |
| 2 | phenyl | N-methyl-N-benzyl-aminomethyl | 2,6-difluorobenzyl | iso-butyryl | 52 | 204–205 |
| 3 | bromine | methyl | 2,6-difluorobenzyl | benzoyl | 87 | 229–230 |

Working Example 54

2-(4-Aminophenyl)-5-benzoyl-7-(2,6-difluorobenzyl)-4,7-dihydro-3-(N-methyl-N-benzylaminomethyl)-4-oxothieno[2,3-b]pyridine To a mixture of the compound 1 produced in Working Example 47 (0.30 g, 0.47 mmol) in ethyl alcohol (6 ml) was added one drop of conc. HCl, which made the mixture into a homogeneous solution. To the solution were added dropwise iron powder (0.105 g, 2.0 mmol) and conc. HCl (0.39 ml, 4.7 mmol). After stirring for 5 hours at room temperature, the reaction mixture was filtrated with celite. To the filtrate was added a small volume of aqueous amonia, which was concentrated under reduced pressure. The concentrate was poured into ice-water, which was neutralized with sodium hydrogencarbonate, followed by extraction with ethyl acetate. The combined organic layer was washed with an aqueous sodium chloride solution, followed by drying (MgSO$_4$). The solvent was distilled off under reduced pressure. The residue was chromatographed on silica gel, followed by recrystallization from isopropyl ether to give yellow needles (0.24 g, 84%), m.p.126°–128° C.

| Elemental Analysis for C$_{36}$H$_{29}$N$_3$O$_3$SF$_2$.1/2H$_2$O: | | | |
|---|---|---|---|
| | C(%) | H(%) | N(%) |
| Calcd. | 68.93 | 5.04 | 6.70 |
| Found | 68.71 | 5.18 | 6.62 |

$^1$H-NMR (300 MHz, CDCl$_3$) δ: 2.13(3H,s), 3.65(2H,s), 3.87(2H,br s), 4.14(2H,s), 5.28(2H,s), 6.74(2H,d,J=8.7 Hz), 7.00(2H,t,J=7.8 Hz), 7.16–7.24(5H,m), 7.36–7.46(3H,m), 7.53(1H,t,J=7.2 Hz), 7.62(2H,d,J=8.4 Hz), 7.89(2H,d,J=7.2 Hz), 7.94(1H,s). IR (KBr): 3358, 1607, 1495, 1473, 1035 cm$^{-1}$. FAB-Mass m/z 606(MH)$^+$.

Working Example 55
2-(4-Aminophenyl)-7-(2,6-difluorobenzyl)-4,7-dihydro-5-isobutyryl-3-(N-methyl-N-benzylaminomethyl)-4-oxothieno[2,3-b]pyridine To a solution of the compound 2 produced in Working Example 47 (0.25 g, 0.415 mmol) in methanol (5 ml) were added dropwise, under ice-cooling, iron powder (0.093 g, 1.66 mmol) and conc. HCl (0.8 ml). After stirring for one hour at room temperature, the reaction mixture was filtrated with celite. To the filtrate was added a saturated aqueous solution of sodium hydrogencarbonate (10 ml), which was extracted with methylene chloride (30 ml×3). The combined extract solution was washed with water and dried (MgSO$_4$), then the solvent was distilled off under reduced pressure. The residue was chromatographed on silica gel to give a pale yellow amorphous (0.203 g, 86%).

$^1$H-NMR (300 MHz, CDCl$_3$) δ: 1.18(6H,d), 2.11(3H,s), 3.65(2H,s), 3.85(2H,br s), 4.17(2H,s), 4.18(1H,m), 5.25(2H,s), 6.73(2H,d), 6.95(2H,t), 7.10–7.26(5H,m), 7.42(1H,m), 7.58(2H,d), 8.27(1H,s).

Working Example 56
5-Benzoyl-7-(2,6-difluorobenzyl)-4,7-dihydro-3-(N-methyl-N-benzylaminomethyl)-2-(4-propionylamidophenyl)-4-oxothieno[2,3-b]pyridine The compound produced in Working Example 54 (0.14 g, 0.23 mmol) was dissolved in anhydrous methylene chloride (2 ml). To the solution was added, with ice-cooling (0° C.), triethylamine (0.038 ml). After stirring for a while, to the mixture was added propionyl chloride (0.021 ml, 0.243 mmol). The mixture was then stirred for further 40 minutes with ice-cooling (0° C.). The reaction mixture was partitioned between methylene chloride (25 ml) and an highly dilute aqueous solution of sodium hydrogencarbonate (1 ml). The aqueous layer was again extracted with methylene chloride (25 ml). The combined organic layer was washed with an aqueous sodium chloride solution and dried (MgSO$_4$), then the solvent was distilled off under reduced pressure to give a solid. The solid was recrystallized from ethyl acetate-isopropyl ether to give yellow needles (0.10 g, 65%), m.p.226°–228° C.

| Elemental Analysis for C$_{39}$H$_{33}$N$_3$O$_3$SF$_2$.0.7H$_2$O: | | | |
|---|---|---|---|
| | C(%) | H(%) | N(%) |
| Calcd. | 69.46 | 5.14 | 6.23 |
| Found | 69.60 | 5.18 | 6.04 |

This compound was dissolved in ethyl acetate, to which was added saturated solution of HCl in ether (an equimolar to a little excess amount) to give crystals. The crystals were recrystallized from isopropyl ether to give pale yellow needles (0.095 g, 61%), m.p.218°–220° C.

| Elemental Analysis for C$_{39}$H$_{33}$N$_3$O$_3$SF$_2$.HCl.3.5H$_2$O: | | | |
|---|---|---|---|
| | C(%) | H(%) | N(%) |
| Calcd. | 61.53 | 5.43 | 5.52 |
| Found | 61.83 | 5.33 | 5.30 |

$^1$H-NMR (300 MHz, DMSO-d$_6$) δ: 1.11(3H,t,J=7.2 Hz), 1.93(3H,s), 2.35(2H,q,J=7.5 Hz), 3.44(2H,s), 4.00(2H,s), 5.62(2H,s), 7.11–7.25(6H,m), 7.43–7.72(10H,m), 7.79(2H, d,J=7.5 Hz), 8.40(1H,s), 10.03(1H,s). IR (KBr): 3422, 3068, 1603, 1502, 1473, 1035 cm$^{-1}$. FAB-Mass m/z 662(MH)$^+$.

Working Example 57

Starting from the compounds produced in Working Examples 54 and 55, compounds set forth in Table 31 were produced in accordance with substantially the same procedures as described in Working Examples 56 and 23, 24, 27 and 38.

TABLE 31

[Structure: A thieno[2,3]pyridine core with CH₃—N—CH₂ (benzyl) group attached, R³², R³⁶, R³⁷ substituents, and a ketone]

| W. Ex. 57 Cpd. No. | R³² | R³⁶ | R³⁷ | Yield (%) | m.p. (°C.) | m.p. (°C.) (HCL salt) |
|---|---|---|---|---|---|---|
| 1 | 4-(N'-methyl-ureidophenyl) | 2,6-difluoro-benzyl | benzoyl | 68 | 238–240 | 230–231 |
| 2 | 4-propionyl-aminophenyl | 2,6-difluoro-benzyl | iso-butyryl | 64 | 201–204 | 207–214 |
| 3 | 4-(N'-methyl-ureidophenyl) | 2,6-difluoro-benzyl | iso-butyryl | 55 | 207–210 | 222–226 |
| 4 | 4-ethane-sulfonamido-phenyl | 2,6-difluoro-benzyl | benzoyl | 49 | — | 185–187 |
| 5 | 4-isobutyryl-aminophenyl | 2,6-difluoro-benzyl | benzoyl | 79 | — | 216–218 |
| 6 | 4-(N',N'-dimethyl-ureidophenyl) | 2,6-difluoro-benzyl | benzoyl | 73 | — | 180–183 |
| 7 | 4-(N'-isopropyl-ureidophenyl) | 2,6-difluoro-benzyl | benzoyl | 65 | 245–247 | — |
| 8 | 4-pyrrolidine-carbox-amidephenyl | 2,6-difluoro-benzyl | benzoyl | 65 | — | 176–178 |
| 9 | 4-(2,2,2-trifluoro-ethoxy-carboxylamino phenyl) | 2,6-difluoro-benzyl | benzoyl | 70 | — | 232–234 |
| 10 | 4-isobutyryl-aminophenyl | 2,6-difluoro-benzyl | iso-butyryl | 73 | — | 192–197 |

Working Example 58

5-Benzoyl-7-(2,6-difluorobenzyl)-4,7-dihydro-3-(N-methyl-N-benzylaminomethyl)-2-(4-nitrophenyl)-4-oxothieno[2,3]pyridine The compound 9 produced in Working Example 51 (1.91 g, 3.09 mmol) was dissolved in anhydrous tetrahydrofuran (THF) (30 ml) with warming. To the solution was added dropwise, under ice-cooling (0° C.), a solution of phenyl magnesium bromide in THF (1M, 6.18 ml, 6.2 mmol), over a period of 10 minutes. After stirring for one hour under ice-cooling, the reaction mixture was partitioned between ethyl acetate (100 ml) and HCl (0.5N, 100 ml). The organic layer was again washed with a saturated aqueous sodium chloride solution (100 ml). The organic layer was dried (MgSO₄), then the solvent was distilled off under reduced pressure. The residue was chromatographed on silica gel to give yellow crystals (1.00 g, 51%), followed by recrystallization from isopropyl ether to give yellow needles, m.p.197°–199° C.

| Elemental Analysis for $C_{36}H_{27}N_3O_4SF_2 \cdot 0.7H_2O$: | | | |
|---|---|---|---|
| | C(%) | H(%) | N(%) |
| Calcd. | 66.70 | 4.42 | 6.48 |
| Found | 66.59 | 4.48 | 6.42 |

¹H-NMR (300 MHz, CDCl₃) δ: 2.17(3H,s), 3.61(2H,s), 4.16(2H,s), 5.30(2H,s), 7.03(2H,t,J=8.1 Hz), 7.19–7.25(5H, m), 7.40–7.47(3H,m), 7.56(1H,t,J=7.5 Hz), 7.88(2H,d,J=6.9 Hz), 7.96(1H,s), 8.10(2H,d,J=-8.7 Hz), 8.28(2H,d,J=8.7 Hz). IR (KBr): 3430, 1663, 1611, 1518, 1473, 1348, 853 cm⁻¹. FAB-Mass m/z 636(MH)⁺.

Working Example 59

Starting from the compounds 2, 9 and 16 produced in Working Example 51, compounds set forth in Table 32 were produced in accordance substantially the same procedure as described in Working Example 58. This method is an alternative method of producing the compounds described in Working Examples 56 and 57.

TABLE 32

[Structure: thieno[2,3-d]pyrimidine core with substituents R³¹, R³², R³⁶, R³⁷]

W. Ex. 59

| Cpd. No. | R³¹ | R³² | R³⁶ | R³⁷ | Yield (%) | m.p. (°C.) (HCl salt) |
|---|---|---|---|---|---|---|
| 1 | N-methyl-N-benzyl-aminomethyl | 4-propionyl-amino-phenyl | 2,6-difluoro-benzyl | iso-butyryl | 29 | 207–214 |
| 2 | N-methyl-N-benzyl-aminomethyl | 4-(N'-methyl-ureido-phenyl) | 2,6-difluoro-benzyl | iso-butyryl | 30 | 222–226 |
| 3 | N-methyl-N-benzyl-aminomethyl | 4-propionyl-amino-phenyl | 2,6-difluoro-benzyl | benzoyl | 45 | 218–220 |
| 4 | N-methyl-N-benzyl-aminomethyl | 4-(N'-methyl-ureido-phenyl) | 2,6-difluoro-benzyl | benzoyl | 34 | 230–232 |

Working Example 60

6-(4-Aminophenyl)-2,4(1H,3H)-dioxo-1-(2-fluorobenzyl)-3-phenyl-5-(N-methyl-N-benzylaminomethyl)thieno[2,3-d]pyrimidine The compound 4 produced in Working Example 40 (0.15 g, 0.247 mmol) was dissolved in ethanol (15 ml), to which was added 10% palladium-carbon (15 mg). The mixture was hydrogenized for 8 hours at room temperature under atmospheric pressure in an atmosphere of hydrogen. The reaction mixture was filtrated with celite, and the filtrate was concentrated under reduced pressure. The concentrate was chromatographed on silica gel to give a yellow crystalline amorphous (0.046 g, 32%).

$^1$H-NMR (300 MHz, CDCl$_3$) δ: 2.05(3H,s), 3.57(2H,s), 3.81(2H,br s), 3.89(2H,s), 5.29(2H,s), 6.69(2H,d,J=8.7 Hz), 7.05–7.56(16H,m). FAB-Mass m/z 577(MH)$^+$

Working Example 61

6-(4-Acetylaminophenyl)-2,4(1H,3H)-dioxo-1-(2-fluorobenzyl)-5-(N-methyl-N-benzylaminomethyl)-3-phenylthieno[2,3-d]pyrimidine The compound produced in Working Example 60 (0.63 g, 0.11 mmol) was dissolved in anhydrous pyridine (5 ml), to which was added acetic anhydride (0.01 ml, 0.11 mmol). The mixture was stirred for 2 hours at room temperature. The reaction mixture was concentrated under reduced pressure. The concentrate was partitioned between methylene chloride (30 ml) and a saturated aqueous sodium chloride solution (10 ml). The aqueous layer was again extracted with methylene chloride (30 ml). The combined organic layer was dried over magnesium sulfate, which was concentrated under reduced pressure. The concentrate was chromatographed on silica gel to give a colorless solid (0.01 g, 15%).

$^1$H-NMR (300 MHz, CDCl$_3$) δ: 2.06(3H,s), 2.19(3H,s), 3.57(2H,s), 3.90(2H,s), 5.30(2H,s), 7.04–7.57(16H,s), 7.70 (2H,d,J=8.4 Hz).

Working Example 62

4,7-Dihydro-7-(2-fluorobenzyl)-2-(4-hydroxyphenyl)-3-methyl-4-oxothieno[2,3-b]pyridine-5-caraboxylic acid ethyl ester To a solution of the compound No. 3 produced in Working Example 65 (1.30 g, 2.70 mmol) in tetrahydrofurane (80 ml) was added 1M solution of hydrogen chloride in ether (81 ml, 81 mmol) with ice-cooling. After stirring at room temperature for 60 hours, the reaction mixture was concentrated under reduced pressure. The resulting residue was partitioned between ethyl acetate (100 ml) and saturated aqueous sodium chloride solution (50 ml), and then aqueous layer was extracted with ethyl acetate (50 ml). The combined organic layer was dried over Na$_2$SO$_4$, followed by distilling off the solvent under reduced pressure. The resulting residual solid was recrystallized from ethyl acetate-ethanol to give yellow needles (0.81 g, 69%), m.p. 225°–227° C.

Elemental Analysis for C$_{24}$H$_{20}$NO$_4$SF.0.1H$_2$O:

|  | C(%) | H(%) | N(%) |
|---|---|---|---|
| Calcd. | 65.62 | 4.63 | 3.19 |
| Found | 65.46 | 4.65 | 3.33 |

$^1$H-NMR (300 MHz, CDCl$_3$) δ: 1.30(3H,t,J=7.0 Hz), 4.24(2H,q,J=7.0 Hz), 5.52(2H,s), 6.84(2H,d,J=8.4 Hz), 7.20–7.46(6H,m), 8.65(1H,s), 9.75(1H,s). IR(KBr): 3856, 1711, 1611, 1589, 1510, 1493, 1448 cm$^{-1}$. FAB-Mass m/z 438(MH)$^+$

Working Example 63

4,7-Dihydro-7-(2-fluorobenzyl)-2-(4-hydroxyphenyl)-3-(N-methyl-N-benzylaminomethyl)-4-oxothieno[2,3-b]pyridine-5-caraboxylic acid ethyl ester Employing the compound No. 26 produced in Working Example 7 (0.26 g, 0.46 mmol), N-methylbenzylamine (0.072 ml, 0.56 mmol) and N-ethyldiisopropylamine (0.12 ml, 0.69 mmol) as a starting material, in accordance with substantially the same manner as described in Working Example 8, a yellow amorphous was produced (0.24 g). To the solution of this amorphous in ethanol (6 ml) was added 1N hydrochloric acid (4 ml, 4 mmol) and then stirred at room temperature for 2 hours. To the reaction mixture was added 1N hydrochloric acid (8 ml, 8 mmol) and then stirred at room temperature for 19 hours. To the reaction mixture was added a water containing sodium bicarbonate (1.01 g, 12.0 mmol), followed by extraction with ethyl acetate (30 ml×3). The combined organic layer was dried over $Na_2SO_4$, followed by distilling off the solvent under reduced pressure. The resulting residue was chromatographed on silica gel to give a colourless oil (0.15 g, 58%). To a solution of this oil in ethanol (3 ml) was added an 1M solution of hydrogen chloride in ether (0.35 ml, 0.35 mmol) with ice-cooling, and then the mixture was stirred with ice-cooling for 10 minutes. The reaction mixture was concentrated under reduced pressure, the resulting residue was recrystallized from ether to give a white powder (0.116 g, total yield 41%) as a hydrochloride, m.p. 231°–235° C.

Elemental Analysis for $C_{32}H_{29}N_2O_4SF.HCl.1.5H_2O$:

|  | C(%) | H(%) | N(%) |
|---|---|---|---|
| Calcd. | 61.98 | 5.36 | 4.52 |
| Found | 61.99 | 5.23 | 4.55 |

$^1$H-NMR (300 MHz, $CDCl_3$) δ: 1.39(3H,t,J=7.1 Hz), 2.53(3H,br s), 4.09(2H,br s), 4.38(2H,q,J=7.1 Hz), 4.39(2H, br s), 5.46(2H,s), 7.05(2H,d,J=8.5 Hz), 7.13–7.51(11H,m), 8.57(1H,s). IR(KBr): 3422, 2988, 1719, 1695, 1605, 1543, 1504, 1458 cm$^{-1}$.

Working Example 64

2-(4-n-Butoxyphenyl)-4,7-dihydro-7-(2-fluorobenzyl)-3-methyl-4-oxothieno[2,3-b]pyridine-5-caraboxylic acid ethyl ester To a solution of the compound produced in Working Example 62 (0.30 g, 0.686 mmol) in DMF (10 ml) was added sodium hydride (30 mg, 0.75 mmol) with ice-cooling, and then the mixture was stirred at room temperature for one hour. To this solution was added n-butyl iodied (0.19 g, 1.03 mmol), and then stirred at room temperature for 15 hours. The reaction mixture was concentrated under reduced pressure. The residue was partitioned between ethyl acetate (100 ml) and a saturated aqueous sodium chloride solution (50 ml), and then the aqueous layer was extracted with ethyl acetate (50 ml). The combined organic layer was dried over $Na_2SO_4$, followed by distilling off the solvent under reduced pressure. The resulting residual solid was recrystallized from ethyl acetate-n-hexane to give colourless crystals (0.33 g, 97%), m.p. 119°–121° C.

Elemental Analysis for $C_{28}H_{28}NO_4SF.0.2H_2O$:

|  | C(%) | H(%) | N(%) |
|---|---|---|---|
| Calcd. | 67.64 | 5.76 | 2.82 |
| Found | 67.36 | 5.69 | 2.68 |

FAB-Mass m/z 494(MH)$^+$

Working Example 65

Employing the compound No. 7 produced in Working Example 3 as well as the compound No. 3 produced in Working Example 53, as the starting materials, in accordance with substantially the same procedure as described in Working Example 19, the compounds shown in Table 33 were produced.

TABLE 33

| W. Ex. 65 Cpd. No. | $R^{32}$ | $R^{36}$ | $R^{37}$ | Yield (%) | m.p. (°C.) |
|---|---|---|---|---|---|
| 1 | 4-(4-nitro-benzyloxy-carbonyl)phenyl | 2-fluoro-benzyl | ethoxy-carbonyl | 62 | 188–190 |
| 2 | 4-ethoxy-carbonylphenyl | 2,6-difluoro-benzyl | benzoyl | 64 | 221–223 |
| 3 | 4-methoxy-methoxyphenyl | 2-fluoro-benzyl | ethoxy-carbonyl | 80 | 112–113 |
| 4 | 4-ethoxy-carbonyl-phenyl | 2-methoxy-benzyl | ethoxy-carbonyl | 78 | 171–172 |

Working Example 66

5-Benzoyl-7-(2,6-difluorobenzyl)-4,7-dihydro-2-(4-N-ethylaminocaraboxyphenyl)-3-(N-methyl-N-benzylaminomethyl)-4-oxothieno[2,3-b]pyridine A solution of the compound No. 3 produced in Working Example 47 (0.15 g, 0.226 mmol) in ethanol (3 ml) and THF (3 ml) was treated with an 1N aqueous sodium hydroxide solution (1.2 ml, 1.2 mmol) to give a carboxylic acid derivative. To a solution of this resulting carboxylic acid derivative in THF (5 ml) were added triethylamine (0.084 ml, 0.60 mmol) and isobutyl chloroformate with ice-cooling in an atmosphere of nitrogen, and then the mixture was stirred with ice-cooling for one hour and at room temperature for and half one hour. To this solution was added 70% aqueous ethyl amine solution (0.16 ml, 2.48 mmol) dropwise with ice-cooling, and then the mixture was stirred with ice-cooling for 30 minutes and at room temperature for 2 hours. The reaction mixture was partitioned between a saturated aqueous sodium chloride solution (50 ml) and ethyl acetate (50 ml), and then the aqueous layer was extracted with ethyl acetate (50 ml). The combined organic layer was dried over $Na_2SO_4$ followed by distilling off the solvent under reduced pressure. The resulting residue was chromatographed on silica gel to give a pale yellow amorphous (0.095 g, 63%). To a solution of this amorphous in methylene chloride (4 ml) was added an 1M solution of hydrogen chloride in ether (0.29 ml, 0.29 mmol) with ice-cooling, and then the mixture was stirred with ice-cooling for 10 minutes. The reaction mixture was concentrated under reduced pressure to give a residue, which was crystallized from methylene chloride-ethyl acetate-ether to give pale yellow powder (0.088 g, total yield 56%) as a hydrochloride, m.p. 156°–160° C.

Elemental Analysis for $C_{39}H_{33}N_3O_3SF_2.HCl.1.8H_2O$:

|  | C(%) | H(%) | N(%) |
|---|---|---|---|
| Calcd. | 64.11 | 5.19 | 5.75 |
| Found | 63.88 | 4.90 | 5.59 |

$^1$H-NMR (300 MHz, $CDCl_3$) [free amine] δ: 1.28(3H,t, J=7.2 Hz), 2.13(3H,br s), 3.49–3.58(2H,m), 3.62(2H,br s), 4.16(2H,br s), 5.30(2H,s), 6.23(1H,br s), 6.99–7.05(2H,m), 7.17–7.26(5H,m), 7.39–7.58(4H,m), 7.83–7.97(7H,m).

IR(KBr)[hydrochloride]: 3386, 3064, 1655, 1630, 1605, 1543, 1508, 1497, 1473 cm$^{-1}$. FAB-Mass m/z 662(MH)$^+$

Working Example 67

Employing the compound Nos. 3 and 4 produced in Working Example 47, as the starting materials, in accordance with substantially the same procedure as described in Working Example 66, the compounds shown in Table 34 were produced.

Elemental Analysis for $C_{33}H_{33}N_2O_3SF \cdot HCl \cdot 0.5H_2O$:

|  | C(%) | H(%) | N(%) |
|---|---|---|---|
| Calcd. | 65.82 | 5.86 | 4.65 |
| Found | 66.01 | 5.67 | 4.62 |

TABLE 34

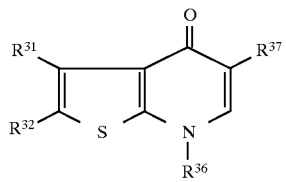

| W. Ex. 67 Cpd. No. | R$^{32}$ | R$^{31}$ | R$^{37}$ | R$^{36}$ | Yield (%) | m.p. (hydrochloride) (°C.) |
|---|---|---|---|---|---|---|
| 1 | 4-N,N-diethyl-aminocarboxyphenyl | N-methyl-N-benzyl-aminomethyl | ethoxycarbonyl | 2-fluorobenzyl | 80 | 110–113° C. |
| 2 | 4-N-propyl-aminocarboxyphenyl | N-methyl-N-benzyl-aminomethyl | benzoyl | 2,6-difluorobenzyl | 75 | 153–157 |
| 3 | 4-N-allyl-aminocarboxyphenyl | N-methyl-N-benzyl-aminomethyl | benzoyl | 2,6-difluorobenzyl | 69 | 152–156 |

Working Example 68

4,7-Dihydro-5-ethoxymethyl-7-(2-fluorobenzyl)-2-(4-methoxyphenyl)-3-(N-methyl-N-benzylaminomethyl)-4-oxothieno[2,3-b]pyridine hydrochloride To a solution of the compound No. 2 produced in Working Example 25 (0.23 g, 0.435 mmol) in anhydrous THF (5 ml) was added sodium hydride (19 mg, 0.475 mmol) in an atmosphere of nitrogen with ice-cooling, and then the mixture was stirred at 0° C. for 30 minutes. To this mixture was added ethyl iodide (0.038 ml, 0.475 mmol), and then allowed to warm to room temperature. After stirring at room temperature for 2 hours, to the reaction mixture was added ethyl iodide (0.038 ml, 0.475 mmol) and then stirred for 19 hours. To the reaction mixture was added a saturated aqueous anmonium chloride solution, and then the mixture was partitioned between ethyl acetate (30 ml) and a saturated aqueous sodium bicarbonate solution (30 ml). The aqueous layer was extracted with ethyl acetate. The combined organic layers were dried over Na$_2$SO$_4$, followed by distilling off the solvent under reduced pressure. The resulting residue was chromatographed on silica gel to give a white solid (0.09 g, 37%). To a solution of this solid in methylene chloride (4 ml) was added an 1M solution of hydrogen chloride in ether (0.2 ml, 0.2 mmol) with ice-cooling, and then the mixture was stirred with ice-cooling for 10 minutes. The reaction mixture was concentrated under reduced pressure to give a residue, which was crystallized from methylene chloride-ethyl acetate-ether to give white powder (0.058 g) as a hydrochloride, m.p. 200°–204° C.

$^1$H-NMR (300 MHz, CDCl$_3$) δ: 1.28(3H,t,J=7.0 Hz), 2.15(3H,br s), 2.86(2H,br s), 3.68(2H,q,J=7.0 Hz), 3.86(3H, s), 4.21(2H,br s), 4.57(2H,s), 5.31(2H,br s), 7.00–7.69(14H, m). FAB-Mass m/z 557(MH)$^+$

Working Example 69

5-Benzyloxymethyl-4,7-dihydro-7-(2-fluorobenzyl)-2-(4-methoxyphenyl)-3-(N-methyl-N-benzylaminomethyl)-4-oxothieno[2,3-b]pyridine hydrochloride Employing the compound No. 2 produced in Working Example 25, as the starting materials, and benyl chloride in place of ethyl iodide, in accordance with substantially the same procedure as described in Working Example 68, the titled compound was produced as a pale yellow crystalline powder (0.10 g, 79%), m.p. 77°–83° C.

Working Example 70

4,7-Dihydro-5-ethylthiomethyl-7-(2-fluorobenzyl)-2-(4-methoxyphenyl)-3-(N-methyl-N-benzylaminomethyl)-4-oxothieno[2,3-b]pyridine hydrochloride To a solution of the compound No. 2 produced in Working Example 25 (0.15 g, 0.284 mmol) in anhydrous THF (5 ml) were added tributylphosphine (0.36 mg, 1.44 mmol) and diethyldisulfide (0.18 ml, 1.46 mmol) and the mixture was refluxed for 5 hours. To this mixture were added tributylphosphine (0.72 ml, 2.88 mmol) and diethyldisulfide (0.36 ml, 2.92 mmol), and the mixture was refluxed for 3 days. After cooling, the reaction mixture was partitioned between ethyl acetate (50 ml) and a saturated aqueous sodium chloride solution (50 ml). The aqueous layer was extracted with ethyl acetate (50 ml). The combined organic layer was dried over Na$_2$SO$_4$, followed by distilling off the solvent under reduced pressure. The resulting residue was chromatographed on silica gel to give a white solid (0.124 g, 76%). To a solution of this solid in methylene chloride (3 ml) was added an 1M solution of hydrogen chloride in ether (0.45 ml, 0.45 mmol) with ice-cooling, and then the mixture was stirred with ice-cooling for 10 minutes. The reaction mixture was concentrated under reduced pressure to give a residue, which was crystallized from methylene chloride-ethyl acetate-ether to give white powder (0.09 g) as a hydrochloride, m.p. 213°–217° C.

Elemental Analysis for C$_{33}$H$_{33}$N$_3$O$_2$S$_2$F.HCl.H$_2$O:

|  | C(%) | H(%) | N(%) |
| --- | --- | --- | --- |
| Calcd. | 63.19 | 5.78 | 4.47 |
| Found | 63.21 | 5.69 | 4.59 |

$^1$H-NMR (300 MHz, CDCl$_3$) δ: 1.27(3H,t,J=7.4 Hz), 2.23(3H,br s), 2.56(2H,q,J=7.4 Hz), 3.76(2H,s), 3.79(2H,br), 3.86(3H,s), 4.25(2H,br s), 5.25(2H,s), 6.97(2H,d,J=8.6 Hz), 7.12–7.39(10H,m), 7.71(2H,br s). IR(KBr): 3480, 2966, 1609, 1520, 1458 cm$^{-1}$. FAB-Mass m/z 573(MH)$^+$ Working Example 71

7-(2,6-Difluorobenzyl)-4,7-dihydro-6-isobutyl-3-(N-methyl-N-benzylaminomethyl)-4-oxo-2-(4-propionylaminophenyl)thieno[2,3-b]pyridine-5-carboxylic acid ethyl ester hydrochloride To a mixture of the compound No. 5 produced in Working Example 49 (0.10 g, 0.159 mmol) and copper iodide (0.095 g, 0.5 mmol) was added isobutylmagnesium bromide (0.5 ml, 1 mmol) with ice-cooling. To the mixture was added anhydrous THF (20 ml) with ice-cooling and the mixture was stirred for one hour. The reaction mixture was poured into a saturated aqueous ammonium chloride solution, and the mixture was extracted with ethyl acetate (50 ml×3). The combined organic layers was dried over Na$_2$SO$_4$, followed by distilling off the solvent under reduced pressure. The resulting brown oil (0.124 g) was dissolved methylene chloride (5 ml), to this solution was added dichlorodicyanoquinone (0.0207 g, 0.091 mmol) and the mixture was stirred with ice-cooling for 2 hours. The reaction mixture was partitioned between chloroform (50 ml) and water (30 ml). The aqueous layer was extracted with chloroform (50 ml). The combined organic layer was dried over Na$_2$SO$_4$, followed by distilling off the solvent under reduced pressure to give a brown oil (0.02 g, 32%). The oil was crystallized from ethyl acetate-n-hexane to give dark brown crystals, m.p. 135°–137° C.

Elemental Analysis for
C$_{39}$H$_{41}$N$_3$O$_4$SF$_2$.C$_8$H$_5$Cl$_2$N$_2$O$_2$.1.4NaCl:

|  | C(%) | H(%) | N(%) |
| --- | --- | --- | --- |
| Calcd. | 58.49 | 4.91 | 6.35 |
| Found | 58.34 | 5.01 | 6.75 |

$^1$H-NMR (300 MHz, CDCl$_3$) δ: 1.07(6H,br s), 1.23(3H,br s), 1.46(3H,t,J=6.3 Hz), 2.10(1H,br s), 2.30–2.96(7H,m), 4.30–4.53(6H,m), 5.55(2H,br s), 6.94–7.90(12H,m). IR(KBr): 3428, 2970, 2214, 1725, 1688, 1628, 1589, 1504, 1470, 1386, 1152, 1025, 789, 748, 700 cm$^{-1}$. FAB-Mass m/z 686(MH)$^+$ Working Example 72

5-Cyano-4,7-dihydro-7-(2-fluorobenzyl)-2-(4-methoxyphenyl)-3-methyl-4-oxothieno[2,3-b]pyridine A mixture of the compound No. 6 produced in Working Example 12 (0.435 g, 1.03 mmol) and phosphorus oxychloride (0.145 ml, 1.56 mmol) was refluxed for one hour. After cooling, the reaction mixture was partitioned between chloroform and aqueous solution of sodium bicarbonate, and then aqueous layer was extracted with chloroform. The combined organic layer was washed with aqueous sodium chloride solution and dried over MgSO$_4$, followed by distilling off the solvent under reduced pressure. The resulting residue was chlomatographed on silica gel, followed by recrystallization from ethyl acetate-isopropylether to give pale yellow crystals (0.225 g, 70%), m.p. 215°–216° C.

Working Example 73

5-Ethylsulfinylmethyl-4,7-dihydro-7-(2-fluorobenzyl)-2-(4-methoxyphenyl)-3-(N-methyl-N-benzylaminomethyl)-4-oxothieno[2,3-b]pyridine hydrochloride To a solution of the compound produced in Working Example 71 (0.15 g, 0.26 mmol) in methylenechloride (4 ml) was added 1M hydrogen chloride solution in ether (0.29 ml, 0.29 mmol) with ice-cooling and the mixture was stirred for 5 minutes with ice-cooling. The mixture was concentrated under reduced pressure to give a yellow amorphous. To an ice-cooled solution of this amorphous in methylene chloride (5 ml) was added dropwise a solution of m-chloroperbenzoic acid (45 mg, 0.26 mmol) in methylene chloride (5 ml) over a period of 10 minutes. After being stirred at 0° C. for 1.5 hours and at room temperature for 1.5 hours, the reaction mixture was partitioned between chloroform and an aqueous solution of sodium bicarbonate. The aqueous layer was separated and extracted with chloroform. The combined organic layer was washed with an aqueous sodium chloride solution and dried over MgSO$_4$, followed by distilling off the solvent under reduced pressure. The resulting residue was chromatographed on silica gel to give a pale yellow syrup (60 mg, 38.9%). To an ice-cooled solution of this syrup (50 mg, 0.085 mmol) in methylene chloride (4 ml) was added an 1M solution of hydrogen chloride in ether (0.13 ml, 0.13 mmol), and then the mixture was stirred with ice-cooling for 5 minutes. The reaction mixture was concentrated under reduced pressure to give a residue, which was recrystallized from ether to give yellow powders (37 mg, 53%) as a hydrochloride, m.p. 216°–219° C.

Working Example 74

6-(Aminophenyl)-2,4(1H,3H)-dioxo-1-(2,6-difluorobenzyl)-5-(N-methyl-N-benzylaminomethyl)-3-phenylthieno[2,3-d]pyrimidine Employing the compound No. 17 produced in Working Example 40, as the starting material, in accordance with substantially the same procedure as described in Working Example 60, the titled compound was produced as a crystalline amorphous (yield 65%).

$^1$H-NMR (300 MHz, CDCl$_3$) δ: 2.05(3H,s), 3.56(2H,s), 3.81(2H,br s), 3.88(2H,s), 5.36(2H,s), 6.71(2H,d,J=8.7 Hz), 6.91(2H,t,J=8.7 Hz), 7.21–7.53(13H,m).

Working Example 75

Employing the compound produced in Working Example 60, as the starting material, in accordance with substantially the same procedure as described in Working Example 61, the following compounds were produced.

No. 1: 2,4(2H,3H)-Dioxo-1-(2-fluorobenzyl)-5-(N-methyl-N-benzylaminomethyl)-3-phenyl-6-(4-propionylaminophenyl)thieno[2,3-d]pyrimidine hydrochloride (yield: 86%, m.p. 172°–175° C.)

No. 2: 2,4(2H,3H)-Dioxo-1-(2-fluorobenzyl)-6-(4-isobutyrylaminophenyl)-5-(N-methyl-N-benzylaminomethyl)-3-phenylthieno[2,3-d]pyrimidine hydrochloride (yield: 77%, m.p. 185°–188° C.)

No. 3: 2,4(2H,3H)-Dioxo-1-(2-fluorobenzyl)-6-(4-methoxyacetylaminophenyl)-5-(N-methyl-N-benzylaminomethyl)-3-phenylthieno[2,3-d]pyrimidine hydrochloride (yield: 88%, m.p. 157°–162° C.)

Working Example 76

Using the compound produced in Working Example 8 (100 mg), lactose (165 mg), corn starch (5 mg), polyvinyl alcohol (4 mg) and magnesium stearate (1 mg), a tablet was prepared by a conventional method.

Working Example 77

The compound produced in Working Example 8 (5 g) was dissolved in distilled water for injection to make the whole volume 100 ml. The solution was subjected to sterilized filtration with 0.22 μm membrane filter (manufactured by Sumitomo Electric Industries, Ltd. or by Zartolius, Inc.), 2 ml each of which was distributed to sterilized vials, followed by lyophilization by a conventional means to give lyophilized injectable solution of 100 mg/vial.

Working Example 78

Using the compound 15 produced in Working Example 9 (100 mg), lactose (165 mg), corn starch (25 mg), polyvinyl alcohol (4 mg) and magnesium stearate (1 mg), a tablet was prepared by a conventional method.

Working Example 79

The compound 15 produced in Working Example 9 (5 g) was dissolved in distilled water for injection to make the whole volume 100 ml. This solution was subjected to sterilized filtration with 0.22 μm membrane filter (manufactured by Sumitomo Electric Industries, Ltd. or Zartolius, Inc.), 2 ml each of which was distributed to sterilized vials, followed by lyophilization by a conventional means to prepare lyophilized injectable solution of 100 mg/vial.

Working Example 80

Using the compound 3 produced in Working Example 21 (100 mg), lactose (165 mg), corn starch (25 mg), polyvinyl alcohol (4 mg) and magnesium stearate (1 mg), a tablet was prepared by a conventional method.

Working Example 81

The compound 3 produced in Working Example 21 (5 g) was dissolved in distilled water for injection to make the whole volume 100 ml. This solution was subjected to sterilized filtration with 0.22 μm membrane filter (manufactured by Sumitomo Electric Industries, Ltd. or Zartolius, Inc.), 2 ml each of which was distributed to sterilized vials, followed by lyophilization by a conventional means to prepare lyophilized injectable solution of 100 mg/vial.

Working Example 82

Using the compound produced in Working Example 23 (100 mg), lactose (165 mg), corn starch (25 mg), polyvinyl alcohol (4 mg) and magnesium stearate (1 mg), a tablet was prepared by a conventional method.

Working Example 83

The compound produced in Working Example 23 (5 g) was dissolved in distilled water for injection to make the whole volume 100 ml. This solution was subjected to sterilized filtration with 0.22 μm membrane filter (manufactured by Sumitomo Electric Industries, Ltd. or Zartolius Inc.), 2 ml each of which was distributed to sterilized vials, followed by lyophilization by a conventional means to prepare lyophilized injectable solution of 100 mg/vial.

Working Example 84

Using the compound produced in Working Example 56 (100 mg), lactose (165 mg), corn starch (25 mg), polyvinyl alcohol (4 mg) and magnesium stearate (1 mg), tablets are prepared by a conventional method.

Working Example 85

In distilled water for injection is dissolved the compound produced in Working Example 56 (5 g) to make the whole volume 100 ml. This solution is subjected to sterilized filtration through a membrane filter of 0.22 μm thick (manufactured by Sumitomo Electric Industries, Ltd. or Zartolius Inc., 2 ml each of which was divided into sterilized vials, followed by lyophilization to prepare a lyophilized injectable composition of 100 mg/vial.

Working Example 86

Using the compound 2 produced in Working Example 57 (100 mg), lactose (165 mg), cornstarch (25 mg), polyvinyl alcohol (4 mg) and magnesium stearate (1 mg), tablets are prepared by a conventional method.

Working Example 87

The compound 2 produced in Working Example 57 (5 g) is dissolved in distilled water for injection to make the whole volume 100 ml. This solution was subjected to sterilized filtration through 0.22 μm membrane filter (manufactured by Sumitomo Electric Industries, Ltd. or Zartolius Inc.), 2 ml each of which was divided into sterilized vials, followed by lyophilization to prepare a lyophilized injectable composition of 100 mg/vial.

Working Example 88

The compound 3 produced in Working Example 57 (100 mg), lactose (165 mg), cornstarch (25 mg), polyvinyl alcohol (4 mg) and magnesium stearate (1 mg), tablets are prepared by a conventional method.

Working Example 89

The compound 3 produced in Working Example 57 (5 g) is dissolved in distilled water for injection to make the whole volume 100 ml. This solution is subjected to sterilized filtration through 0.22 μm membrane filter (manufactured by Sumitomo Electric Industries, Ltd, or Zartolius Inc.), 2 ml each of which is divided into sterilized vials, followed by lyophilization to prepare a lyophilized injectable composition of 100 mg/vial.

Working Example 90

The compound 7 produced in Working Example 51 (5 g) is dissolved in distilled water for injection to make the whole volume 100 ml. This solution is subjected to sterilized filtration through 0.22 μm membrane filter (manufactured by Sumitomo Electric Industries, Ltd. or Zartolius Inc.), 2 ml each of which is distributed to sterilized vials, followed by lyophilization to prepare a lyophilized injectable composition of 100 mg/vial.

Working Example 91

The compound 8 produced in Working Example 51 (5 g) is dissolved in distilled water for injection to make the whole volume 100 ml. This solution is subjected to sterilized filtration through 0.22 μm membrane filter (manufactured by Sumitomo Electric Industries, Ltd. or Zartolius Inc.), 2 ml each of which is divided into sterilized vials, followed by lyophilization to prepare a lyophilized injectable composition of 100 mg/vial.

Working Example 92

| | | |
|---|---|---|
| (1) Compound produced in Working Example 56 | 5 | g |
| (2) Lactose.crystalline cellulose (granules) | 330 | g |
| (3) D-mannitol | 29 | g |
| (4) Low-substituted hydroxypropyl cellulose | 20 | g |
| (5) Talc | 25 | g |
| (6) Hydroxypropyl cellulose | 50 | g |
| (7) Aspartame | 3 | g |
| (8) Dipotassium glycyrrhetinate | 3 | g |
| (9) Hydroxypropylmethyl cellulose 2910 | 30 | g |
| (10) Titanium oxide | 3.5 | g |
| (11) Yellow iron sesquioxide | 0.5 | g |
| (12) Light silicic acid anhydride | 1 | g |

In refined water were suspended or dissolved (1), (3), (4), (5), (7) and (8). The nuclear granule of (2) was coated with the suspension or solution to prepare raw fine granules, which were coated with (9)-(11) to prepare coated fine granules, which were mixed with (12), to give 500 g of fine granules containing 1% of the compound produced in Working Example 56. 500 mg each of thus-prepared fine granules was packed.

Test Example 1
Preparation of $^{125}$I-leuprorelin

Ten μl of a $3\times10^{-4}$M aqueous solution of leuprorelin and 10 μl of 0.01 mg/ml lactoperoxidase in 0.1M HEPES buffer (pH 7.4) were taken into a tube, to which was added 10 μl [37MBq in 0.1M HEPES buffer (pH 7.4)] of an Na$^{125}$I solution. The mixture was stirred, to which was added 10 μl of 0.001% $H_2O_2$, then reaction was allowed to proceed for 20 minutes at room temperature. To the reaction mixture was added 700 μl of a 0.05% TFA solution to stop the reaction. The product was purified by means of reversed phase HPLC. Conditions of HPLC are as follows. $^{125}$I-leuprorelin was eluted at a retention time of 26 to 27 minutes.

Column : TSK gel ODS-80™CTR (4.6 mm×10 cm)

Eluent : Solvent A (0.05% TFA)
Solvent B (40%$CH_3$CN-0.05% TFA)
0 minute (100% Solvent A)—3 minutes (100% Solvent A)—7 minutes (50% Solvent A+50% Solvent B)—40 minutes (100% Solvent B)

Elution temp.: room temperature

Flow rate : 1 ml/min.

Test Example 2
Preparation of membrane fraction of rat pituitary anterior lobes of containing GnRH receptors Forty Wister rats (8 week old, male) were killed and the pituitary anterior lobes were collected and washed with an ice-cooled homogenate buffer (25 mM Tris (tris (hydroxymethyl)aminomethane)-HCl, 0.3M saccharose, 1 mM EGTA (glycoletherdiamine tetraacetate), 0.25 mM PMSF (phenylmethylsulfonyl fluoride), 10 U/ml aprotinin, 1 μg/ml pepstatin, 20 μg/ml leupeptin, 100 μg/ml phosphoramidon, 0.03% sodium azide, pH 7.5). The pituitary gland was suspended in 2 ml of the homogenate buffer, which was homogenated with a Polytron homogenizer. Centrifugal separation was conducted for 15 minutes at 700×g. The supernatant was collected into an ultracentrifuge tube, which was subjected to centrifuge for one hour at 100,000×g to give membrane fraction as precipitate. This precipitate was suspended in 2 ml of an assay buffer (25 mM Tris-HCl, 1 mM EDTA (ethylenediamine tetraacetate), 0.1% BSA (bovine serum albumin), 0.25 mM PMSF, 1 μg/ml pepstatin, 20 μg/ml leupeptin, 100 μg/ml phosphoramidon, 0.03% sodium azide, pH 7.5), which was subjected to centrifugal separation for one hour at 100,000×g. The membrane fraction recovered as precipitate was again suspended in 10 ml of the assay buffer, which was distributed into vials and stored at −80° C. until used.

Test Example 3

Preparation of membrane fraction of CHO (Chinese Hamster Ovary) cells containing human GnRH receptors CHO cells ($10^9$) expressing human GnRH receptors were suspended in a phosphate-buffered saline supplemented with 5 mM EDTA (PBS-EDTA). The suspension was subjected to centrifugal separation for 5 minutes at 100×g. To the pellet of cells was added 10 ml of a homogenate buffer for cells (10 mM $NaHCO_3$, 5 mM EDTA, pH 7.5), which was homogenated by using a Polytron homogenizer. Centrifugal separation was conducted for 15 minutes at 400×g. The supernatant was taken into an ultracentrifugal tube, which was subjected to centrifuge for one hour at 100,000×g to give precipitate of the membrane fraction. The precipitate was suspended in 2 ml of the assay buffer, which was centrifuged for one hour at 100,000×g. The membrane fraction recovered as precipitate was again suspended in 20 ml of the assay buffer, which was distributed to vials and stored at −80° C. until used.

Test Example 4
Determination of inhibitory rate of $^{125}$I-leuprorelin binding Membrane fractions of rat pituitary and CHO cells expressing human GnRH receptors prepared in Test Examples 2 and 3 were respectively diluted with an assay buffer to 200 μg/ml and 188 μl each was distributed into tubes. In the case where the membrane fraction of rat pituitary anterior lobes were used, 2 μl of 0.1 mM of the compound dissolved in 60% DMSO (dimethyl sulfoxide) and 10 μl of 38 nM $^{125}$I-leuprorelin were added simultaneously. In the case where the CHO cell membrane fraction expressing human GnRH receptors, 2 μl of 2 mM of the compound dissolved in 60% DMSO and 10 μl of 38 nM $^{125}$I-leuprorelin were added simultaneously. For determining the amount of maximum binding, a solution for reaction supplemented with 2 μl of 60% DMSO and 10 μl of 38 nM $^{125}$I-leuprorelin was prepared. And, for determining the amount of non-specific binding, a solution for reaction supplemented with 2 μl of 100 μM leuprorelin dissolved in 60% DMSO and 10 μl of 38nM $^{125}$I-leuprorelin were also prepared simultaneously.

In the case where the membrane fraction of rat pituitary anterior lobes were used, reaction was allowed to proceed at 4° C. for 90 minutes, while in the case where the CHO cell membrane faction expressing human GnRH receptor was used, reaction was allowed to proceed at 25° C. for 60 minutes. The reaction mixtures were respectively subjected to filtration under sucking with Whatman glass filter (GF-F) processed with polyethylenimine. After completing the filtration, radioactivity of the $^{125}$I-leuprorelin remaining on the filter paper was measured with a γ-counter.

By calculation of (TB-SB)/(TB-NSB)×100 (SB: radioactivity obtained when a compound was added, TB: maximum binding radioactivity, NSB: non-specific binding ratio activity, the binding inhibitory rate (%) of each test compound was determined. Besides, the inhibitory rates were determined by changing the concentrations of test compounds, and the concentration of a test compound inhibiting the (TB-NSB) by 50% ($IC_{50}$ value) was calculated by way of Hill plot. The results are shown in Table 32.

TABLE 32

$^{125}$I-leuprorelin binding inhibitory rate

| Test compound | Binding inhibitory rate (%) | | $IC_{50}$ value (μM) | |
|---|---|---|---|---|
| | rat(1 μM) | human(20 μM) | rat | human |
| Compound of W.Ex.1 | | 67 | | 13 |
| Compound of W.Ex.9 (Compound No.14) | 46 | 112 | 1 | 0.08 |
| Compound of W.Ex.9 (Compound No.15) | 38 | 114 | 1.9 | 0.08 |
| Compound of W.Ex.21 (Compound No.3) | 35 | 106 | 2 | 0.03 |
| Compound of W.Ex.23 | | 107 | | 0.01 |

Test Example 5
Inhibition of LH/FSH secretion by primary cultured cells of rat pituitary anterior lobes.

Anterior lobes of pituitary glands from 40 Wistar rats (8-week old, male) was put into a petri dish containing buffer A (0.7 mM sodium dihydrogen phosphate, 137 mM sodium chloride, 5 mM potassium chloride, 25 mM HEPES, 50 μg/ml gentamicin sulfate), which was once washed with the buffer A, then the anterior lobes were divided into four portions, followed by further washing twice. A portion of thus-washed rat pituitary anterior lobes were put into a conical flask with a stopper containing enzyme solution I (buffer A containing 0.4% collagenase, 0.4% BSA (bovine serum albumin), 10 μg/ml deoxyribonuclease and 0.2% glucose. The mixture was incubated for one hour at 37° C. with shaking. After sucking and discharging with a pipette repeatedly the tissue fragments were dispersed. The dispersion was transferred to a centrifugal tube, which was then centrifuged for 6 minutes to remove the supernatant. To the remainder was added enzyme solution II (enzyme solution A containing 10% pancreatin), and the mixture was incubated for 8 minutes at 37° C., to which was added 2 ml of FCS (fetal calf serum). The mixture was again centrifuged for 6 minutes at 480×g, and the supernatant was removed. The remainder was suspended in 10 ml of culture medium I (Dulbecco modified Eagle's medium containing 10% FCS, 20 mM HEPES, 50 U/ml penicillin G, 50 μg/ml streptomycin, and 3.7 g/l sodium hydrogencarbonate), which was subjected to filtration with nylon mesh. The material collected by the filtration was washed twice with 10 ml each portion of the culture medium I, followed by allowing the cells to be suspended in the culture medium I at a cell density of 5×10$^5$/ml. One ml each of the cell suspension was distributed to each well of a 24-well plate, which was incubated for 3 days in a $CO_2$ incubator at 37° C. under an atmosphere of 5% $CO_2$ -95% air, to which was added 2 ml of the culture medium II (Culture medium I without 10% FCS), followed by incubation for one hour. The culture medium was removed. To each well of the 24-well plate was added 800 μl of fresh culture medium II, followed by addition of 20 μM solution (100 μl) of the compound 15 produced in Working Example 9 dissolved in 0.2% (v/v) dimethyl sulfoxide and 100 μl of 5 nM GnRH simultaneously. The culture in the absence of the compound was employed as the control. After incubation at 37° C. for 3 hours, 500 μl of the culture supernatant was recovered, which was subjected to centrifuge for 10 minutes at 1000×g to collect the supernatant. The concentrations of LH and FSH in the supernatant were determined by using the radio immunoassay kit (Amersham Inc.).

By calculating in accordance with the formula; 100-(LH or FSH concentration in the presence of the compound)/(LH or FSH concentration of the control culture)×100, the inhibiting rate (%) of LH or FSH secretion by each compound was determined. The compound 15 inhibited the LH secretion by 28±9.0% (p<0.01, n=3), and inhibited the FSH secretion by 20±10% (p<0.01, n=3).

From the foregoing results, the compound 15 produced in Working Example 9 was shown to have a GnRH antagonistic activity.

Test Example 6
Suppression of testosterone concentration in rat plasma

The compound 15 produced in Working Example 9 was dissolved in vehicle I (20% propylene glycol—80% physiological saline). The solution was administered once subcutaneously to male SD rats (8-week old, n=5). The dosage was 30 mg per 1 kg of body weight. Animals administered with the vehicle alone were used as control. At 24 hours after the administration, blood was collected from jugular vein under anesthesia with ether. To the blood were immediately added ethylenediamine tetracetate (EDTA) at a final concentration of 3 mg/ml and aprotinin at a final concentration of 300 KIU/ml. The mixture was centrifuged for 15 minutes at 3000×g, and the concentration of testosterone in the plasma was measured by the radio immunoassay.

The rate of testosterone suppression (%) of the test compound was determined by the formula; 100-(concentration of plasma testosterone in the test group)/(concentration of plasma testosterone in the control group)×100.

The compound 15 produced in Working Example 9 showed suppression rate of 38±9.7% (p<0.05).

Test Example 7
Suppression of testosterone concentration in mouse plasma

The compound produced in Working Example 56 was dissolved in vehicle II (0.5% methylcellulose dissolved in distilled water). The solution was administered orally once a day during successive 3 days to male ICR mice (10-week old, n=12). The dosage was 30 mg per 1 kg of body weight. ICR mice administered with vehicle alone were used as control (n=15). At 24 hours after the administration, blood was collected from jugular vein under anesthesia with ether. To the blood were immediately added ethylenediamine tetracetate (EDTA) at a final concentration of 3 mg/ml and aprotinin at a final concentration of 300 KIU/ml. The mixture was centrifuged for 15 minutes at 3000×g, and the concentration of testosterone in the plasma was measured by the radio immunoassay.

The rate of testosterone suppression (%) of the test compound was determined by the formula; 100-(concentration of plasma testosterone in the test group)/(concentration of plasma testosterone in the control group)×100.

The compound produced in Working Example 56 showed a suppression rate of 85±9.7% ($p<0.05$).

The gonadotropin-releasing hormone antagonistic agent of the present invention is effective as a prophylactic or therapeutic agent for the prevention or treatment of several hormone dependent diseases, for example, a sex hormone dependent cancer (e.g. prostatic cancers, pituitary adenoma, cancer of the uterine cervix, breast cancer), prostatic hypertrophy, myoma of the uterus, endometriosis, precocious puberty, amenorrhea syndrome, polycystic ovary syndrome and acne vulgaris, or as a fertility controlling agent (e.g. a contraceptive agent) infertility treating agent, a menstruation controlling agent. Further, in the field of animal husbandry, the gonaolotropin-releasing hormone antagonistic agent of the present invention is effective as agents of controlling oestrus in animals, improving the quality of edible meat, growth regulation of animals, and also a spawning-accelerating agent in the field of fisheries.

INDUSTRIAL APPLICABILITY

A gonadotropin-releasing hormone antagonistic composition of the present invention is effective as a propylactic or therapeutic agent for the prevention or treatment of several hormone dependent diseases, for example, a sex hormone dependent cancer (e.g. prostatic cancer, cancer of uterine cervix, breast cancer, pituitary adenoma), benign prostatic hypertrophy, myoma of the uterus, endometriosis, precocious puberty, amenorrhea, premenstrual syndrome, polycystic ovary syndrome and acne vulgaris; is effective as a fertility controlling agent in both sexes (e.g. a pregnancy controlling agent and a menstrual cycle controlling agent); can be used as a contraceptive of male or female, as an ovulation-inducing agent of female; can be used as an infertility treating agent by using a rebound effect owing to a stoppage of administration thereof; is useful as modulating estrous cycles in animals in the field of animal husbandry, as an agent fro improving the quality of edible meat or promoting the growth of animals; is useful as an agent of spawning promotion in fish.

What is claimed is:

1. A compound which is 3-(N-benzyl-N-methylaminomethyl)-4,7-dihydro-7-(2-methoxybenzyl)-2-(4-methoxyphenyl)-4-oxothieno[2,3-b]pyridine-5-carboxylic acid ethyl ester or its salt.

2. A compound which is 3-(N-benzyl-N-methylaminomethyl)-4,7-dihydro-7-(2-fluorobenzyl)-2-(4-methoxyphenyl)-4-oxothieno[2,3-b]pyridine-5-carboxylic acid ethyl ester or its salt.

3. A compound which is 2-(4-acetylaminophenyl)-3-(N-benzyl-N-methylaminomethyl)-4,7-dihydro-7-(2-fluorobenzyl)-4-oxothieno[2,3-b]pyridine-5-carboxylic acid ethyl ester or its salt.

4. A compound which is 5-benzoyl-3-(N-benzyl-N-methylaminomethyl)-7-(2,6-difluorobenzyl)-4,7-dihydro-4-oxo-2-(4-propionylaminophenyl)-4-oxothieno[2,3-b]pyridine or its salt.

5. A compound which is 5-benzoyl-3-(N-benzyl-N-methylaminomethyl)-7-(2,6-difluorobenzyl)-4,7-dihydro-2-(4-N'-methylureidophenyl)-4-oxothieno[2,3-b]pyridine or its salt.

6. A compound which is 3-(N-benzyl-N-methylaminomethyl)-7-(2,6-difluorobenzyl)-4,7-dihydro-5-isobutyryl-4-oxo-2-(4-propionylaminophenyl)-thieno[2,3-b]pyridine or its salt.

7. A compound which is 3-(N-benzyl-N-methylaminomethyl)-7-(2,6-difluorobenzyl)-4,7-dihydro-5-isobutyryl-2-(4-N'-methylureidophenyl)-4-oxothieno[2,3-b]pyridine or its salt.

8. A compound which is 3-(N-benzyl-N-methylaminomethyl)-7-(2,6-difluorobenzyl)-4,7-dihydro-2-(4-N'-methylureidophenyl)-4-oxothieno[2,3-b]pyridine-5-(N-isopropyl)carboxamide or its salt.

9. A compound which is 3-(N-benzyl-N-methylaminomethyl)-7-(2,6-difluorobenzyl)-4,7-dihydro-2-(4-N'-methylureidophenyl)-4-oxothieno[2,3-b]pyridine-5-(N-isopropyl-N-methyl)carboxamide or its salt.

10. A compound which is 3-(N-benzyl-N-methylaminomethyl)-7-(2,6-difluorobenzyl)-4,7-dihydro-2-(4-N'-methylureidophenyl)-4-oxothieno[2,3-b]pyridine-5-(N-benzyl-N-methyl)carboxamide or its salt.

11. A compound which is 7-(2,6-difluorobenzyl)-4,7-dihydro-3-(N-methyl-N-benzylaminomethyl)-2-(4-isobutyrylaminophenyl)-5-isobutyryl-4-oxo-thieno[2,3-b]pyridine or its salt.

* * * * *